(12) United States Patent
Brown et al.

(10) Patent No.: US 8,093,402 B2
(45) Date of Patent: *Jan. 10, 2012

(54) BENZIMIDAZOLE DERIVATIVES

(75) Inventors: William Brown, Saint Laurent (CA); Shawn Johnstone, Saint Laurent (CA); Denis Labrecque, Saint Laurent (CA)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/023,112

(22) Filed: Feb. 8, 2011

(65) Prior Publication Data
US 2011/0137045 A1    Jun. 9, 2011

Related U.S. Application Data

(62) Division of application No. 11/836,221, filed on Aug. 9, 2007, now Pat. No. 7,906,654.

(60) Provisional application No. 60/837,249, filed on Aug. 11, 2006.

(51) Int. Cl.
A61K 31/4184 (2006.01)
C07D 235/08 (2006.01)
(52) U.S. Cl. .................................. 548/309.7; 514/394
(58) Field of Classification Search ............... 548/309.7
See application file for complete search history.

(56) References Cited

U.S. PATENT DOCUMENTS

| | | | |
|---|---|---|---|
| 3,624,103 A | 11/1971 | De Martiis et al. | |
| 3,839,347 A | 10/1974 | Fisher et al. | |
| 4,722,929 A | 2/1988 | Austel et al. | |
| 4,738,981 A | 4/1988 | Horwell | |
| 6,794,404 B2 | 9/2004 | Beaulieu et al. | |
| 7,096,654 B2 | 8/2006 | Pellenc | |
| 7,618,993 B2 | 11/2009 | Besidski et al. | |
| 7,906,654 B2 * | 3/2011 | Brown et al. ............. | 548/309.7 |
| 2003/0149050 A1 | 8/2003 | Jagtap et al. | |
| 2003/0158188 A1 | 8/2003 | Lee et al. | |
| 2004/0092569 A1 | 5/2004 | Demaine et al. | |
| 2004/0152690 A1 | 8/2004 | Balan et al. | |
| 2004/0248983 A1 | 12/2004 | Morie et al. | |
| 2006/0205802 A1 | 9/2006 | Liu et al. | |
| 2006/0287377 A1 | 12/2006 | Besidski et al. | |
| 2007/0066586 A1 | 3/2007 | Tokumasu et al. | |
| 2008/0015222 A1 | 1/2008 | Besidski et al. | |
| 2008/0022188 A1 | 1/2008 | Tamura et al. | |

FOREIGN PATENT DOCUMENTS

| | | |
|---|---|---|
| DE | 2300521 A1 | 7/1973 |
| EP | 0149200 A1 | 12/1984 |
| EP | 0149200 A1 | 7/1985 |
| EP | 0419210 A1 | 3/1991 |
| EP | 1312601 A1 | 5/2003 |
| EP | 0882718 A1 | 8/2005 |
| GB | 1186504 A | 4/1970 |
| WO | WO-94/22859 A1 | 10/1994 |
| WO | WO-99/00115 A1 | 1/1999 |
| WO | WO-01/12189 A1 | 2/2001 |
| WO | WO-01/85722 A1 | 11/2001 |
| WO | WO-01/96336 A2 | 12/2001 |
| WO | WO-02/50031 A1 | 6/2002 |
| WO | WO-02/072536 A1 | 9/2002 |
| WO | WO-02/085866 A1 | 10/2002 |
| WO | WO-02/090326 A1 | 11/2002 |
| WO | WO-02/100819 A1 | 12/2002 |
| WO | WO-02/100822 A1 | 12/2002 |
| WO | WO-03/014064 A1 | 2/2003 |
| WO | WO-03/022809 A2 | 3/2003 |
| WO | WO-03/027076 A2 | 4/2003 |
| WO | WO-03/049702 A2 | 6/2003 |
| WO | WO-03/053945 A2 | 7/2003 |
| WO | WO-03/068749 A1 | 8/2003 |
| WO | WO-2004/000828 A1 | 12/2003 |
| WO | WO-2004/024154 A1 | 3/2004 |
| WO | WO-2004/024710 A1 | 3/2004 |
| WO | WO-2004/100865 A2 | 11/2004 |
| WO | WO-2004/108712 A1 | 12/2004 |
| WO | WO-2005/021539 A1 | 3/2005 |
| WO | WO-2005/095327 A1 | 10/2005 |
| WO | WO-2006/033620 A1 | 3/2006 |
| WO | WO-2007/073303 A2 | 6/2007 |
| WO | WO-2008/018827 A1 | 2/2008 |

OTHER PUBLICATIONS

Beilstein Institute for Organic Chemistry, Frankfurt-Main, Germany; XP002291482, BRN 838602 abstract and Kamel et al., J. Prakt. Chem., vol. 31, 1966, pp. 100-105.
Beilstein Institute for Organic Chemistry, Frankfurt-Main, Germany; XP002291483 BRN 926470 abstract and Osman: Kolor, ERT., vol. 11, 1969, p. 118.
Beilstein Institute for Organic Chemistry, Frankfurt-Main, Germany, XP002291484 BRN 311062 abstract & Pinnow; Wiskott: Chem. Ber., vol. 32, 1899, p. 900. Beilstein Insitute for Organic Chemistry, Frankfurt-Main, Germany, XP002291485 BRN 189489 abstract & Foster: J. Chem. Soc., 1957, pp. 4687-4688.
Beilstein Institute for Organic Chemistry, Frankfurt-Main, Germany; XP002291490 BRN 326965 abstract & V. Walter; Kessler: J. Prak. Chem., vol. 2, No. 74, 1906, p. 198.
Kumar et al., "Cyanoethylation of Benzimidazoles: Synthesis & Biological Activities of Some New 1-(beta-Cyanoethyl)benzimidazoles & Their Derivatives", Indian Journal of Chemistry, Oct. 1985, vol. 24B, pp. 1098-1101.
Lindberg, et al., "Long-Time Persistence of Superantigen-Producing Staphylococcus Aureus Strains in the Intenstinal Micoflora of Healthy Infants", Pediatric Research 48:741-747 (2000).

(Continued)

Primary Examiner — Laura L. Stockton

(57) ABSTRACT

Provided herein are compounds in accord with Formula I:

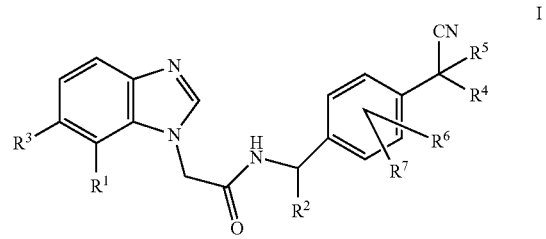

that are useful in the treatment of pain.

20 Claims, No Drawings

OTHER PUBLICATIONS

McDonnell, et al., 7-Hydroxynaphthalen-I-yt-Urea and -Amide Antagonists of Human Vanilloid Receptor 1'; Biororganic & Medicinal Chemistry Letters 14 (2004), pp. 531-534.

Musso, et al., "Indanylidenes. 1. Design and Synthesis of (E)-2-(4,6-Difluoro-1-indanylidene)acetamide, a Potent, Centrally Acting Muscle Relaxant with Antiinflammatory and Analgesic Activity"; J. Med. Chem. 2003, 46, pp. 399-408.

Patent Abstract of Japan, vol. 2000, No. 07, Sep. 29, 2000 & JP 2000 095767 A (Takeda Chem. Ind. Ltd), Apr. 4, 2000.

Rudin, et al., "Staphylococcal Enterotoxin B and High Dose Phytohemagglutinin Induce a Th1-Skewed Response in Neonates Irrespective of Atopic Status at 2 Years of Age", Scandinavin Journal of Immunology 52:415-461 (2000), Abstract Only.

Sasaki, et al., "Prevention of Collagen-Induced Arthritis with the Superantigen Staphylococcal Enterotoxin B", Pathophysiology 4:25-31 (1997).

Soos, et al., "Treatment of PL/J Mice with the Superantigen, Staphylococcal Enterotoxin B, Prevents Development of Experimental Allergic Encephalomyelitis", J. Neuroimmunology 43:39-44 (1993).

Willitzer, H., et al., "Synthese und Antivirale Wirsamkeit von Substituierten 5-Ureiod- und 5-Thioureidobenzimidazolderivaten" Pharmazie, VEB VERLAG VOLK und Gesundheit. Berlin, Germany vol. 33, No. 1, Jan. 1978, pp. 30-38, XP002209435 ISSN: 0031-7144 English Abstract is Cited as access No. 1978:424221.

STN International, File CAPLUS, Accession No, 1978:424221, Document No. 89:24221, Willitzer, et al., "Synthesis and antiviral Activity of Substituted 5-Ureiodo- and 5- Thioureidobenzimadazole Derivatives", & Pharmazie (1978), 33(1) 30-8.

STN Intl. File CAPLUS, Accession No. 1958:50566, Doc. No. 52-50566, Foster, R., "1-Ethyl-2-Methyl-5-Nitrobenzimidazole" & Journal of the Chem. Society, Abstracts (1957) 4687-8.

STN International, file CHEMCATS, Accession No. 2000:912544, Apr. 24, 2003, CHS 0297096, 1H-Benzimidazole-1-Acetamide, N-[3-Trifluoromethyl)Phenyl]-CAS Registry No. 294669-15-1.

STN International, file CHEMCATS, Accession No. 2000:532079, Apr. 23, 2003, BAS 0238979,1-H-Benzimidazole-1-Acetamide, N-(3-Chlorophenyl)-CAS Registry No. 116488-26-7.

STN International, file CHEMCATS, Accession No. 2001:10738, Apr. 24, 2003, NS11937, 1 H-Indole-3-Butanamide, N-(4-Methylphenyl)-CAS Registry No. 313550-48 0.

STN International, file CHEMCATS, Accession No. 2001:1505160, Apr. 29, 2003, AG-690/40696518,1H-Benzimidazole-I-Acetamide, N-(2,3-Dichlorophenyl)-, CAS Registry No. 332384-60-8.

STN International, file CHEMCATS, Accession No. 2002:2035573, Jul. 9, 2002, ASN 1816063,1H-Benzimidazole-1-Acetamide, N-(3-Chloro-4-Methylphenyl)-CAS Registry No. 332908-87-9.

STN International, file CHEMCATS, Accession No. 2002:2042451, Jul. 9, 2002, ASN 442844,1H-Benzimidazole-1-Acetamide, N-(5-Amino-2-Methylphenyl)—Cas Registry No. 436095-70-4.

STN Internationa, file CHEMCATS, Accession No. 2003:454497, Apr. 30, 2003, ASN 5212034,1H-Indole-3-Acetamide, N-(3,5-Dimethoxyphenyl)—CAS Registry No. 460336-68-9.

STN International, file CHEMCATS, Accession No. 2003:454500, Apr. 30, 2003, ASN 5212038,1 H-Indole-3-Acetamide, N-(3,5-Dimethoxyphenyl)—CAS Registry No. 460336-71-4.

STN International, file CHEMCATS, Accession No. 2003:1778448, Jul. 9, 2002, ASN 3067491,1 H-Benzimidazole-I-Acetamide, N-(2-Flurophenyl)—CAS Registry No. 483326-88-1.

STN International, file CHEMCATS, Accession No. 2003-1780032, Jul. 9, 2002, ASN 3110045, 1H-Benzimidazole-I-Acetamide, 5,6-Dimethyl-N-[2-(Trifluoromethyl) Phenyl]—CAS Registry No. 483347-09-7.

STN International, file CHEMCATS, Accession No. 2003:1780036, Jul. 9, 2002, ASN 3110053, 1 H-Benzimidazole-1-Acetamide, N-(2,4-Dimethoxyphenyl)-5,6-Dimethyl—CAS Registry No. 483347-12-2.

STN International, file CHEMCATS, Accession No. 2003:1780041, Jul. 9, 2002, ASN 3110088,1H-Benzimidazole-1-Acetamide, N-[4-(Dimethylamino)Phenyl]-5,6-Dimethyl- Cas Registry No. 483347-17-7.

STN International, file CHEMCATS, Accession No. 2003:1783073, Jul. 9, 2002, ASN 3212475, 1H-Benzimidazole-1-Acetamide, N-(3-Fluorophenyl)- CAS Registry No. 483978-05-8.

STN International, file CHEMCATS, Accession No. 2003:2842871, Apr. 23, 2003, BAS 5595011, 1H-Indole-3-Acetamide, N-(3-Fluoro-4-Methylphenyl)—CAS Registry No. 510764-85-9.

STN International, file CHEMCATS, Accession No. 2003:3562090, Apr. 30, 2003, ZT-5586656, 1H-Indole-3-Propanamide, N-[2-(I-Methylethyl)Phenyl]—CAS Registry No. 556791-23-2.

STN International, file CHEMCATS, Accession No. 2003:3425665, Apr. 30, 2003, ZT-2132403, 1H-Indole-3-Propanamide,N-[4-(1,1-Dimethylethyl)Phenyl]—CAS Registry No. 562052-38-4.

STN International, file CHEMCATS, Accession No. 2003:3428083, Apr. 30, 2003, ZT-2150185, 1H-Indole-3-Propanamide,N-(2-Chloro-4-Methylphenyl)- CAS Registry No. 562794-00-7.

STN International, file HCAPLUS, Accession No. 2002:737351, Document No. 138:265138, Olgen, Sureyya et al., Synthesisand Antioxidant Properties of Novel N-Substituted Indole-2-Carboxamide and Indole-3-Acetamide Derivatives, & Archiv der Pharmazie (Einheim, Germany) (2002), 335(7), 331-338.

STN International, Accession No. 2002:695939 Document No. 137:232452, Rotta Research Laboratorium S.p. A., "Preparation of Benzamidines Having Antiinflammatory & Immunosuppressive Activity" & WO2002070468, A2, 20020912, 2002.

STN International, file HCAPLUS, Accession No. 2000:214835, Document No. 132:265201, Takeda Chemical Industries LTD., "Preparation of Imidazole Derivatives as Gonadotropin-Releasing Hormone Antogonists" & JP A2,200095767, 20000404, 2000.

STN International, file HCAPLUS, Accession No. 2000:825244, Document No. 134:147129, Jamieson, Craig, et al., "A Rapid approach for the Optimization of Polymer Support Reagents in Synthesis", & Synlett (2000), (11), 1603-1607.

STN International, file HCAPLUS, Accession No. 1988:610992, Document No. 109:210992, shah, V.H., et al., "Studies on acetamide Derivatives, Part-II. Preparation, Antimicrobial and Anthelmintic Activity of N-Arylaminocetyl-Benzimidazole/Sulfadiazine or Sulfamethazine and N-Arylbenzimidazole-1-yl/Sulfadizin-4Yl or Sulfamethazin-4-Yl/Acetamides", & Journal of the Indian Chemical Society (1987), 64(11), 678-81.

STN International, file HCAPLUS, Accession No. 1958:31856, Document No. 52:31856, Cacace, Fulvio, et al., "Benzimidazole-N-Acetic Acid and its Growth Activity", & Atti Accad. Nazl. Lincei. Rend., Classe Sci. Fiz. Mat e Nat 1957), 22, 510-13", 1958.

STN International, file HCAPLUS, Accession No. 1993:102385, Document No. 118:102385, Gallant, Michel et al., "A Steroselective Synthesis of Indole-Beta-N-Glycosides: an Application to the Syntehsis of Rebeccamycin", & Jr. of Organic Chemistry (1993), 58(2), 343-9.

STN International, file HCAPLUS, Accession No. 1998:227318, Document No. 128:308402, Sanwa Kagaku Kenkyusho Co., Ltd., "Preparation of N-(Diisopropylphenyl)Quinolineacetamides as Antiarterioscleroties", & JP, A2, 10095766, 19980414", 1998.

STN International, file HCAPLUS, Accession No. 1995:594439, Document No. 123:9266, Interneuron Pharm, Inc., "Substituted Tryptamines, Phenalkylamines and Related Compounds", & US, A, 5403851, 19950404.

STN International CAPLUS Access No. 1967:46373, Doc. No. 66:46373, Takahashi, S., et al., "Benzimidazole N-Oxides . . . Reactivity . . . 3 Oxide" & Che. & Pharm. Bulletin (1966), 14(11, 1219-27.

STN Intl. File CAPLUS, Access No. 1969:492626, Doc. No. 71:92626, Osman, M.A., "Benzimidazole Derivatives . . . and Coupling Components", & K. Ertesito (1969) 11(5-6), 118-21.

STN International CAPLUS, Access No. 1966:51996.

STN International, File Registry, See RN 743444-08-8, Sep. 13, 2004.

STN International, File Registry (Chemcats), compounds with Reg. Nos. 499119-26-5, 498538-36-6, 498535-73-2, 497242-15-6, 494202-99-2, 488804-38-2, 488095-08-5, 476326-10-0, 476325-77-6, 476281-13-7, 476279-49-9, 476275-91-9, 391218-48-7, 380905-60-2, 377757-95-4, 364625-75-2, 364054-61-5, 335397-26-7, 335397-24-5, 332899,59-9, 331840-20-1, 330466-04-1, 327971-85-7, 318512-58-2, 313535-67-0, 313509-05-6, 313508-99-5, 313367-

31-6, 313275-92-2, 313275-91-1, 313275-90-0, 313275-89-7, 313275-88-6, 313275-87-5, 313241-54-2, 313241-53-1, 299927-16-5, and 292842-87-6.

Caterina, et al., "The Capsaicin Receptor: A Heat-Activated Ion Channel in the Pain Pathway"; Nature, vol. 389, 1997, pp. 816-824 (1997).

Collins, et al., "Mucosal Tolerance to a Bacterial Superantigen Indicates a Novel AJ Toxic Shock", Infection and Immunity 70:2282-2287 (2002).

Gallard, et al., "New N-Pyridinyl (Methyl)-N1-Substituted . . . Systemic Anti-Inflammatory Agents", Journal of Enzyme Inhibition and Medicinal Chemistry, vol. 18, No. 2, pp. 201-208, (2003).

T.L. Gilchrist, "Heterocyclic Chemistry", 2nd Edition, Longman Scientific and Technical, pp. 248-282 (1992).

Hwang, et al., "Hot Channels in Airways: Pharmacology of the Vanilloid Receptor"; Curr. Opin. Pharmacol., vol. 3, pp. 235-242 (2002).

Rashid, et al., "Novel Expression of Vanilloid . . . in Neuropathic Pain"; J. Pharmacol. Exp. Ther., vol. 304, No. 3, pp. 940-948 (2003).

Szallasi, et al., "Vanilloid (Capsaicin) Receptors in Health and Disease"; Am. J. Clin. Pathol. vol. 118, pp. 110-121 (2002).

Tominaga, et al., "The Cloned Capsaicin Receptor Integrates Multiple Pain-Producing Stiluli"; Neuron, vol. 21, pp. 531-543 (1998).

Walker, et al., "The VR1 Antagonist Capsazepine Reverses Mechanical Hyperalgesia in Models of Inflammatory and Neuropathic Pain"; J. Pharmacol. Exp. Ther., vol. 304, pp. 56-62 (2003).

Yiangou, et al., "Capsaicin Receptor VR1 and ATP-Gated Ion Channel P2X3, in Human Urinary Bladder"; BJU International, vol. 87, pp. 774-779 (2001).

Non-Final Office Action mailed on Jan. 7, 2008, for U.S. Appl. No. 10/556,229, AstraZeneca Ref. No. 101062-1P US.

Non-Final Office Action mailed on Jul. 16, 2007, for U.S. Appl. No. 10/556,229, AstraZeneca Ref. No. 101062-1P US.

Non-Final Office Action mailed on May 16, 2008, for Application No. 10/557,806, AstraZeneca Reference No. 101101-1P US.

Non-Final Office Action mailed on Jul. 23, 2008 for Application No. 10/557,806, AstraZeneca Reference No, 101101-1P US.

Co-pending U.S. Appl. No. 11/614,346, filed Dec. 21, 2006.

* cited by examiner

BENZIMIDAZOLE DERIVATIVES

RELATED APPLICATIONS

This application is a divisional application of U.S. patent application Ser. No. 11/836,221, filed Aug. 9, 2007, which claims priority to U.S. Provisional Patent Application Ser. No. 60/837,249, filed Aug. 11, 2006.

FIELD OF THE INVENTION

The present invention relates to new compounds, to pharmaceutical compositions containing said compounds and to the use of said compounds in therapy. The present invention further relates to processes for the preparation of said compounds and to new intermediates used in the preparation thereof.

BACKGROUND OF THE INVENTION

Pain sensation in mammals is due to the activation of the peripheral terminals of a specialized population of sensory neurons known as nociceptors. Capsaicin, the active ingredient in hot peppers, produces sustained activation of nociceptors and also produces a dose-dependent pain sensation in humans. Cloning of the vanilloid receptor 1 (VR1 or TRPV1) demonstrated that VR1 is the molecular target for capsaicin and its analogues. (Caterina, M. J., Schumacher, M. A., et. al. Nature (1997) v.389 p 816-824). Functional studies using VR1 indicate that it is also activated by noxious heat, tissue acidification and other inflammatory mediators (Tominaga, M., Caterina, M. J. et. al. Neuron (1998) v.21, p. 531-543). Expression of VR1 is also regulated after peripheral nerve damage of the type that leads to neuropathic pain. These properties of VR1 make it a highly relevant target for pain and for diseases involving inflammation. While agonists of the VR1 receptor can act as analgesics through nociceptor destruction, the use of agonists, such as capsaicin and its analogues, is limited due to their pungency, neurotoxicity and induction of hypothermia. Instead, agents that block the activity of VR1 should prove more useful. Antagonists would maintain the analgesic properties, but avoid pungency and neurotoxicity side effects.

Compounds with VR1 inhibitor activity are believed to be of potential use for the treatment and/or prophylaxis of disorders such as pain, especially that of inflammatory or traumatic origin such as arthritis, ischaemia, cancer, fibromyalgia, low back pain and post-operative pain (Walker et al J Pharmacol Exp Ther. (2003) January; 304(1):56-62). In addition to this visceral pains such as chronic pelvic pain, cystitis, irritable bowel syndrome (IBS), pancreatitis and the like, as well as neuropathic pain such as sciatia, diabetic neuropathy, HIV neuropathy, multiple sclerosis, and the like (Walker et al ibid, Rashid et al J Pharmacol Exp Ther. (2003) March; 304 (3):940-8), are potential pain states that could be treated with VR1 inhibition. These compounds are also believed to be potentially useful for inflammatory disorders like asthma, cough, and inflammatory bowel disease (IBD) (Hwang and Oh Curr Opin Pharmacol (2002) June; 2(3):235-42). Compounds with VR1 blocker activity are also useful for itch and skin diseases like psoriasis and for gastro-esophageal reflux disease (GERD), emesis, cancer, urinary incontinence and hyperactive bladder (Yiangou et al BJU Int (2001) June; 87(9):774-9, Szallasi Am J Clin Pathol (2002) 118: 110-21). VR1 inhibitors are also of potential use for the treatment and/or prophylaxis of the effects of exposure to VR1 activators like capsaicin or tear gas, acids or heat (Szallasi ibid).

A further potential use relates to the treatment of tolerance to VR1 activators.

VR1 inhibitors may also be useful in the treatment of interstitial cystitis and pain related to interstitial cystitis.

WO2004/100865 discloses compounds exhibiting inhibitory activity at the vanilloid receptor 1 (VR1).

DEFINITIONS

If used herein, the following terms have the following meanings:

The term "(+,−)" shall mean the racemic mixture of such compound.

The term "alkyl" used alone or as a suffix or prefix, refers to straight or branched chain hydrocarbyl radicals comprising 1 to about 12 carbon atoms.

The term "alkylene" used alone or as suffix or prefix, refers to divalent straight or branched chain hydrocarbon radicals comprising 1 to about 12 carbon atoms, which serves to links two structures together.

The term "alkenyl" used alone or as suffix or prefix, refers to a monovalent straight or branched chain hydrocarbon radical having at least one carbon-carbon double bond and comprising at least 2 and up to about 12 carbon atoms.

The term "alkynyl" used alone or as suffix or prefix, refers to a monovalent straight or branched chain hydrocarbon radical having at least one carbon-carbon triple bond and comprising at least 2 and up to about 12 carbon atoms.

The term "amine" or "amino" refers to radicals of the general formula —NRR', wherein R and R' are independently selected from hydrogen or a hydrocarbyl radical.

The term "aromatic" refers to hydrocarbyl radicals having one or more polyunsaturated carbon rings having aromatic character, (e.g., 4n+2 delocalized electrons) and comprising 6 up to about 14 carbon atoms.

The term "aryl" used alone or as suffix or prefix, refers to a hydrocarbon radical having one or more polyunsaturated carbon rings having aromatic character, (e.g., 4n+2 delocalized electrons) and comprising 5 up to about 14 carbon atoms, wherein the radical is located on a carbon of the aromatic ring.

The term "cycloalkyl," used alone or as suffix or prefix, refers to a monovalent ring-containing hydrocarbon radical comprising at least 3 up to about 12 carbon atoms.

The term "heterocycloalkyl" refers to a saturated or unsaturated cycloalkyl in which at least one ring carbon (and any associated hydrogen atoms) are independently replaced with at least one heteroatom selected from O and N. Such cycloalkyls include, but are not limited to, groups such as morpholinyl, piperidinyl, piperazinyl, and pyrrolidinyl.

The term "halo" or "halogen" refers to fluorine, chlorine, bromine and iodine radicals.

The term "heterocycle" or "heterocyclic" or "heterocyclic moiety" refers to ring-containing monovalent and divalent radicals having one or more heteroatoms, independently selected from N, O, P and S, as part of the ring structure and comprising at least 3 and up to about 20 atoms in the rings preferably 5 and 6 membered rings. Heterocyclic moieties may be saturated or unsaturated, containing one or more double bonds, and heterocyclic moieties may contain more than one ring.

The term "heteroaryl" refers to heterocyclic monovalent and divalent radicals having aromatic character.

Heterocyclic moieties include for example monocyclic moieties such as: aziridine, oxirane, thiirane, azetidine, oxetane, thietane, pyrrolidine, pyrroline, imidazolidine, pyrazolidine, dioxolane, sulfolane 2,3-dihydrofuran, 2,5-dihydrofuran tetrahydrofuran, thiophane, thiophene, piperidine, 1,2,3, 6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide. In addition heterocyclic moieties include heteroaryl rings such as: pyridyl, pyrazinyl, pyrimidinyl, pyridazinyl, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl. Additionally, heterocyclic moieties encompass polycyclic moieties such as: indole, indoline, quinoline, tetrahydroquinoline, isoquinoline, tetrahydroisoquinoline, 1,4-benzodioxan, coumarin, dihydrocoumarin, benzofuran, 2,3-dihydrobenzofuran, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocyclic moieties include polycyclic heterocyclic moieties wherein the ring fusion between two or more rings comprises more than one bond common to both rings and more than two atoms common to both rings. Examples of such bridged heterocycles include quinuclidine, diazabicyclo[2.2.1]heptane and 7-oxabicyclo[2.2.1]heptane.

The term "hydrocarbyl" refers to any structure comprising only carbon and hydrogen atoms up to 14 carbon atoms.

The term "mammal" includes any of various warm-blooded vertebrate animals of the class Mammalia, including but not limited to humans, generally characterized by a covering of hair on the skin.

The term "patient" refers to one who receives medical attention, care, or treatment.

DETAILED DESCRIPTION OF THE INVENTION

One embodiment of the invention is a compound of Formula I:

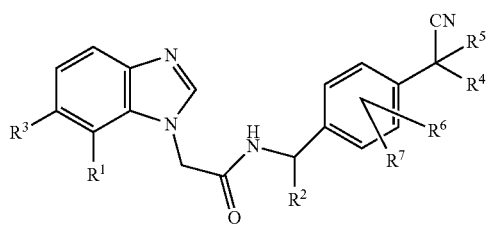

wherein:
$R^1$ is selected from CN, halogen, C(=O)CH$_3$;
$R^2$ is selected from methyl or H;
$R^3$ is selected from H, or halogen;
$R^4$ and $R^5$ are each independently selected from methyl or ethyl or $R^4$ and $R^5$ together with the carbon atom to which they are attached form a 3-6 membered cycloalkyl or a 5 or 6 membered heterocycloalkyl group;
$R^6$ and $R^7$ are each independently selected from H, halogen, methyl, or ethyl;
or a pharmaceutically acceptable salt thereof;
wherein the compound of Formula I is not
N-[4-(1-cyano-1-methylethyl)benzyl]-2-(6,7-difluoro-1H-benzimidazol-1-yl)-acetamide;

2-(7-chloro-1H-benzimidazol-1-yl)-N-[4-(1-cyano-1-methylethyl)-3-fluorobenzyl]acetamide;
(+)-2-(7-cyano-1H-benzimidazol-1-yl)-N-{1-[4-(1-cyanocyclohexyl)phenyl]ethyl}acetamide;
(+)-N-{1-[4-(1-cyano-1-methylethyl)-2-methylphenyl]ethyl}-2-(6,7-difluoro-1H-benzimidazol-1-yl)acetamide;
(+,-)-2-(6-chloro-7-fluoro-1H-benzimidazol-1-yl)-N-{1-[4-(1-cyano-1-methylethyl)-2-methylphenyl]ethyl}acetamide;
(+)-2-(7-acetyl-1H-benzimidazol-1-yl)-N-{1-[4-(1-cyano-1-methylethyl)phenyl]ethyl}acetamide;
(+)-N-{1-[4-(1-cyanocyclohexyl)phenyl]ethyl}-2-(6,7-difluoro-1H-benzimidazol-1-yl)acetamide;
(+)-2-(7-chloro-6-fluoro-1H-benzimidazol-1-yl)-N-{1-[4-(1-cyano-1-methylethyl)-3-fluorophenyl]ethyl}acetamide;
(+)-N-{1-[4-(1-cyano-1-methylethyl)-3-fluorophenyl]ethyl}-2-(6,7-difluoro-1H-benzimidazol-1-yl)acetamide;
(+)-N-{1-[4-(1-cyanocyclobutyl)phenyl]ethyl}-2-(6,7-difluoro-1H-benzimidazol-1-yl)acetamide;
(R)(+)-N-{1-[4-(1-cyano-1-methylethyl)phenyl]ethyl}-2-(6,7-difluoro-1H-benzimidazol-1-yl)acetamide;
(R)(+)-2-(7-cyano-1H-benzimidazol-1-yl)-N-{1-[4-(1-cyano-1-methylethyl)phenyl]ethyl}acetamide;
(+)-2-(7-cyano-1H-benzimidazol-1-yl)-N-{1-[4-(1-cyano-1-methylethyl)-3-fluorophenyl]ethyl}acetamide;
(+)-2-(7-acetyl-1H-benzimidazol-1-yl)-N-{1-[4-(1-cyano-1-methylethyl)-3-fluorophenyl]ethyl}acetamide;
(R)(+)-N-{1-[4-(1-cyano-1-ethylpropyl)phenyl]ethyl}-2-(6,7-difluoro-1H-benzimidazol-1-yl)acetamide.

One embodiment of the invention is a compound of Formula I or a pharmaceutically acceptable salt thereof, wherein $R^1$ is independently selected from chlorine or fluorine.

One embodiment of the invention is a compound of Formula I or a pharmaceutically acceptable salt thereof, wherein $R^3$ is selected from chlorine or fluorine.

One embodiment of the invention is a compound of Formula I or a pharmaceutically acceptable salt thereof, wherein $R^1$ is independently selected from chlorine or fluorine, and $R^3$ is selected from chlorine or fluorine.

One embodiment of the invention is a compound of Formula I or a pharmaceutically acceptable salt thereof, wherein $R^4$ and $R^5$ are independently selected from methyl or ethyl.

One embodiment of the invention is a compound of Formula I or a pharmaceutically acceptable salt thereof, wherein $R^1$ is independently selected from chlorine or fluorine and $R^4$ and $R^5$ are independently selected from methyl or ethyl.

One embodiment of the invention is a compound of Formula I or a pharmaceutically acceptable salt thereof, wherein $R^3$ is selected from chlorine or fluorine and $R^4$ and $R^5$ are independently selected from methyl or ethyl.

One embodiment of the invention is a compound of Formula I or a pharmaceutically acceptable salt thereof, wherein $R^1$ is independently selected from chlorine or fluorine, $R^3$ is selected from chlorine or fluorine, and $R^4$ and $R^5$ are independently selected from methyl or ethyl.

One embodiment of the invention is a compound of Formula I or a pharmaceutically acceptable salt thereof, wherein $R^4$ and $R^5$ together with the carbon atom to which they are attached form a 3, 4, or 6 membered cycloalkyl or a 5 or 6 membered heterocycloalkyl group.

One embodiment of the invention is a compound of Formula I or a pharmaceutically acceptable salt thereof, wherein $R^1$ is independently selected from chlorine or fluorine and $R^4$ and $R^5$ together with the carbon atom to which they are attached form a 3, 4, or 6 membered cycloalkyl or a 5 or 6 membered heterocycloalkyl group.

One embodiment of the invention is a compound of Formula I or a pharmaceutically acceptable salt thereof, wherein $R^3$ is selected from chlorine or fluorine, and $R^4$ and $R^5$ together with the carbon atom to which they are attached form a 3, 4, or 6 membered cycloalkyl or a 5 or 6 membered heterocycloalkyl group.

One embodiment of the invention is a compound of Formula I or a pharmaceutically acceptable salt thereof, wherein $R^1$ is independently selected from chlorine or fluorine, $R^3$ is selected from chlorine or fluorine, and $R^4$ and $R^5$ together with the carbon atom to which they are attached form a 3, 4, or 6 membered cycloalkyl or a 5 or 6 membered heterocycloalkyl group.

One embodiment of the invention is a compound of Formula I or a pharmaceutically acceptable salt thereof, wherein $R^6$ and $R^7$ are each independently selected from fluorine or chlorine.

One embodiment of the invention is a compound of Formula I or a pharmaceutically acceptable salt thereof, wherein $R^6$ and $R^7$ are each independently selected from H.

One embodiment of the invention is a compound of Formula I or a pharmaceutically acceptable salt thereof, wherein $R^1$ is independently selected from chlorine or fluorine and $R^6$ and $R^7$ are each independently selected from H.

One embodiment of the invention is a compound of Formula I or a pharmaceutically acceptable salt thereof, wherein $R^3$ is selected from chlorine or fluorine and $R^6$ and $R^7$ are each independently selected from H.

One embodiment of the invention is a compound of Formula I or a pharmaceutically acceptable salt thereof, wherein $R^1$ is independently selected from chlorine or fluorine, $R^3$ is selected from chlorine or fluorine, and $R^6$ and $R^7$ are each independently selected from H.

One embodiment of the invention is a compound of Formula I or a pharmaceutically acceptable salt thereof, wherein $R^4$ and $R^5$ are independently selected from methyl or ethyl and $R^6$ and $R^7$ are each independently selected from H.

One embodiment of the invention is a compound of Formula I or a pharmaceutically acceptable salt thereof, wherein $R^1$ is independently selected from chlorine or fluorine, $R^4$ and $R^5$ are independently selected from methyl or ethyl, and $R^6$ and $R^7$ are each independently selected from H.

One embodiment of the invention is a compound of Formula I or a pharmaceutically acceptable salt thereof, wherein $R^3$ is selected from chlorine or fluorine, $R^4$ and $R^5$ are independently selected from methyl or ethyl, and $R^6$ and $R^7$ are each H.

One embodiment of the invention is a compound of Formula I or a pharmaceutically acceptable salt thereof, wherein $R^1$ is independently selected from chlorine or fluorine, $R^3$ is selected from chlorine or fluorine, $R^4$ and $R^5$ are independently selected from methyl or ethyl, and $R^6$ and $R^7$ are each H.

One embodiment of the invention is a compound of Formula I or a pharmaceutically acceptable salt thereof, wherein $R^4$ and $R^5$ together with the carbon atom to which they are attached form a 3, 4, or 6 membered cycloalkyl or a 5 or 6 membered heterocycloalkyl group and $R^6$ and $R^7$ are each H.

One embodiment of the invention is a compound of Formula I or a pharmaceutically acceptable salt thereof, wherein $R^1$ is independently selected from chlorine or fluorine, $R^4$ and $R^5$ together with the carbon atom to which they are attached form a 3, 4, or 6 membered cycloalkyl or a 5 or 6 membered heterocycloalkyl group, and $R^6$ and $R^7$ are each H.

One embodiment of the invention is a compound of Formula I or a pharmaceutically acceptable salt thereof, wherein $R^3$ is selected from chlorine or fluorine, $R^4$ and $R^5$ together with the carbon atom to which they are attached form a 3, 4, or 6 membered cycloalkyl or a 5 or 6 membered heterocycloalkyl group, and $R^6$ and $R^7$ are each H.

One embodiment of the invention is a compound of Formula I or a pharmaceutically acceptable salt thereof, wherein $R^1$ is independently selected from chlorine or fluorine, $R^3$ is selected from chlorine or fluorine, $R^4$ and $R^5$ together with the carbon atom to which they are attached form a 3, 4, or 6 membered cycloalkyl or a 5 or 6 membered heterocycloalkyl group, and $R^6$ and $R^7$ are each H.

One embodiment of the invention is a compound selected from:
(S)(−)-2-(7-Cyano-1H-benzimidazol-1-yl)-N-{1-[4-(1-cyano-1-methylethyl)phenyl]ethyl}acetamide;
(S)(−)-N-{1-[4-(1-Cyano-1-methylethyl)phenyl]ethyl}-2-(7-fluoro-1H-benzimidazol-1-yl)acetamide;
(S)(−)-N-{1-[4-(1-Cyano-1-methylethyl)phenyl]ethyl}-2-(7-chloro-1H-benzimidazol-1-yl)acetamide;
(S)(−)-N-{1-[4-(1-Cyano-1-ethylpropyl)phenyl]ethyl}-2-(6,7-difluoro-1H-benzimidazol-1-yl)acetamide;
(−)-N-{1-[4-(1-Cyanocyclobutyl)phenyl]ethyl}-2-(6,7-difluoro-1H-benzimidazol-1-yl)acetamide;
(−)-N-{1-[4-(1-Cyanocyclohexyl)phenyl]ethyl}-2-(6,7-difluoro-1H-benzimidazol-1-yl)acetamide;
(−)-2-(7-Cyano-1H-benzimidazol-1-yl)-N-{1-[4-(1-cyanocyclohexyl)phenyl]ethyl}acetamide;
(−)-2-(7-Cyano-1H-benzimidazol-1-yl)-N-{1-[4-(1-cyanocyclobutyl)phenyl]ethyl}acetamide;
(−)-2-(7-Acetyl-1H-benzimidazol-1-yl)-N-{1-[4-(1-cyano-1-methylethyl)phenyl]ethyl}acetamide;
(S)(−)-2-(7-Acetyl-1H-benzimidazol-1-yl)-N-{1-[4-(1-cyano-1-methylethyl)-3-fluorophenyl]ethyl}acetamide;
(−)-N-{1-[4-(1-cyano-1-methylethyl)-3-fluorophenyl]ethyl}-2-(6,7-difluoro-1H-benzimidazol-1-yl)acetamide;
(−)-2-(7-chloro-1H-benzimidazol-1-yl)-N-{1-[4-(1-cyano-1-methylethyl)-3-fluorophenyl]ethyl}acetamide;
(−)-2-(7-Cyano-1H-benzimidazol-1-yl)-N-[4-(1-cyano-1-methylethyl)-3-fluorobenzyl]acetamide;
(−) 2-(7-chloro-6-fluoro-1H-benzimidazol-1-yl)-N-{1-[4-(1-cyano-1-methylethyl)-3-fluorophenyl]ethyl}acetamide;
(−)-2-(7-Chloro-6-fluoro-1H-benzimidazol-1-yl)-N-{1-[4-(1-cyano-1-methylethyl)-3-methylphenyl]ethyl}acetamide;
(−)-2-(7-Chloro-6-fluoro-1H-benzimidazol-1-yl)-N-{1-[4-(1-cyano-1-methylethyl)-3-methylphenyl]ethyl}acetamide;
(−) N-{1-[4-(4-cyanotetrahydro-2H-thiopyran-4-yl)-2-methylphenyl]ethyl}-2-(6,7-difluoro-1H-benzimidazol-1-yl)acetamide;
(−)-N-{1-[4-(1-cyano-1-methylethyl)-2-methylphenyl]ethyl}-2-(6,7-difluoro-1H-benzimidazol-1-yl)acetamide;
(−)-N-{1-[4-(1-cyano-1-methylethyl)-2-methylphenyl]ethyl}-2-(6,7-difluoro-1H-benzimidazol-1-yl)acetamide;
(−)-N-{1-[4-(1-cyano-1-methylethyl)-2-methylphenyl]ethyl}-2-(7-fluoro-1H-benzimidazol-1-yl)acetamide;
(−)-N-{1-[3-Chloro-4-(1-cyano-1-methylethyl)phenyl]ethyl}-2-(6,7-difluoro-1H-benzimidazol-1-yl)acetamide;
(−)-N-{1-[3-Chloro-4-(1-cyano-1-methylethyl)phenyl]ethyl}-2-(7-cyano-1H-benzimidazol-1-yl)acetamide;
(−)-2-(6,7-Difluoro-1H-benzimidazol-1-yl)-N-{1-[4-(1-cyano-1-methylethyl)-3-methylphenyl]ethyl}acetamide;
(−)-2-(7-Cyano-1H-benzimidazol-1-yl)-N-{1-[4-(1-cyano-1-methylethyl)-3-methylphenyl]ethyl}acetamide;
(S)(−)-2-(6-chloro-7-fluoro-1H-benzimidazol-1-yl)-N-{[4-(1-cyano-1-methylethyl)phenyl]ethyl}acetamide;
and a pharmaceutically acceptable salt thereof.

One embodiment of the invention is a compound selected from:
- (+,−)-2-(7-Cyano-1H-benzimidazol-1-yl)-N-{1-[4-(1-cyano-1-methylethyl)phenyl]ethyl}acetamide;
- (+,−)-N-{1-[4-(1-Cyano-1-methylethyl)phenyl]ethyl}-2-(6,7-difluoro-1H-benzimidazol-1-yl)acetamide;
- (+,−)-N-{1-[4-(1-Cyano-1-methylethyl)phenyl]ethyl}-2-(7-fluoro-1H-benzimidazol-1-yl)acetamide;
- (+,−)-N-{1-[4-(1-Cyano-1-methylethyl)phenyl]ethyl}-2-(7-chloro-1H-benzimidazol-1-yl)acetamide;
- (+,−)-N-{1-[4-(1-Cyano-1-ethylpropyl)phenyl]ethyl}-2-(6,7-difluoro-1H-benzimidazol-1-yl)acetamide;
- (+,−)-N-{1-[4-(1-Cyanocyclobutyl)phenyl]ethyl}-2-(6,7-difluoro-1H-benzimidazol-1-yl)acetamide;
- (+,−)-N-{1-[4-(1-Cyanocyclohexyl)phenyl]ethyl}-2-(6,7-difluoro-1H-benzimidazol-1-yl)acetamide;
- (+,−)-2-(7-Cyano-1H-benzimidazol-1-yl)-N-{1-[4-(1-cyanocyclohexyl)phenyl]ethyl}acetamide;
- (+,−)-2-(7-Cyano-1H-benzimidazol-1-yl)-N-{1-[4-(1-cyanocyclopropyl)phenyl]ethyl}acetamide;
- (+,−)-2-(7-Cyano-1H-benzimidazol-1-yl)-N-{1-[4-(1-cyanocyclobutyl)phenyl]ethyl}acetamide;
- (+,−)-2-(7-Acetyl-1H-benzimidazol-1-yl)-N-{1-[4-(1-cyano-1-methylethyl)phenyl]ethyl}acetamide;
- (+,−)-2-(7-Acetyl-1H-benzimidazol-1-yl)-N-{1-[4-(1-cyano-1-methylethyl)-3-fluorophenyl]ethyl}acetamide
- (+,−)-2-(7-Cyano-1H-benzimidazol-1-yl)-N-{1-[4-(1-cyano-1-methylethyl)-3-fluorophenyl]ethyl}acetamide;
- (+,−)-2-(7-chloro-6-fluoro-1H-benzimidazol-1-yl)-N-{1-[4-(1-cyano-1-methylethyl)phenyl]ethyl}acetamide;
- (+,−) 2-(7-chloro-6-fluoro-1H-benzimidazol-1-yl)-N-{1-[4-(1-cyano-1-methylethyl)-3-fluorophenyl]ethyl}acetamide;
- (+,−)-2-(7-Chloro-6-fluoro-1H-benzimidazol-1-yl)-N-{1-[4-(1-cyano-1-methylethyl)-3-methylphenyl]ethyl}acetamide;
- (+,−)-2-(7-Chloro-6-fluoro-1H-benzimidazol-1-yl)-N-{1-[4-(1-cyano-1-methylethyl)-3-methylphenyl]ethyl}acetamide;
- (+,−) N-{1-[4-(4-cyanotetrahydro-2H-thiopyran-4-yl)-2-methylphenyl]ethyl}-2-(6,7-difluoro-1H-benzimidazol-1-yl)acetamide;
- N-[4-(1-cyano-1-methylethyl)-2-methylbenzyl]-2-(6,7-difluoro-1H-benzimidazol-1-yl)acetamide
- 2-(7-cyano-1H-benzimidazol-1-yl)-N-[4-(1-cyano-1-methylethyl)-2-methylbenzyl]acetamide;
- (+,−)-N-{1-[4-(1-cyano-1-methylethyl)-2-methylphenyl]ethyl}-2-(6,7-difluoro-1H-benzimidazol-1-yl)acetamide;
- (+,−)-N-{1-[4-(1-cyano-1-methylethyl)-2-methylphenyl]ethyl}-2-(7-fluoro-1H-benzimidazol-1-yl)acetamide
- (+,−)-N-{1-[3-Chloro-4-(1-cyano-1-methylethyl)phenyl]ethyl}-2-(6,7-difluoro-1H-benzimidazol-1-yl)acetamide;
- (+,−)-N-{1-[3-Chloro-4-(1-cyano-1-methylethyl)phenyl]ethyl}-2-(7-cyano-1H-benzimidazol-1-yl)acetamide;
- (+,−)-2-(7,6-Difluoro-1H-benzimidazol-1-yl)-N-{1-[4-(1-cyano-1-methylethyl)-3-methylphenyl]ethyl}acetamide;
- (+,−)-2-(7-Cyano-1H-benzimidazol-1-yl)-N-{1-[4-(1-cyano-1-methylethyl)-3-methylphenyl]ethyl}acetamide;
- 2-(6-chloro-7-fluoro-1H-benzimidazol-1-yl)-N-{[4-(1-cyano-1-methylethyl)-2-methylbenzyl]acetamide;

and pharmaceutically acceptable salts thereof.

One embodiment of the invention is the compound (S)(−)-2-(7-chloro-6-fluoro-1H-benzimidazol-1-yl)-N-{1-[4-(1-cyano-1-methylethyl)phenyl]ethyl}acetamide and a pharmaceutically acceptable salt thereof.

One embodiment of the invention is the compound (S)(−)-N-{1-[4-(1-Cyano-1-methylethyl)phenyl]ethyl}-2-(6,7-difluoro-1H-benzimidazol-1-yl)acetamide and a pharmaceutically acceptable salt thereof.

One embodiment of the invention is a compound according of Formula I or a pharmaceutically acceptable salt thereof for use in the treatment of chronic nociceptive pain disorders in a mammal.

One embodiment of the invention is a compound of Formula I or a pharmaceutically acceptable salt thereof for use in the treatment of osteoarthritis.

One embodiment of the invention is a compound of Formula I or a pharmaceutically acceptable salt thereof for use in the treatment of chronic tendinitis.

One embodiment of the invention is a compound of Formula I or a pharmaceutically acceptable salt thereof for use in the treatment of pelvic pain.

One embodiment of the invention is a compound of Formula I or a pharmaceutically acceptable salt thereof for use in the treatment of peripheral neuropathy (primarily PHN).

One embodiment of the invention is a compound of Formula I or a pharmaceutically acceptable salt thereof for use in the treatment of gastroesophageal reflux disease (GERD), One embodiment of the invention is a compound of Formula I or a pharmaceutically acceptable salt thereof for use in the treatment of Irritable Bowel Syndrome (IBS).

One embodiment of the invention is a compound of Formula I or a pharmaceutically acceptable salt thereof for use in the treatment of overactive bladder.

One embodiment of the invention is a method of treating nociceptive pain disorders comprising administering an effective amount of a compound of Formula I or a pharmaceutically acceptable salt thereof to a patient in need thereof.

One embodiment of the invention is a method of treating nociceptive pain disorders comprising administering an effective amount of the compound (S)(−)-2-(7-chloro-6-fluoro-1H-benzimidazol-1-yl)-N-{1-[4-(1-cyano-1-methylethyl)phenyl]ethyl}acetamide or a pharmaceutically acceptable salt thereof to a patient in need thereof.

One embodiment of the invention is a method of treating nociceptive pain disorders comprising administering an effective amount of the compound (S)(−)-N-{1-[4-(1-Cyano-1-methylethyl)phenyl]ethyl}-2-(6,7-difluoro-1H-benzimidazol-1-yl)acetamide or a pharmaceutically acceptable salt thereof to a patient in need thereof.

One embodiment of the invention is a method of treating chronic nociceptive pain disorders comprising administering an effective amount of a compound of Formula I or a pharmaceutically acceptable salt thereof to a patient in need thereof.

One embodiment of the invention is a method of treating chronic nociceptive pain disorders comprising administering an effective amount of the compound (S)(−)-2-(7-chloro-6-fluoro-1H-benzimidazol-1-yl)-N-{1-[4-(1-cyano-1-methylethyl)phenyl]ethyl}acetamide or a pharmaceutically acceptable salt thereof to a patient in need thereof.

One embodiment of the invention is a method of treating chronic nociceptive pain disorders comprising administering an effective amount of the compound (S)(−)-N-{1-[4-(1-Cyano-1-methylethyl)phenyl]ethyl}-2-(6,7-difluoro-1H-benzimidazol-1-yl)acetamide or a pharmaceutically acceptable salt thereof to a patient in need thereof.

One embodiment of the invention is a method of treating osteoarthritis comprising administering an effective amount of a compound of Formula I or a pharmaceutically acceptable salt thereof to a patient in need thereof.

One embodiment of the invention is a method of treating osteoarthritis comprising administering an effective amount of the compound (S)(−)-2-(7-chloro-6-fluoro-1H-benzimidazol-1-yl)-N-{1-[4-(1-cyano-1-methylethyl)phenyl]ethyl}acetamide or a pharmaceutically acceptable salt thereof to a patient in need thereof.

One embodiment of the invention is a method of treating osteoarthritis comprising administering an effective amount of the compound (S)(−)-N-{1-[4-(1-Cyano-1-methylethyl)phenyl]ethyl}-2-(6,7-difluoro-1H-benzimidazol-1-yl)acetamide or a pharmaceutically acceptable salt thereof to a patient in need thereof.

One embodiment of the invention is a method of treating chronic tendinitis comprising administering an effective amount of a compound of Formula I or a pharmaceutically acceptable salt thereof to a patient in need thereof.

One embodiment of the invention is a method of treating chronic tendinitis comprising administering an effective amount of the compound (S)(−)-2-(7-chloro-6-fluoro-1H-benzimidazol-1-yl)-N-{1-[4-(1-cyano-1-methylethyl)phenyl]ethyl}acetamide or a pharmaceutically acceptable salt thereof to a patient in need thereof.

One embodiment of the invention is a method of treating chronic tendinitis comprising administering an effective amount of the compound (S)(−)-N-{1-[4-(1-Cyano-1-methylethyl)phenyl]ethyl}-2-(6,7-difluoro-1H-benzimidazol-1-yl)acetamide or a pharmaceutically acceptable salt thereof to a patient in need thereof.

One embodiment of the invention is a method of treating chronic tendinitis comprising administering an effective amount of a compound of Formula I or a pharmaceutically acceptable salt thereof to a patient in need thereof.

One embodiment of the invention is a method of treating chronic tendinitis comprising administering an effective amount of the compound (S)(−)-2-(7-chloro-6-fluoro-1H-benzimidazol-1-yl)-N-{1-[4-(1-cyano-1-methylethyl)phenyl]ethyl}acetamide or a pharmaceutically acceptable salt thereof to a patient in need thereof.

One embodiment of the invention is a method of treating chronic tendinitis comprising administering an effective amount of the compound (S)(−)-N-{1-[4-(1-Cyano-1-methylethyl)phenyl]ethyl}-2-(6,7-difluoro-1H-benzimidazol-1-yl)acetamide or a pharmaceutically acceptable salt thereof to a patient in need thereof.

One embodiment of the invention is a method of treating pelvic pain comprising administering an effective amount of a compound of Formula I or a pharmaceutically acceptable salt thereof to a patient in need thereof.

One embodiment of the invention is a method of treating pelvic pain comprising administering an effective amount of the compound (S)(−)-2-(7-chloro-6-fluoro-1H-benzimidazol-1-yl)-N-{1-[4-(1-cyano-1-methylethyl)phenyl]ethyl}acetamide or a pharmaceutically acceptable salt thereof to a patient in need thereof.

One embodiment of the invention is a method of treating pelvic pain comprising administering an effective amount of the compound (S)(−)-N-{1-[4-(1-Cyano-1-methylethyl)phenyl]ethyl}-2-(6,7-difluoro-1H-benzimidazol-1-yl)acetamide or a pharmaceutically acceptable salt thereof to a patient in need thereof.

One embodiment of the invention is a method of treating peripheral neuropathy (primarily PHN) comprising administering an effective amount of a compound of Formula I or a pharmaceutically acceptable salt thereof to a patient in need thereof.

One embodiment of the invention is a method of treating peripheral neuropathy (primarily PHN) comprising administering an effective amount of the compound (S)(−)-2-(7-chloro-6-fluoro-1H-benzimidazol-1-yl)-N-{1-[4-(1-cyano-1-methylethyl)phenyl]ethyl}acetamide or a pharmaceutically acceptable salt thereof to a patient in need thereof.

One embodiment of the invention is a method of treating peripheral neuropathy (primarily PHN) comprising administering an effective amount of the compound (S)(−)-N-{1-[4-(1-Cyano-1-methylethyl)phenyl]ethyl}-2-(6,7-difluoro-1H-benzimidazol-1-yl)acetamide compound or a pharmaceutically acceptable salt thereof to a patient in need thereof.

One embodiment of the invention is a method of treating gastroesophageal reflux disease (GERD) comprising administering an effective amount of a compound of Formula I or a pharmaceutically acceptable salt thereof to a patient in need thereof.

One embodiment of the invention is a method of treating gastroesophageal reflux disease (GERD) comprising administering an effective amount of the compound (S)(−)-2-(7-chloro-6-fluoro-1H-benzimidazol-1-yl)-N-{1-[4-(1-cyano-1-methylethyl)phenyl]ethyl}acetamide or a pharmaceutically acceptable salt thereof to a patient in need thereof.

One embodiment of the invention is A method of treating gastroesophageal reflux disease (GERD) comprising administering an effective amount of the compound (S)(−)-N-{1-[4-(1-Cyano-1-methylethyl)phenyl]ethyl}-2-(6,7-difluoro-1H-benzimidazol-1-yl)acetamide or a pharmaceutically acceptable salt thereof to a patient in need thereof.

One embodiment of the invention is a method of treating Irritable Bowel Syndrome (IBS) comprising administering an effective amount of a compound of Formula I or a pharmaceutically acceptable salt thereof to a patient in need thereof.

One embodiment of the invention is a method of treating Irritable Bowel Syndrome (IBS) comprising administering an effective amount of the compound (S)(−)-2-(7-chloro-6-fluoro-1H-benzimidazol-1-yl)-N-{1-[4-(1-cyano-1-methylethyl)phenyl]ethyl}acetamide or a pharmaceutically acceptable salt thereof to a patient in need thereof.

One embodiment of the invention is a method of treating Irritable Bowel Syndrome (IBS) comprising administering an effective amount of the compound (S)(−)-N-{1-[4-(1-Cyano-1-methylethyl)phenyl]ethyl}-2-(6,7-difluoro-1H-benzimidazol-1-yl)acetamide or a pharmaceutically acceptable salt thereof to a patient in need thereof.

One embodiment of the invention is a method of treating overactive bladder comprising administering an effective amount of a compound of Formula I or a pharmaceutically acceptable salt thereof to a patient in need thereof.

One embodiment of the invention is a method of treating overactive bladder comprising administering an effective amount of the compound (S)(−)-2-(7-chloro-6-fluoro-1H-benzimidazol-1-yl)-N-{1-[4-(1-cyano-1-methylethyl)phenyl]ethyl}acetamide or a pharmaceutically acceptable salt thereof to a patient in need thereof.

One embodiment of the invention is a method of treating overactive bladder comprising administering an effective amount of the compound (S)(−)-N-{1-[4-(1-Cyano-1-methylethyl)phenyl]ethyl}-2-(6,7-difluoro-1H-benzimidazol-1-yl)acetamide or a pharmaceutically acceptable salt thereof to a patient in need thereof.

One embodiment of the invention is a pharmaceutical composition comprising a compound of Formula I or a pharmaceutically acceptable salt thereof and a pharmaceutically acceptable carrier.

One embodiment of the invention is a pharmaceutical composition comprising the compound (S)(−)-2-(7-chloro-6-fluoro-1H-benzimidazol-1-yl)-N-{1-[4-(1-cyano-1-methylethyl)phenyl]ethyl}acetamide and a pharmaceutically acceptable salt thereof and a pharmaceutically acceptable carrier.

One embodiment of the invention is a pharmaceutical composition comprising the compound (S)(−)-N-{1-[4-(1-Cyano-1-methylethyl)phenyl]ethyl}-2-(6,7-difluoro-1H-benzimidazol-1-yl)acetamide or a pharmaceutically acceptable salt thereof and a pharmaceutically acceptable carrier.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as form subcombinations thereof.

Some compounds of the invention have a chiral center. Such forms may be fractionated by chiral chromatography and the compounds fractionated that are dextrorotatory have greater antagonist activity than the levorotatory. While not wishing to be bound by any theory it is currently believed that the (+) isomers are the (R) enantiomers and the (−) isomers are the (S) enantiomers. Thus, while dextrorotatory, (D) or (+) or (R), and levorotatory, (L) or (−) or (S) compounds, are compounds of the invention, particular compounds of the invention are levorotatory, (S) or (−), compounds.

The sign of rotation claimed is observed for the sodium wavelength measured at 22° C. in a standard manner in solvents and concentrations where intermolecular associations are not suspected of occurring.

Recently the chiral (−)-2-[4-(1-aminoethyl)phenyl]-2-methyl-propanenitrile, obtained by fractionation of the corresponding racemic mixture, was confirmed to be of the (S) configuration. This (−) amine was also confirmed to be the chiral starting material leading to the (−) active final compounds claimed in the application. Since no inversion of the amine chiral stereo genic center was observed to occur under the coupling reaction it is reasoned that the configuration of the (−) active final compounds (obtained with this particular chiral amine) be of (S) configuration as well.

For chiral final (−) active compounds made using different but similar benzylic amines described above it is highly suspected that the chiral center be of the same (S) configuration however, there could be exceptions to this general claim.

Analyses were performed to verify the chiral structure of 2-[4-(1-aminoethyl)phenyl]-2-methyl-propanenitrile.
Results from vibrational circular dichroism (VCD) infrared analyses combined with molecular mechanics and density functional theory calculations of predicted VCD spectra were consistent with the proposed configurations.

Particular compounds described herein illustrate, but do not limit the invention, other compounds within the scope of the invention will be apparent to those of skill in the art upon contemplation of the processes, methods and compounds described herein.

The compounds provided herein are useful in the form as a free base, but may also be provided in the form of a pharmaceutically acceptable salt, and/or in the form of a pharmaceutically acceptable hydrate. For example a pharmaceutically acceptable salt of compounds of Formula I, include those derived from mineral acids such as for example: methane sulfonic acid, ethane sulfonic acid, hydrochloric acid, nitric acid, phosphoric acid, sulfuric acid, hydrobromic acid, hydroiodic acid, nitrous acid, and phosphorous acid. A pharmaceutically acceptable salt may also be developed with organic acids including aliphatic mono and dicarboxylates and aromatic acids.

Other a pharmaceutically acceptable salt of compounds of the present invention include for example sulfate, pyrosulfate, bisulfate, bisulfite, nitrate, and phosphate.

Compounds of Formula I can be made by processes known in the chemical arts for the production of structurally analogous compounds. Accordingly, the compounds of this invention may be prepared by employing procedures known in the literature starting from known compounds or readily prepared intermediates.

Provided herein are synthetic methods for the preparation of precursor compounds or use in practicing aspects of the present invention.

It will be appreciated by those skilled in the art that certain compounds of the present invention contain for example asymmetrically substituted carbon, and accordingly may exist in and be isolated in, optically-active and racemic forms. Some compounds may exhibit polymorphism, thus it is to be understood that the present invention encompasses racemic, optically active, polymorphic or stereoisomeric forms, or mixtures thereof, which forms possess properties useful in the treatment of the disorders set forth below. Preparation of optically active forms is well known in the art (for example by resolution of racemic forms by recrystallization techniques, synthesis from optically active starting materials, chiral synthesis, or by chromatographic separation using a chiral stationary phase.)

Compounds of Formula I are VR-1 antagonists. The compounds of Formula I, and their pharmaceutically acceptable salts, may also be used in a method for the treatment of pain, acute pain, chronic pain, nociceptive pain, acute nociceptive pain, chronic nociceptive pain, neuropathic pain, acute neuropathic pain, chronic neuropathic pain, inflammatory pain, acute inflammatory pain, chronic inflammatory pain. The treatment of such disorders comprises administering to a warm-blooded animal, preferably a mammal, more preferably a human, in need of such treatment, an effective amount of a compound of Formula I or a pharmaceutically acceptable salt of said compound.

Further provided is the use of a compound of Formula I in the treatment of osteoarthritis, chronic tendinitis, pelvic pain and peripheral neuropathy (primarily PHN), gastroesophageal reflux disease (GERD), irritable bowel syndrome (IBS), and overactive bladder.

Further provided is the use of a compound of Formula I in the preparation of a medicament for the treatment of a disorder such as pain in a warm-blooded animal, preferably a mammal, more preferably a human, suffering from such disorder.

The invention further provides a pharmaceutical composition suitable for the treatment of the above describe disorders comprising administering to a warm-blooded animal having such disorder an effective amount of a pharmaceutical composition of a compound of Formula I, or a pharmaceutically acceptable salt.

The invention also provides a pharmaceutical composition comprising a compound of Formula I, as defined herein, or a pharmaceutically acceptable salt, in combination with a pharmaceutically acceptable carrier.

At least one compound described herein demonstrates VR-1 antagonist activity in an assay described herein, of better than about 1 μM. Selected compounds of the present invention are found to be active antagonists with activity of less than about 100 nM.

The compounds described herein may be provided or delivered in a form suitable for oral use, for example in a tablet, lozenge, hard and soft capsule, aqueous solution, oily solution, emulsion, and suspension. The compounds may be also be provided for topical administration, for example, as a cream, ointment, gel, spray, or aqueous solutions, oily solutions, emulsions or suspensions. The compounds described herein may also be provided in a form suitable for nasal administration for example, as a nasal spray, nasal drops, or dry powder. The compositions may also be administered to the vagina or rectum in the form of a suppository. The compounds described herein may also be administered parentally, for example by intravenous, intravesicular, subcutaneous, or intramuscular injection or infusion. The compounds may be administered by insufflation (for example as a finely divided powder). The compounds may also be administered transdermally or sublingually.

The compounds of the invention may accordingly be obtained by conventional procedures using conventional pharmaceutical excipients, well known in the art. Thus, compositions intended for oral use may contain, for example, one or more coloring, sweetening, flavoring and/or preservative agents.

The amount of active ingredient that is combined with one or more excipients to produce a single dosage form will necessarily vary depending upon the host treated and the particular route of administration. The size of the dose for therapeutic or prophylactic purposes of a compound of the Formula I, will naturally vary according to the nature and severity of the conditions, the age and sex of the animal or patient and the route of administration, according to well known principles of medicine. Various assays and in vivo tests are known for determining the utility of the compounds in the disorders noted above and specifically as antagonists of VR-1 receptors.

A compound of Formula I or a pharmaceutically acceptable salt, solvate or in vivo hydrolysable ester thereof, or a pharmaceutical composition or formulation comprising a compound of Formula I is administered concurrently, simultaneously, sequentially or separately with another compound or compounds selected from the following:
(i) neuropathic pain therapies including for example gabapentin, lidoderm, pregablin and equivalents including but not limited to a pharmaceutically acceptable salt and pharmaceutically active isomer(s) and metabolite(s) thereof
(ii) nociceptive pain therapies including for example celecoxib, etoricoxib, lumiracoxib, rofecoxib, valdecoxib, diclofenac, loxoprofen, naproxen, paracetamol and equivalents including but not limited to a pharmaceutically acceptable salt and pharmaceutically active isomer(s) and metabolite(s) thereof.
(iii) urinary incontinence therapies including for example darifenacin, falvoxate, oxybutynin, propiverine, robalzotan, solifenacin, tispium, tolterodine and equivalents including but not limited to a pharmaceutically acceptable salt and pharmaceutically active isomer(s) and metabolite(s) thereof.

Such combination products employ the compounds of this invention within the dosage range described herein and the other pharmaceutically active agent within approved dosage ranges and/or the dosage described in the publication reference.

Methods of Preparation

Another aspect of the present invention provides processes for preparing compounds of Formula I or salts, solvates or solvated salts thereof.

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). References and descriptions of other suitable reactions are described in textbooks of organic chemistry, for example, "Advanced Organic Chemistry", March, $4^{th}$ ed. McGraw Hill (1992) or, "Organic Synthesis", Smith, McGraw Hill, (1994). For representative examples of heterocyclic chemistry see for example "Heterocyclic Chemistry", J. A. Joule, K. Mills, G. F. Smith, $3^{rd}$ ed. Chapman and Hall (1995), p. 189-224 and "Heterocyclic Chemistry", T. L. Gilchrist, $2^{nd}$ ed. Longman Scientific and Technical (1992), p. 248-282.

The term "room temperature" and "ambient temperature" shall mean, unless otherwise specified, a temperature between 16 and 25° C.

Abbreviations
DCE dichloroethane
DCM dichloromethane
DMAP N,N-dimethylaminopyridine
EDC 1-(3-dimethylaminopropyl)-3-ethylcarbodiimide hydrochloride
HATU O-(7-azabenzotriazol-1-yl)-N,N,N',N'-tetramethyluronium hexafluorophosphate
HPLC high performance liquid chromatography
KHMDS potassium hexamethyldisilazane
LC liquid chromatography
ret. time retention time
TFA trifluoroacetic acid
THF tetrahydrofuran
DMF dimethylformamide
TMEDA tetramethylethylenediamine
EtOAc ethyl acetate
DEA diethylamine
DMSO dimethyl sulfoxide
Min. minute
TEMPO 2,2,6,6-tetramethyl-1-piperidinyloxy
MPLC medium pressure liquid chromatography
MTBE methyl tbuyl ether
tlc thin layer chromatography
MeCN Acetonitrile
rbf round bottomed flask
MS low resolution mass spectroscopy
HRMS high resolution mass spectroscopy
[M+H] molecular ion+a proton
DIPEA disopropylethylamine
NMR nuclear magnetic resonance
Pd—C palladium on carbon
EtOH ethanol
MeOH methanol
t-BuOK potassium tertiarybutoxide
STP standard temperature pressure
CCD charge-coupled device

EXPERIMENTAL PROCEDURES

All starting materials are commercially available or described in the literature. The $^1$H NMR spectra are recorded on Variant at 400 MHz. The mass spectra are recorded on (LC-MS; LC:Agilent 1100, Waters ESI-MS, column Phenomenex Synergi Polar (4 u) 30×2 mm, flow rate; 1.75 ml/min, Mobile phase: A=water (0.05% TFA) B=MECN (0.05% TFA), Gradient: 5-95%, Gradient time: 2.25 min.). Final compounds are analyzed on LCMS Agilent 1100 (MS: Agilent APPI-MSD, Flow rate: 3.5 ml/min, Column: Zorbax SB (1.8 u) 4.6×30 mm, Column Temp: 70° C., Mobile phase: A=water (0.05% TFA) B=MECN (0.05% TFA), Gradient: 5-95%, Gradient time: 4.5 min.). The enantiomers of each product may be separated using Chiralcel OD or AD columns, from Chiral Technologies inc.

The final products are named by converting the racemic drawing of the molecule to the IUPAC name by using ACD lab software. Enantiomeric characterization in front of each name [(+), (−), (+,−), R, S] is added depending on what is known about the compound at the time.

Scheme 1: synthesis of (7-chloro-1H-benzimidazol-1-yl)acetic acid

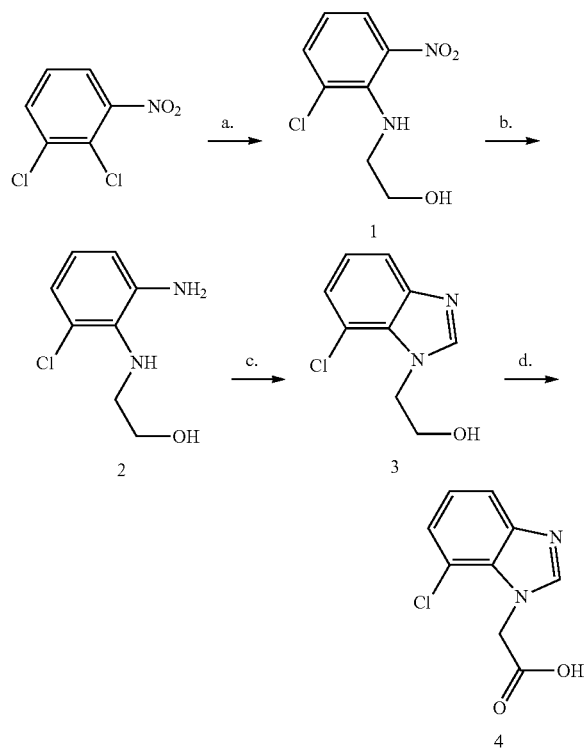

Step a) Intermediate 1

Synthesis of 2-[(2-chloro-6-nitrophenyl)amino]ethanol 2,3-dichloronitroaniline (300 g, 1.56 mol) is mixed with ethanol (600 ml) and ethanolamine (282 ml, 4.68 mol). The mixture is heated at reflux for 20 hrs then cooled and concentrated under vacuum. To eliminate the ethanolamine hydrochloride salt, the crude product is dissolved with 3.5 litres of AcOEt and 1 l of water. The aqueous phase is discarded and the organic phase is washed twice with 700 ml of water and with brine. After drying over anhydrous magnesium sulphate, the solution is filtered and evaporated under vacuum to give the desired product (336 g, 99%) as an orange oil.

Step b) Intermediate 2

Synthesis of 2-[(2-chloro-6-aminophenyl)amino]ethanol

To a solution of 2-[(2-chloro-6-nitrophenyl)amino]ethanol (120 g, 0.554 mol) in methanol (1.5 l) at 60° C. is added a solution of $Na_2S_2O_4$ (85%, 318 g, 1.55 mol) in water (1.12 l) over 20 min. The obtained suspension is stirred at 60° C. for additional 20 min. The decolourized mixture is allowed to cool and concentrated under vacuum. In an ice bath, 800 ml of 1.5 M NaOH solution is added and the mixture is extracted three times with 500 ml of AcOEt. The organic phase is washed with brine and dried over magnesium sulphate. The solvents are evaporated to give the desired product (72.4 g, 70%).

Step c) Intermediate 3

Synthesis of 2-(7-chloro-1H-benzimidazol-1-yl)ethanol

The 2-[(2-chloro-6-aminophenyl)amino]ethanol (72.4 g, 0.388 mol), is dissolved in formic acid (350 ml) and stirred under reflux for 1 hour. The reaction mixture is concentrated to dryness under reduced pressure to give a dark solid, then 500 ml of HCl 2N is added to the residue and the mixture is heated under reflux for 30 min. The solution is cooled on ice and 50% NaOH solution is added until alkaline and the obtained suspension is filtered under vacuum and the resulting solid dried to give the desired product (70.8 g 93%)

Step d) Intermediate 4

Synthesis of 2-(7-chloro-1H-benzimidazol-1-yl)acetic Acid 2-(7-chloro-1H-benzimidazol-1-yl)ethanol (50 g, 0.254 mol) is dissolved in 1 L of acetonitrile and sodium phosphate buffer (750 ml pH 6.7) and the mixture is heated to 40° C., TEMPO (2.9 g 18.5 mmol) is added followed by solid $NaClO_2$ (119 g, 85%, 1.06 mol) over 3 hours. The NaOCl solution (1.65 M, 40 ml) is simultaneously added until the reaction mixture turns dark brown. The mixture is left stirring for 16 hours at 45° C. The excess oxidizing agent is quenched (in a ice bath) with solid $Na_2SO_3$ (100 g) which is added until complete discolouration of the reaction mixture. At this stage a precipitate is formed. This solid, which contains 2-(7-chloro-1H-benzimidazol-1-yl)acetic acid and a mineral product, is filtered and dissolved in 500 ml of water. The resulting solution is then acidified to pH 2 with HCl 6N. The precipitate is filtered and wash with water to give 3.76 g of the desired product. The aqueous phase from the reaction mixture is acidified with HCl 6N to pH 2 and the solid that forms is filtered and washed with water to give 41.83 g of the desired product. The acetonitrile solution coming from the organic phase is concentrated to give a suspension of the crude product in water, which is purified by dissolving it with NaOH 50% solution. The aqueous solution is then washed with AcOEt and precipitated with HCl 6N to pH 6 to give 1.76 g of desired product for a total of 47.35 g (88%) of the desired product.

Scheme 2: synthesis of (6,7-difluoro-1H-benzimidazol-1-yl)acetic acid

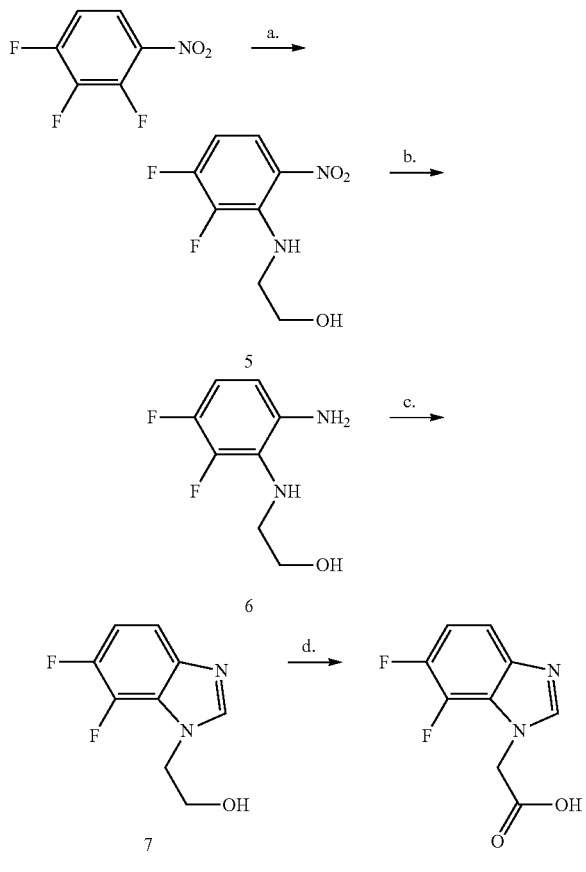

Scheme 2: synthesis of
(6,7-difluoro-1H-benzimidazol-1-yl)acetic Acid

Step a) Intermediate 5

Synthesis of
2-[(2,3-difluoro-6-nitrophenyl)amino]ethanol

A solution of 1,2,3-trifluoro-4-nitrobenzene (5.0 g, 28.2 mmol) and ethanolamine (1.72 g, 28.2 mmol) in 100 ml of ethanol is stirred over night at room temperature then at 70° C. for 5 hours. The reaction is concentrated to dryness and purified by silica gel flash chromatography using a gradient of 80/20 to 20/80 heptane/ethyl acetate providing an orange solid. Yield (3.8 g, 62%). $^1$H NMR (400 MHz, CDCl$_3$) δ ppm 1.67 (t, J=5.08 Hz, 1H) 3.77-3.83 (m, 2H) 3.88-3.94 (m, 2H) 6.51 (ddd, J=9.77, 8.59, 7.03 Hz, 1H) 8.02 (ddd, J=9.77, 5.66, 2.34 Hz, 1H) 8.21 (s, 1H)

Step b) Intermediate 6

Synthesis of
2-[(6-amino-2,3-difluorophenyl)amino]ethanol

To a solution of 2-[(2,3-difluoro-6-nitrophenyl)amino]ethanol (3.8 g, 17.4 mmol) in 70 ml of ethyl acetate and 30 ml of ethanol is added 10% Pd/C (380 mg). The reaction is shaken under 50 PSI of hydrogen for 3 hours. The pressure is periodically adjusted to 50 PSI. The reaction is filtered through celite, rinsed with ethanol and concentrated. The resulting material is used without further purification in the next step. $^1$H NMR (400 MHz, CDCl$_3$) δ ppm 3.17-3.27 (m, 2H) 3.68-3.78 (m, 2H) 6.38 (ddd, J=8.89, 4.69, 2.05 Hz, 1H) 6.61-6.70 (m, 1H)

Step c) Intermediate 7

Synthesis of
2-(6,7-difluoro-1H-benzimidazol-1-yl)ethanol

A solution of 2-[(6-amino-2,3-difluorophenyl)amino]ethanol in 100 ml of formic acid is heated at 100° C. for 2 hours. The reaction is concentrated to dryness, taken into 100 ml of 2 N NH$_3$ in ethanol and stirred for 2.5 hrs. The reaction is concentrated and taken into ethyl acetate. The resulting precipitate is collected by filtration and rinsed with cold ethyl acetate. The mother liquor is concentrated and purified by silica gel flash chromatography using ethyl acetate/heptane. The combined yield is 3.2 g or 93% for two steps based on 3.8 g of 2-[(2,3-difluoro-6-nitrophenyl)amino]ethanol.

Step c) Intermediate 8

Synthesis of
(6,7-difluoro-1H-benzimidazol-1-yl)acetic acid 2-(6,7-difluoro-1H-benzimidazol-1-yl)ethanol (2.96 g, 15 mmol) is taken into 75 ml of MeCN and sodium phosphate buffer (56 ml, 0.67 M, pH 6.8) and the mixture is heated to 42° C. TEMPO (165 mg, 1.05 mol) is added followed by the simultaneous dropwise addition of a solution of NaClO$_2$ (3.38 g, 80% pure, 30 mmol in 15 ml water) and a solution of bleach (350 µL of 6% NaOCl in 7.5 mL water) over 1.5 hours. After 48 hrs, the same quantities of NaClO$_2$ and bleach are added. After a further 24 hours, TEMPO (165 mg, 1.05 mol) is added and the reaction is stirred for 72 hrs. The darkened reaction is allowed to cool to room temperature followed by the dropwise addition of 30 ml of a saturated solution of Na$_2$SO$_3$ (exothermic). The reaction becomes almost colourless. Using 2 N NaOH, the pH is raised to 9.2 and the reaction is extracted 4 times with ethyl acetate. The pH is then lowered to 3.8 with 2 N HCl and the solution allowed to stand for 48 hours. 1.98 grams of white crystalline material is recovered. The mother liquor is reduced to half the volume and allowed to stand. A further 260 mg is collected. (Combined yield 2.23 g, 70%)

$^1$H NMR (400 MHz, DMSO-D6) δ ppm 5.19 (s, 2H) 7.25 (ddd, J=11.62, 8.89, 7.62 Hz, 1H) 7.49 (ddd, J=8.94, 3.86, 1.07 Hz, 1H) 8.13-8.28 (m, 1H) 13.38 (s, 1H)

Scheme 3: synthesis of (7-cyano-1H-benzimidazol-1-yl)acetic acid

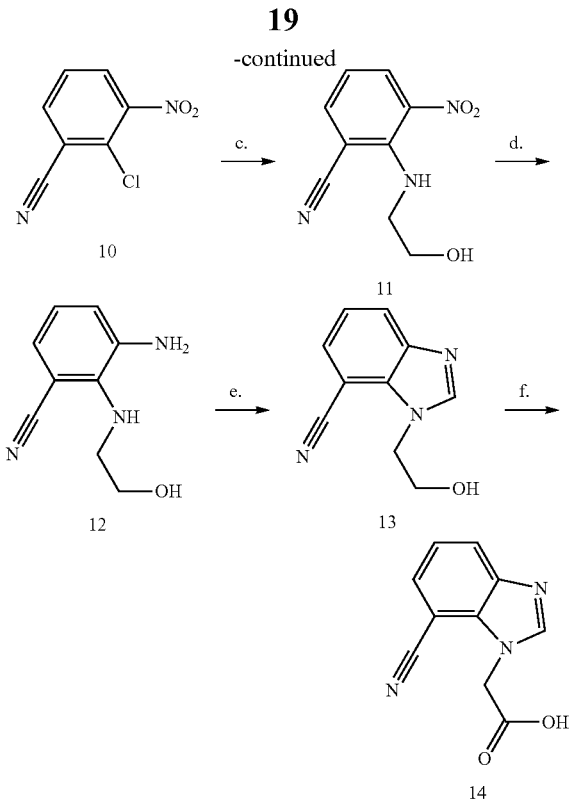

Step a) Intermediate 9

Synthesis of 2-chloro-3-nitrobenzamide

2-Chloro-3-nitrobenzoic acid (100 g, 0.496 g) is heated to reflux in neat thionyl chloride for 2.5 hours with stirring (a gas evolves). After cooling the thionyl chloride is evaporated to dryness. The resulting solid is dissolved in 150 ml of dichloromethane, cooled in an ice bath and 400 ml of 28% ammonium hydroxide is added over 1 hour (the reaction is exothermic). Then 100 ml of water is then added to facilitate the precipitation. The precipitate formed is filtered, washed with water and dried for 16 hours over $P_2O_5$ under vacuum to give the desired product (83.2 g, 83%) as a pale yellow fluffy solid.

1H NMR (300 MHz, DMSO-d6) δ ppm 7.61 (t, J=7.93 Hz, 1H) 7.72 (dd, J=7.63, 1.47 Hz, 1H) 8.04 (dd, J=7.94, 1.47 Hz, 1H)

Step b) Intermediate 10

Synthesis of 2-chloro-3-nitrobenzonitrile 2-chloro-3-nitrobenzamide (83 g, 0.413 mol, well dried) is added to the refluxing solution of dehydrating agent* and this mixture is then left at this temperature for 4 hours and at room temperature for 16 hours. The mixture is quenched with ice, 400 ml of water is added to facilitate the phase separation and the aqueous phase is discarded. The organic phase is washed with water and brine and then dried over anhydrous $Na_2SO_4$. The solution is filtered and concentrated to give the desired product (74.4 g, 99%).

1H NMR (300 MHz, DMSO-d6) δ ppm 7.76 (t, J=7.93 Hz, 1H) 8.27 (dd, J=7.93 1.47 Hz, 1H) 8.36 (dd, J=8.22 1.47 Hz, 1H)

*Preparation of Trimethylsilyl Polyphosphate (Dehydrating Agent):

$P_2O_5$ (254 g; 1.79 mol) in 1 litre of anhydrous dichloromethane is stirring under reflux and 330 ml of hexamethyldisiloxane (1.54 mol) is added over 1 hour by a dropping funnel (the reaction is exothermic). The reaction mixture is then left stirring at this temperature for 1 hour.

Step c) Intermediate 11

Synthesis of 2-[(2-hydroxyethyl)amino]-3-nitrobenzonitrile 2-chloro-3-nitrobenzonitrile (74 g, 0.408 mol) is mixed with ethanol (370 ml) and ethanolamine (57 ml). The mixture is stirred for 16 hrs at room temperature. To complete the reaction, the mixture is refluxed for 2 hours. After cooling, the mixture is concentrated under vacuum; the product precipitates as a red solid. To eliminate the ethanolamine hydrochloride salt, the suspension is triturated with 500 ml of water and filtrated under vacuum. The solid is washed with ethanol and ether then dried to give the desired product (75 g, 89%).

1H NMR (300 MHz, DMSO-d6) δ ppm 3.55-3.60 (m, 2H) 3.69-3.74 (m, 2H) 6.75 (dd, J=7.63, 8.52 Hz, 2H) 7.90 (dd, J=7.63, 1.76 Hz, 2H) 8.27 (dd, J=8.52, 1.76 Hz, 1H) 3.35 m, 1H)

Step d) Intermediate 12

Synthesis of 3-amino-2-[(2-hydroxyethyl)amino]benzonitrile

Methanol (500 ml) and Pd/activated charcoal 5% (wet, 3.45 g) are added to 2-[(2-hydroxyethyl)amino]-3-nitrobenzonitrile (69 g, 0.333 mol). The suspension is shaken in a Parr apparatus under 20 psi pressure of hydrogen for 1 hour. The mixture is then filtered on Celite and evaporated to dryness to give the desired material (62.7 g). This product is used in the next step without further purification.

1H NMR (300 MHz, MeOD) δ ppm 3.41 (t, J=5.43 Hz, 2H) 3.70 (t, J=5.43 Hz, 2H) 6.75 (t, J=7.71 Hz, 1H) 6.87 (dd, J=7.71, 1.61 Hz, 1H) 6.92 (dd, J=7.71, 1.61 Hz, 1H)

Step e) Intermediate 13

Synthesis of 1-(2-hydroxyethyl)-1H-benzimidazole-7-carbonitrile 3-amino-2-[(2-hydroxyethyl)amino]benzonitrile (38 g, crude), is dissolved in formic acid (150 ml) and stirred under reflux for 1 hour. The reaction mixture is concentrated to dryness under reduced pressure to give a dark solid. This solid is dissolved in 200 ml of methanol with heating and while still hot, 60 ml of triethylamine is added and reflux for 1 hour. The mixture is concentrated under vacuum and the precipitate is filtered and washed with water then dried to give the desired compound (27 g, 70% from intermediate 11).

1H NMR (300 MHz, DMSO-d6) δ ppm 3.79 (dt, J=5.14 Hz, 2H) 4.51 (t, J=5.14 Hz, 2H) 5.04 (t, J=5.14 Hz, 1H) 7.34 (dd, J=7.63, 0.77 Hz, 1H) 7.74 (dd, J=7.63, 0.77 Hz) 8.02 (dd, J=7.73, 0.77 Hz) 8.36 (s, 1H)

Step f) Intermediate 14

Synthesis of (7-cyano-1H-benzimidazol-1-yl)acetic Acid 1-(2-hydroxyethyl)-1H-benzimidazole-7-carbonitrile (61.4 g, 0.328 mol) is dissolved in acetonitrile (1.2 L) and sodium phosphate buffer (930 ml, pH 6.8) and the mixture is heated at 40° C. TEMPO (3.6 g 22.7 mol) is added followed by solid NaClO$_2$ (148.3 g 85%, 1.31 mol) over 3 hours. The NaOCl solution (1.65 M, 50 ml) is simultaneously added until the reaction mixture turns dark brown. The mixture is left stirring for 16 hours at 45° C. The excess oxidant is quenched (in a ice bath) with solid Na$_2$SO$_3$ which is added until complete discoloration of the reaction mixture.

At this stage a precipitate forms. This solid contains the desired products and mineral salt products, it is filtered and dissolved in 500 ml of water. The resulting solution is then acidified to pH 2 with HCl 6N. The precipitate is filtered and wash with water to give the desired product (12.7 g, 19%). The aqueous phase coming from the reaction mixture, is acidified with HCl 6N to pH 2 and the solid that forms is filtered and washed with water and dried to give the desired product (43.0 g, 65%) of the final product. The acetonitrile coming from the organic phase is evaporated to give a suspension of the crude product in water which is purified by dissolving it with NaOH 50% solution, washing with AcOEt and precipitating with HCl 6N to pH 6 to give the desired product (4.2 g, 6%), (59.9 g, 90% combined yields).

1H NMR (300 MHz, DMSO-d6) δ ppm 5.31 (s, 2H) 7.36 (t, J=7.78 Hz, 1H) 7.74 (dd, J=1.03, 7.78 Hz, 1H) 8.03 (dd, J=1.03, 7.78 Hz, 1H) 8.37 (s, 1H)

Scheme 4: Synthesis of 7-Acetyl-1H-benzimidazole-1-yl)acetic acid

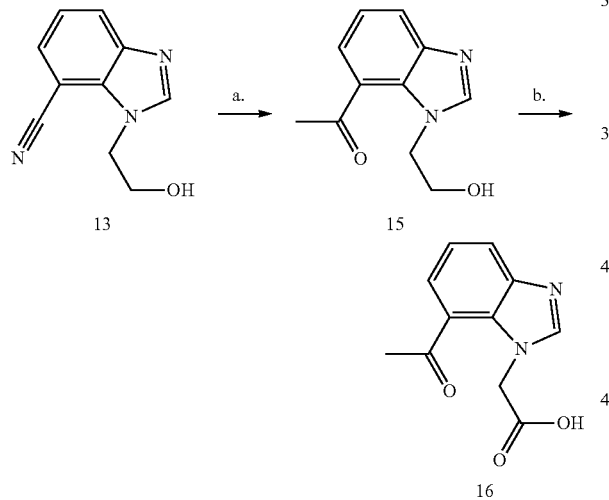

Step a) Intermediate 15

Synthesis of 1-[1-(2-Hydroxyethyl)-1H-benzimidazol-7-yl]ethanone

A solution of 1-(2-hydroxyethyl)-1H-benzimidazole-7-carbonitrile (0.29 g, 1.5 mmol) in dry THF (6.2 ml) is cooled to −78° C. and MeLi (5.8 mL, 9.3 mmol) is added slowly. After the addition the reaction mixture is allowed to warm up to ambient temperature and kept such for 30 min. The temperature is brought down to −78° C. again and water (4 ml) was added slowly. After warming up the reaction mixture is acidified at pH 4 and heated at 50° C. for 30 min. Solvents are removed under reduced pressure and the residue is partitioned between ethyl acetate and aq. NaHCO$_3$. The organic extract is further washed with water and brine, dried over Na$_2$SO$_4$ and concentrated. Purification is performed on flash silica column using ethyl acetate-methanol as the eluent to give the desired product (0.25 g, 80%).

$^1$H NMR (400 MHz, DMSO-D6) δ ppm 2.67 (s, 3H) 3.51 (q, J=5.1 Hz, 2H) 4.41 (t, J=5.3 Hz, 2H) 4.77 (t, J=5.1 Hz, 1H) 7.29 (t, J=7.8 Hz, 1H) 7.78 (dd, J=7.6, 1.0 Hz, 1H) 7.88 (dd, J=8.1, 1.0 Hz, 1H) 8.20 (s, 1H)

Step b) Intermediate 16

Synthesis of (7-acetyl-1H-benzimidazol-1-yl)acetic Acid

1-[1-(2-Hydroxyethyl)-1H-benzimidazol-7-yl]ethanone (0.30 g, 1.47 mmol) is oxidized to the desired acid according to the procedure described for the synthesis of (7-Cyano-1H-benzimidazol-1-yl)acetic acid (step f, intermediate 14) to give the desired product (0.24 g, 75%).

1H NMR (400 MHz, METHANOL-D4) δ ppm 2.64 (s, 3H) 5.34 (s, 2H) 7.46 (t, J=7.81 Hz, 1 H) 7.90-7.99 (m, J=6.84, 6.84 Hz, 2H) 8.56 (s, 1H)

Scheme 5: Synthesis of 7-Fluoro-1H-benzimidazole-1-yl)acetic acid

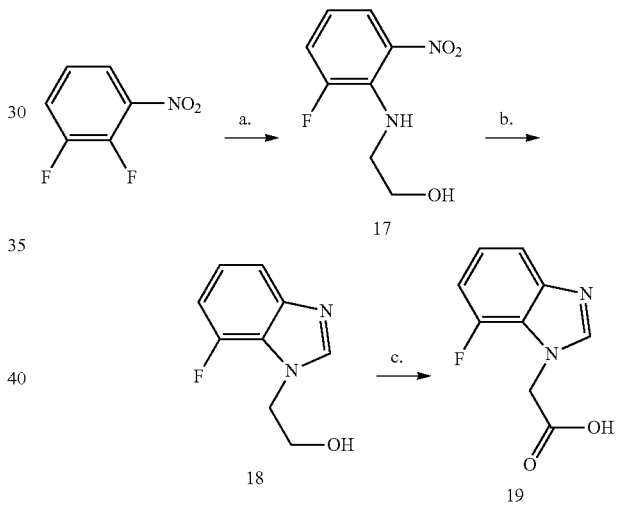

Step a) Intermediate 17

Synthesis of 2-[(2-fluoro-6-nitrophenyl)amino]ethanol 2,3-Difluoronitrobenzene (15 g, 94.3 mmol) is dissolved in 200 mL of ethanol. Ethanolamine (11.4 ml, 188.7 mmol, 2 equiv) is added and the mixture stirred at room temperature overnight (reaction complete by TLC). Ethanol is evaporated and the resulting residue is dissolved in ethyl acetate, washed with water (to eliminate excess ethanolamine), dried over magnesium sulphate, filtered and evaporated to dryness, giving the desired product as a deep orange oil (18.3 g, 97%). This crude material was used for the next step without further purification.

$^1$H-NMR (400 MHz, CD$_3$OD) δ 3.61-3.68 (m, 2H) 3.69-3.76 (m, 2H) 4.88 (s, 2H) 6.61-6.67 (m, 1H) 7.27 (ddd, J=14.16, 7.91, 1.56 Hz, 1H) 7.91 (dt, J=8.69, 1.51 Hz, 1H). MS [M+H], calcd: 201. found: 201.

Step b) Intermediate 18

Synthesis of 2-(7-fluoro-1H-benzimidazol-1-yl)ethanol

2-[(2-fluoro-6-nitrophenyl)amino]ethanol (18.3 g, 91.5 mmol) dissolved in 90 mL of formic acid is added to a suspension of Pd—C 10% (300 mg) in 10 ml of formic acid. The mixture is shaken in a Parr apparatus under atmospheric pressure of $H_2$ overnight. The reaction mixture is filtered over Celite, the solvent is evaporated under vacuum and the resulting residue dissolved in $NH_3$ 2M in ethanol. This solution is stirred at room temperature for 1 h (to cleave the formic acid adduct). A precipitate forms. This mixture is evaporated to dryness and purified by column chromatography ($SiO_2$, DCM/MeOH 10:1 to 5:1), giving the desired product as a white solid (10.5 g, 64%) TLC: DCM/MeOH 5:1, $R_f$=0.23.

$^1$H-NMR (400 MHz, $CD_3OD$) δ 3.86-3.95 (m, 2H) 4.46 (t, J=5.27 Hz, 2H) 7.03 (dd, J=11.72, 8.01 Hz, 1H) 7.21 (td, J=8.11, 4.88 Hz, 1H) 7.47 (d, J=7.81 Hz, 1H) 8.13 (s, 1H). MS [M+H], calcd: 181. found: 181.

Step c) Intermediate 19

Synthesis of (7-fluoro-1H-benzimidazol-1-yl)acetic acid 2-(7-fluoro-1H-benzimidazol-1-yl)ethanol (706 mg, 3.92 mmol) is suspended in 20 mL of acetonitrile and 15 mL of sodium phosphate buffer 1M (pH 6.5). The mixture is heated to 35° C. TEMPO (43 mg, 0.27 mmol) is added, followed by $NaClO_2$ (80%, 887 mg, 7.84 mmol) dissolved in 4 mL of water and diluted bleach (2 ml of a 0.4% aqueous solution). The reaction mixture turns red-brown after the bleach addition. To drive the reaction to completion, if needed, more TEMPO (22 mg), $NaClO_2$ (440 mg in 2 mL of water) and diluted bleach (1 mL) are added and the mixture stirred 6 hours at 35° C. After cooling at room temperature, the reaction is quenched by addition of saturated aqueous $Na_2SO_3$ (5 mL). The brown-red color disappears. The pH is adjusted to 8-9 by addition of NaOH 2M and the mixture is washed with ethyl acetate (2×). The organic layer is discarded and the aqueous phase is acidified with HCl 1M (up to pH 3). The desired product is crystallized in the aqueous phase as a white solid (537 mg, 70%). TLC: dichloromethane/methanol 10:1+5% triethylamine, $R_f$=0.33 (s.m.: Rf=0.56)

$^1$H-NMR (400 MHz, $CD_3OD$) δ 5.19 (s, 2H); 7.05 (dd, J=11.52, 8.20 Hz, 1H); 7.24 (td, J=8.15, 4.98 Hz, 1H); 7.49 (d, J=8.20 Hz, 1H); 8.19 (s, 1H). MS [M+H], calcd: 196. found: 195.

Scheme 6 Synthesis of 2-[4-(1-aminoethyl)phenyl]-2-methylpropanenitrile

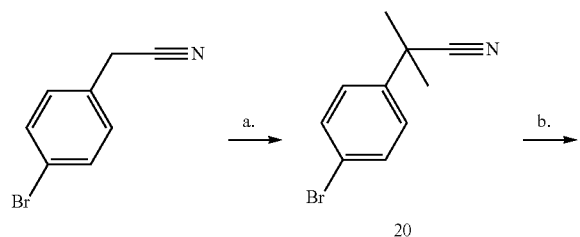

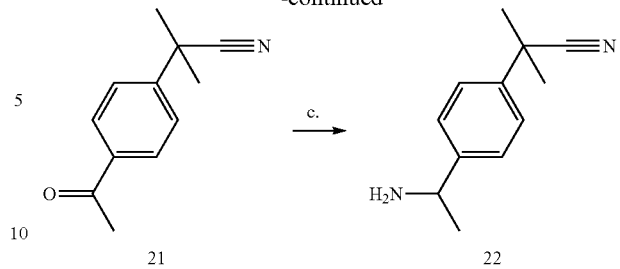

Step a) Intermediate 20

Synthesis of 2-(4-bromophenyl)-2-methylpropanenitrile

The preparation of 2-(4-bromophenyl)-2-methylpropanenitrile is carried out as described in J. Med. Chem. (1995), no 38, page 1608-1628. Sodium Hydride (60% susp. in oil, 6.66 g, 166.3 mmol) is added in many portions over 1 hour to 2-(4-bromophenyl)-acetonitrile (10 g, 51.0 mmol), dissolved in anhydrous DMF and methyl iodide (14.838 g, 102.0 mmol) at 0° C. This solution turns to a thick and brown orange paste. It is left stirring to slowly warm up to room temperature (18 h). The organic solution is partitioned between water and ethyl acetate, separated, dried over anhydrous sodium sulfate and filtered. The solution is concentrated under reduced pressure and the resulting crude is purified on silicagel using a 0 to 20% ethyl acetate in hexane gradient to yield the desired compound (4.9 g, 42%) as a clear oil.

1H NMR (400 MHz, CHLOROFORM-D) δ ppm 1.71 (s, 6H) 7.35 (d, J=8.79 Hz, 2H) 7.52 (d, J=8.79 Hz, 2H)

Step b) Intermediate 21

Synthesis of 2-(4-acetylphenyl)-2-methylpropanenitrile 2-(4-bromophenyl)-2-methylpropanenitrile (1 g, 4.46 mmol) is dissolved in anhydrous THF (75 ml) the solution is cooled down to −100° C. with a diethyl ether-liquid nitrogen bath, n-butyl lithium 2M in c-hexane (4.0 ml, 8.0 mmol) is added and this reaction mixture stirred for 10 min., then N-methoxy-N-methyl acetamide (1.6 g, 15.6 mmol) is added and the reaction is then left to slowly warm-up to room temperature. After work-up (washing with acidic brine) and concentration the crude mixture is purified on silica gel using a 0 to 50% ethyl acetate in hexane gradient, to give the desired compound (660 mg, 78%) as a clear oil.

1H NMR (400 MHz, CHLOROFORM-D) δ ppm 1.76 (s, 6H) 2.62 (s, 3H) 7.59 (d, J=8.79 Hz, 2H) 7.99 (d, J=8.79 Hz, 2H)

Step c) Intermediate 22

Synthesis of 2-[4-(1-aminoethyl)phenyl]-2-methylpropanenitrile

The preparation of 2-[4-(1-aminoethyl)phenyl]-2-methylpropanenitrile is carried out according to a general procedure described in Tetrahedron (2004), no 60, page 1463-1471. The acetophenone, 2-(4-acetylphenyl)-2-methylpropanenitrile (600 mg, 3.21 mmol) is dissolved in a 28% ammonia in ethanol solution (20.0 ml). Titanium isopropoxide (1.82 g, 6.42 mmol) is added and this reaction mixture which is then left stirring 18 h at room temperature. Sodium borohydride is added in two portions then left stirring 3 h. The clear solution slowly turns to grey then white, water is added and the titanium oxide removed by filtration. The organic solution is partitioned between water and ethyl acetate, separated, dried over anhydrous sodium sulfate and filtered. The solution is concentrated under reduced pressure. The resulting residue is dissolved in diethyl ether, filtered, and HCl in ether added, the resulting precipitate is filtered then dried to give the desired product as the HCl salt (500 mg, 69%) as a yellow solid.

1H NMR (400 MHz, METHANOL-D4) δ ppm 1.61 (d, J=6.90 Hz, 3H) 1.70 (s, 6H) 4.46 (q, J=6.90 Hz, 1H) 7.49 (dt, J=8.64, 2.34, 2.10 Hz, 2H) 7.60 (dt, J=8.64, 2.10 Hz, 2H), MS [M+H] calcd.: 189.1. found: 189.3.

Scheme 7
Synthesis of 2-(4-(1-aminoethyl)-2-fluorophenyl)-2-methylpropanenitrile

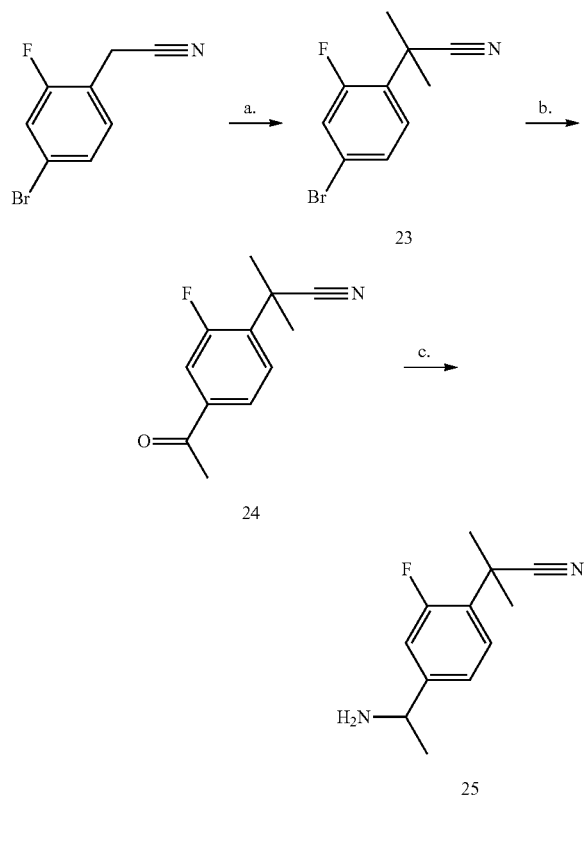

Step a Intermediate 23

Synthesis of
2-(4-bromo-2-fluorophenyl)-2-methylpropanenitrile 2-(4-bromo-2-fluorophenyl)-2-methylpropanenitrile is prepared from (4-bromo-2-fluorophenyl)acetonitrile (10 g, 51.0 mmol) using the procedure as described for intermediate 20 above to yield the desired product (11 g, 89%) as a crude pale yellow oil which does not require further purification.

1H NMR (400 MHz, CHLOROFORM-D) δ ppm 1.77 (d, J=0.78 Hz, 6H) 7.24-7.40 (m, 3H)

Step b Intermediate 24

Synthesis of
2-(4-acetyl-2-fluorophenyl)-2-methylpropanenitrile 2-(4-acetyl-2-fluorophenyl)-2-methylpropanenitrile is prepared from (4-bromo-2-fluorophenyl)acetonitrile (5.0 g, 21.0 mmol) using the procedure as described for intermediate 21 to yield the desired product (4.15 g, 99%) as a crude yellow oil which is not purified further after work-up.

1H NMR (400 MHz, CHLOROFORM-D) δ ppm 1.79-1.81 (m, 6H) 2.58 (s, 3H) 7.60 (t, J=7.91 Hz, 1H) 7.65 (dd, J=12.40, 1.46 Hz, 1H) 7.72 (dd, J=8.11, 1.86 Hz, 1H)

Step c Intermediate 25

Synthesis of 2-(4-(1-aminoethyl)-2-fluorophenyl)-2-methylpropanenitrile 2-(4-(1-aminoethyl)-2-fluorophenyl)-2-methylpropanenitrile is prepared from the crude (4-acetyl-2-fluorophenyl)acetonitrile (2.4 g, 11.7 mmol) using the procedure as described for intermediate 22 to yield the desired product as the HCl salt (2.1 g, 67%) as a crude pale yellow oil which does not require further purification after work-up.

1H NMR (400 MHz, DMSO-D6) δ ppm 1.19 (d, J=6.44 Hz, 3H) 1.67 (s, 6H) 1.95 (s, 3H) 3.95 (q, J=6.44 Hz, 1H) 7.19 (dd, J=8.11, 1.66 Hz, 1H) 7.26 (dd, J=13.48, 1.56 Hz, 1H) 7.34 (t, J=8.30 Hz, 1H), MS [M+H] calcd.: 207.13. found: 207.15.

Scheme 8 Synthesis of
2-(4-(aminomethyl)-2-fluorophenyl-2-methylpropanenitrile

Step a Intermediate 26

Synthesis of
2-(4-formyl-2-fluorophenyl)-2-methylpropanenitrile 2-(4-formyl-2-fluorophenyl)-2-methylpropanenitrile is prepared from (4-bromo-2-fluorophenyl)acetonitrile (5.2, 21.5 mmol) and N-methoxy-N-methyl formamide (3.8 g, 43.0) mmol using a similar procedure as described for intermediate 21 to yield the desired product which is used directly in the next step.

1H NMR (400 MHz, CHLOROFORM-D) δ ppm 1.82 (s, 3H), 1.81 (s, 3H) 7.59 (dd, J=11.62, 1.07 Hz, 1H) 7.65-7.74 (m, 2H) 9.97 (d, J=1.95 Hz, 1H)

Step b Intermediate 27

Synthesis of 2-(4-(aminomethyl)-2-fluorophenyl)-2-methylpropanenitrile 2-(4-(1-aminoethyl)-2-fluorophenyl)-2-methylpropanenitrile is prepared from the crude (4-acetyl-2-fluorophenyl)acetonitrile (crude 26) using the general procedure as described for intermediate 22 to give the desired product as the HCl salt (1.2 g, 16% for steps a and b) as a crude pale yellow oil which does not require further purification after work-up.

1H NMR (400 MHz, CHLOROFORM-D) δ 1.77 (s, 6H) 4.13 (s, 2H) 7.31 (d, J=10.55 Hz, 2H) 7.58 (t, J=8.11 Hz, 1H) MS [M+H] calcd.: 193.1. found: 193.3.

Scheme 9
Synthesis of 1-[4-(1-aminoethyl)phenyl]cyclobutanecarbonitrile

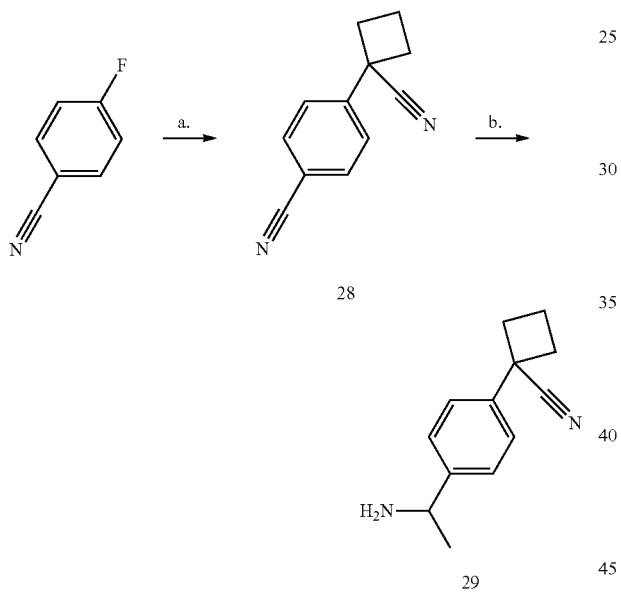

Step a Intermediate 28

Synthesis of 4-(1-cyanocyclobutyl)benzonitrile

Solid KHMDS (3.48 g, 17.5 mmol) is dissolved in THF (20.0 mL) and cooled to 0° C. Cyclobutanecarbonitrile (1.42 g, 17.5 mmol) is added, and the resulting solution stirred for 40 minutes. A solution of 4-fluorobenzonitrile (2.12 g, 17.5 mmol) in THF (10.0 mL) is added, and the mixture stirred for 2 hours at 0° C. 1N HCl (50.0 mL) is added to the reaction mixture and the aqueous phase extracted with EtOAc (4×40.0 mL). The combined organic phases are dried over MgSO₄, filtered and concentrated on the rotovaporator. The product is purified by flash chromatography (CombiFlash), eluting with mixtures of heptanes and EtOAc (0% EtOAc to 40% EtOAc) to yield the desired product (1.76 g, 9.67 mmol, 55%). ¹H NMR (400 MHz, DMSO-D6) δ ppm 1.92-2.12 (m, 1H) 2.19-2.37 (m, 1H) 2.57-2.69 (m, 2H) 2.71-2.82 (m, 2H) 7.67 (d, J=8.59 Hz, 2H) 7.91 (d, J=8.79 Hz, 2H).

Step b Intermediate 29

Synthesis of 1-[4-(1-aminoethyl)phenyl]cyclobutanecarbonitrile 4-(Cyanocyclobutyl)benzonitrile (335 mg, 1.84 mmol) is mixed with THF (10.0 mL) and cooled to −78° C. under N₂ gas. MeLi (1.15 mL, 1.84 mmol, 1.60M in Et₂O) is added, and the mixture is stirred at −78° C. for 15 minutes. A mixture of NaBH₄ (70.0 mg, 1.84 mmol) in MeOH (10.0 mL) is added, and the solution is warmed to 0° C. for 1 hour. 1N HCl (40.0 mL) is added, and the solution is concentrated to dryness on the rotovaporator. The product is purified by HPLC: Gilson prep pumps, flow rate: 30 ml/min, column: Synergi Gemini (5u) 21.2×50 mm (high pH), mobile phase: A=water (10 mM NH₄CO₃) B=MECN, (95.0 mg, 0.475 mmol, 26%). ¹H NMR (400 MHz, DMSO-D6) δ ppm 1.23 (d, J=6.64 Hz, 3H) 1.90-2.06 (m, 1H) 2.16-2.35 (m, 1H) 2.52-2.64 (m, 2H) 2.64-2.78 (m, 2H) 4.00 (q, J=6.64 Hz, 1H) 7.36 (d, J=8.59 Hz, 2H) 7.42 (d, J=8.20 Hz, 2H).

Scheme 10: Synthesis of 1-[4-(1-aminoethyl)phenyl]cyclopropylcarbonitrile

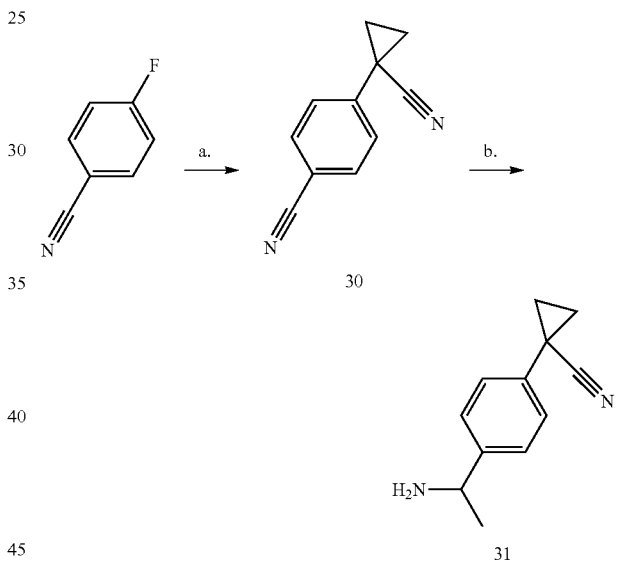

Step a Intermediate 30

Synthesis of 4-(1-cyanocyclopropyl)benzonitrile

Solid KHMDS (6.82 g, 34.3 mmol) is dissolved in THF (60.0 mL) and cooled to −40° C. Cyclopropanecarbonitrile (2.30 g, 34.3 mmol) is added, and the resulting solution is stirred for 30 minutes. A solution of 4-fluorobenzonitrile (4.15 g, 34.3 mmol) in THF (20.0 mL) is added, and the mixture is stirred for 20 minutes at −40° C. followed by 2 hours at room temperature. A saturated solution of NaHCO₃ (50.0 mL) is added, and the aqueous phase is extracted with EtOAc (4×40.0 mL). The combined organic phases are dried over MgSO₄, filtered and concentrated on the rotovaporator. The product is purified by flash chromatography (Combi-Flash), eluting with mixtures of heptanes and EtOAc (0% EtOAc to 70% EtOAc) (743 mg, 4.42 mmol, 13%). ¹H NMR (400 MHz, DMSO-D6) δ ppm 1.60-1.67 (m, 2H) 1.84-1.90 (m, 2H) 7.49 (d, J=8.59 Hz, 2H) 7.85 (d, J=8.79 Hz, 2H).

Step b Intermediate 31

Synthesis of 1-[4-(1-aminoethyl)phenyl]cyclopropylcarbonitrile 4-(Cyanocyclopropyl)benzonitrile (132 mg, 0.786 mmol) is mixed with THF (10.0 mL) and cooled to −78° C. under $N_2$ gas. MeLi (0.639 mL, 1.02 mmol, 1.60M in $Et_2O$) is added, and the mixture is stirred at −78° C. for 60 minutes. A mixture of $NaBH_4$ (39.0 mg, 1.02 mmol) in MeOH (10.0 mL) is added, and the solution is warmed to 0° C. for 1 hour. 1N HCl (40.0 mL) is added, and the solution is concentrated to dryness on the rotovaporator. The product is purified by HPLC: Gilson prep pumps, flow rate: 30 ml/min, column: Synergi Gemini (5u) 21.2×50 mm (high pH), mobile phase: A=water (10 mM $NH_4CO_3$) B=MECN, (23.0 mg, 0.0623 mmol, 14%). $^1$H NMR (400 MHz, DMSO-D6) δ ppm 1.32 (d, J=6.64 Hz, 3H) 1.42-1.51 (m, 2H) 1.66-1.77 (m, 2H) 4.09-4.20 (m, J=6.84 Hz, 1H45 7.30 (d, J=8.59 Hz, 2H) 7.42 (d, J=8.20 Hz, 1H).

Scheme 11: Synthesis of 1-[4-(1-aminoethyl)phenyl]cyclohexylcarbonitrile

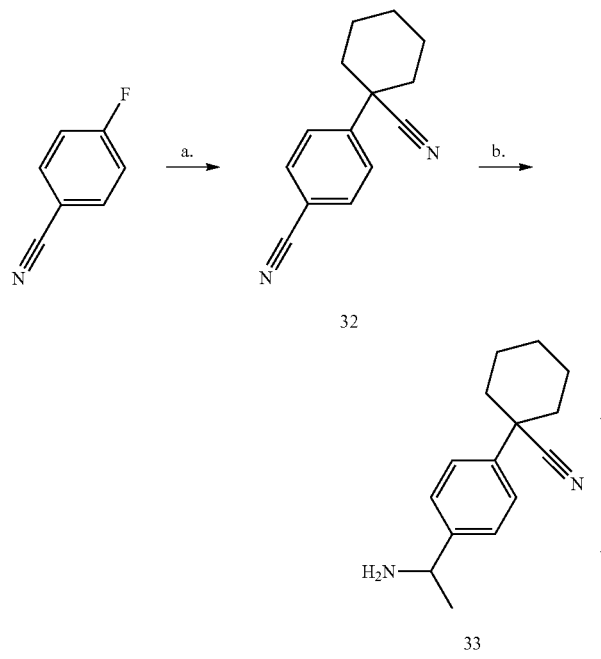

Step a Intermediate 32

Synthesis 4-(1-cyanocyclohexyl)benzonitrile

Solid KHMDS (4.36 g, 22.0 mmol) is dissolved in THF (80.0 mL) and cooled to 0° C. Cyclohexanecarbonitrile (2.38 g, 22.0 mmol) is added, and the resulting solution is stirred for 40 minutes. A solution of 4-fluorobenzonitrile (1.33 g, 10.95 mmol) in THF (10.0 mL) is added, and the mixture is stirred for 2 hours at 0° C. and 10 hours at room temperature. 1N HCl (50.0 mL) is added, and the aqueous phase is extracted with EtOAc (4×50.0 mL). The combined organic phases are dried over $MgSO_4$, filtered and concentrated on the rotovaporator. The product is purified by flash chromatography (CombiFlash), eluting with mixtures of heptanes and EtOAc (0% EtOAc to 30% EtOAc) (1.55 g, 7.38 mmol, 67%). $^1$H NMR (400 MHz, DMSO-D6) δ ppm 1.23-1.38 (m, 1H) 1.52-1.68 (m, 2H) 1.68-1.78 (m, 1H) 1.78-1.93 (m, 4H) 2.00-2.11 (m, 2H) 7.75 (d, J=8.79 Hz, 2H) 7.91 (d, J=8.79 Hz, 2H).

Step b Intermediate 33

Synthesis 1-[4-(1-aminoethyl)phenyl]cyclohexylcarbonitrile 4-(Cyanocyclohexyl)benzonitrile (1.55 g, 7.38 mmol) is mixed with THF (40.0 mL) and cooled to −78° C. under $N_2$ gas. MeLi (9.23 mL, 14.8 mmol, 1.60M in $Et_2O$) is added, and the mixture is stirred at −78° C. for 60 minutes. A mixture of $NaBH_4$ (558 mg, 14.8 mmol) in MeOH (40.0 mL) is added, and the solution is warmed to 0° C. for 2 hours. 1N HCl (50.0 mL) is added, and the solution is concentrated to dryness on the rotovaporator. The product is purified by HPLC: Gilson prep pumps, flow rate: 30 ml/min, column: Synergi Gemini (5u) 21.2×50 mm (high pH), mobile phase: A=water (10 mM $NH_4CO_3$) B=MECN, (510 mg, 2.24 mmol, 30%). $^1$H NMR (400 MHz, DMSO-D6) δ ppm 1.22 (d, J=6.64 Hz, 3H) 1.25-1.34 (m, 1H) 1.52-1.68 (m, 2H) 1.69-1.76 (m, 1H) 1.76-1.88 (m, 4H) 1.99-2.07 (m, 2H) 3.96 (q, J=6.51 Hz, 1H) 7.37-7.45 (m, 4H).

Scheme 12: Synthesis of (7-chloro-6-fluoro-1H-benzimidazol-1-yl)acetic acid.

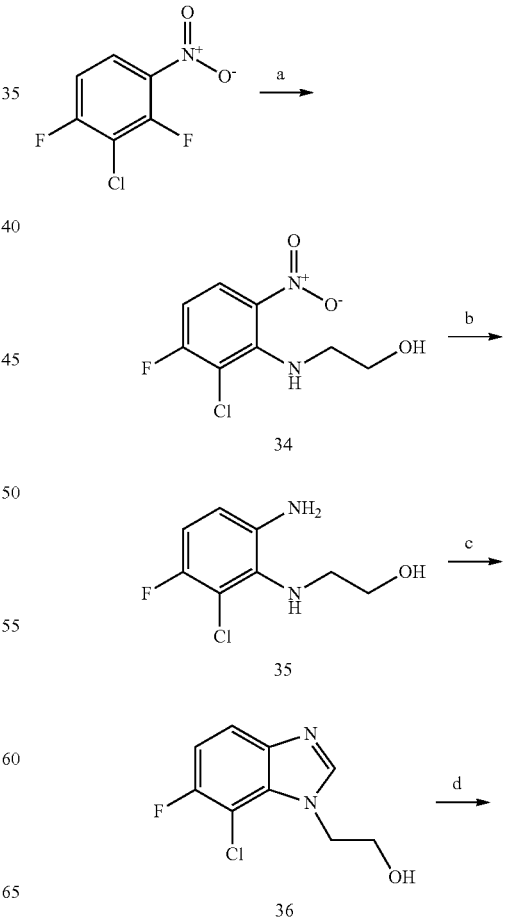

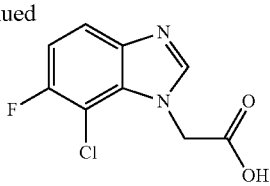

37

Step a Intermediate 34

2-[(2-Chloro-3-fluoro-6-nitrophenyl)amino]ethanol

2-Chloro-1,3-difluoro-4-nitrobenzene (5.37 g, 27.7 mmol), ethanolamine (1.69 g, 27.7 mmol) and Et₃N (2.80 g, 27.7 mmol) are stirred in EtOH (40.0 mL) at room temperature for 2 hours. The solvent is then evaporated, and the resulting residue is suspended in EtOAc (50.0 mL) and washed with 0.5 N NaOH (50.0 mL). The aqueous phase is extracted 4 times with EtOAc (4×50.0 mL). The combined organic phases are dried with MgSO₄, filtered and concentrated. The product is purified by flash chromatography on silica gel, eluting with mixtures of heptane and EtOAc (5.53 g, 85%). ¹H NMR (400 MHz, DMSO-D6) δ ppm 3.39 (dd, J=10.55, 5.27 Hz, 2H) 3.53 (t, J=5.47 Hz, 2H) 4.89 (s, 1H) 6.89 (dd, J=9.37, 8.01 Hz, 1H) 7.19 (t, J=4.69 Hz, 1H) 8.01 (dd, J=9.47, 5.96 Hz, 1H).

Step b Intermediate 35

2-[(6-Amino-2-chloro-3-fluorophenyl)amino]ethanol

2-[(2-Chloro-3-fluoro-6-nitrophenyl)amino]ethanol (5.52 g, 22.7 mmol) is dissolved in MeOH (40.0 mL). A premixed solution of Na₂S₂O₄ (13.8 g, 79.5 mmol) in water (40.0 mL) is added to the first solution. The resulting solution is stirred for 5 minutes at 60° C. followed by 2 hours at room temperature. The solvents are evaporated, and the resulting residue is suspended in a saturated solution of NaHCO₃ (40.0 mL). The aqueous phase is extracted 4 times with EtOAc (4×40.0 mL). The combined organic phases are dried with MgSO₄, filtered and concentrated. The product is sufficiently pure by ¹H NMR (2.07 g, 45%). ¹H NMR (400 MHz, DMSO-D6) δ ppm 2.99 (m, 2H) 3.32 (s, 1H) 3.48 (t, J=5.57 Hz, 2H) 4.09 (s, 1H) 4.73-4.95 (m, 2H) 6.55 (dd, J=8.79, 5.66 Hz, 1H) 6.71 (t, J=8.89 Hz, 1H).

Step c Intermediate 36

2-(7-chloro-6-fluoro-1H-benzimidazol-1-yl)ethanol

2-[(6-Amino-2-chloro-3-fluorophenyl)amino]ethanol (2.07 g, 10.2 mmol) is dissolved in formic acid (50.0 mL), and the resulting solution is heated to 100° C. for 1 hour. The solution is cooled to room temperature and then evaporated to dryness. The residue is suspended in NH₃ (50.0 mL, 2N in EtOH) and stirred for 1 hour. The solution is concentrated to dryness, and the residue is suspended in EtOAc (50.0 mL). The organic phase is washed with 2N NaOH (50.0 mL), and the resulting aqueous phase is extracted 4 times with EtOAc (4×50.0 mL). The combined organic phases are dried with MgSO₄, filtered and concentrated. The product is dissolved in EtOAc, filtered and recrystallized from EtOAc (895 mg, 41%). ¹H NMR (400 MHz, DMSO-D6) δ ppm 3.74 (t, J=5.27 Hz, 2H) 4.52 (t, J=5.47 Hz, 2H) 4.99 (s, 1H) 7.25 (dd, J=10.16, 8.79 Hz, 1H) 7.64 (dd, J=8.79, 4.49 Hz, 1H) 8.21 (s, 1H).

Step d Intermediate 37

(7-chloro-6-fluoro-1H-benzimidazol-1-yl)acetic Acid 2-(7-Chloro-6-fluoro-1H-benzimidazol-1-yl)ethanol (550 mg, 2.57 mmol) is dissolved in AcOH (20.0 mL). Jones reagent[a] (3.31 mL, 3.00 mmol, 0.907 M) is added drop wise, and the solution is stirred for 1 hour at room temperature. The solution is diluted with iPrOH (50.0 mL), and the solvents are evaporated. 6N NaOH is added to the solution until the pH is 11. The aqueous phase is washed with EtOAc (50.0 mL), and the organic phase is extracted 3 times with water (3×50.0 mL). The combined aqueous phases are acidified with 12N HCl until the pH is 3. The aqueous phase is then extracted 4 times with EtOAc (4×50.0 mL). The combined organic phases are dried with MgSO₄, filtered and concentrated. The product is sufficiently pure by ¹H NMR (236 mg, 40%). ¹H NMR (400 MHz, DMSO-D6) δ ppm 5.18 (s, 2H) 7.24 (dd, J=10.16, 8.79 Hz, 1H) 7.64 (dd, J=8.79, 4.49 Hz, 1H) 8.13-8.30 (m, 1H).

[a] Jones reagent is prepared by mixing 997 mg of CrO₃ in 1.00 mL of H₂SO₄ and 10.0 mL of water.

Alternative Preparation of (7-chloro-6-fluoro-1H-benzimidazo-1-yl)acetic Acid

Step 1. Synthesis of N-(2-chloro-3-fluoro-6-nitrophenyl)-glycine Methyl Ester

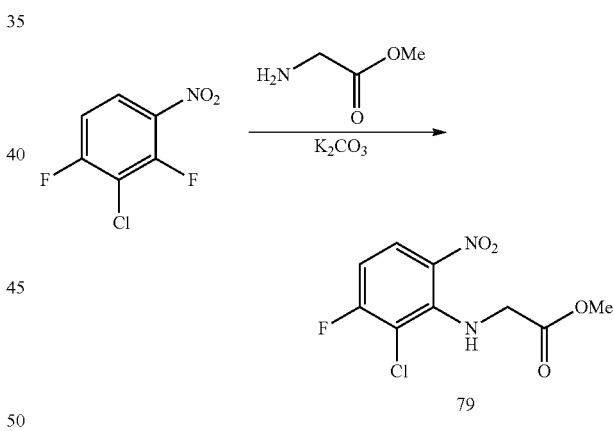

79

To a three neck round bottom flask equipped with a nitrogen bubbler and a thermometer is charged K₂CO₃ (40.0 g, 289.3 mmol), glycine methyl ester hydrochloride (17.4 g, 138.8 mmol) and 2-propanol (200 mL). The resulting mixture is stirred at room temperature for one hour. 3-Chloro-2,4-difluoronitrobenzene (22.4 g, 115.7 mmol, 1 eq) is charged to the reaction mixture which becomes a yellow colored slurry. This slurry is stirred at room temperature for a period of 18 h. The progress of the reaction mixture is monitored using ¹H NMR spectroscopy.

After confirming the completion of the reaction, the mixture is diluted with iPrOAc (560 mL) and 1M HCl (225 mL) is added dropwise to the above mixture (control the CO₂ evolution) under vigorous agitation. The dark yellow slurry turns into to a clear and colorless biphasic solution. The organic layer is separated and washed with 1M HCl (3×100 mL) and then is dried over MgSO₄. The drying agent is filtered and the filtrate is evaporated to dryness on the rotary evaporator to give the crude product as a yellow solid, (29.1 g), indicated by ¹H NMR to be extremely clean. ¹H NMR (400 MHz, CDCl₃) δ: 8.08 (ddd, 1H), 6.7 (m, 1H), 4.35 (s, 2H), 3.8 (s, 3H)

The reaction mixture is monitored by taking up an aliquot of the reaction mixture in iPrOAc, quenching it with 1N HCl, and then separating and evaporating the organic layer to dryness and analyzing the yellow solid obtained by ¹H NMR.

Step 2. Conversion of N-(2-chloro-3-fluoro-6-nitrophenyl)-glycine methyl ester to (7-chloro-6-fluoro-1H-benzimidazo-1-yl)acetic acid hydrochloride

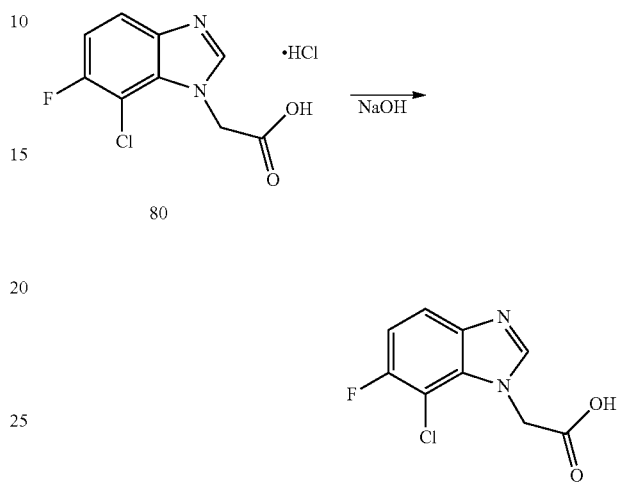

A Parr hydrogenation flask is charged with N-(2-chloro-3-fluoro-6-nitrophenyl) glycine methyl ester (15 g, 60.8 mmol) along with formic acid (150 mL). The resulting mixture is heated to ~50° C. to form a clear solution which is cooled back to room temperature. To this solution is added 5% Pd—C (0.6 g, 4% by weight) and the reaction mixture is hydrogenated at 40 psi for 3 h. The completion of the reaction is confirmed by ¹H NMR.

An identical reaction using 12.3 g (49.8 mmol) of N-(2-chloro-3-fluoro-6-nitrophenyl) glycine methyl ester, 125 mL of formic acid and 0.5 g of catalyst is also conducted.

After confirming the completion of the reaction, the reaction mixture from the above two experiments is filtered through a sintered glass funnel over a pad of celite. The filter cake is washed with hot formic acid (60° C.) until the filtrate becomes colorless. The filtrate is evaporated to dryness under reduced pressure and the brown precipitate obtained is dried in a vacuum oven at 60° C. for 3 h to give a brown solid. (24.2 g). The hydrogenation results in the formation of a mixture of products, which are converted to the benzimidazole as follows:

This crude material obtained is dissolved in formic acid (242 mL) and conc. HCl (242 mL). The resultant mixture is heated to reflux and kept for a period of 2 h. After confirmation of the completion of reaction by ¹H NMR, the reaction mixture is evaporated to dryness on a rotary evaporator. The solid residue obtained is taken up in 300 mL of MeCN to form a slurry which is again concentrated to dryness. The brown solid residue obtained is triturated with 300 mL MeCN at room temperature for a period of an hour. The solid is collected by filtration and dried in a vacuum oven at 60° C. for 18 h to give the desired product (23.2 g, 79%) as the hydrochloride salt. ¹H NMR (400 MHz, DMSO-d₆): δ 9.25 (s, 1H), 7.83 (dd, 1H), 7.52 (t, 1H), 5.5 (s, 2H).

Step 3. Isolation of the desired acid (7-chloro-6-fluoro-1H-benzimidazol-1-yl)acetic Acid

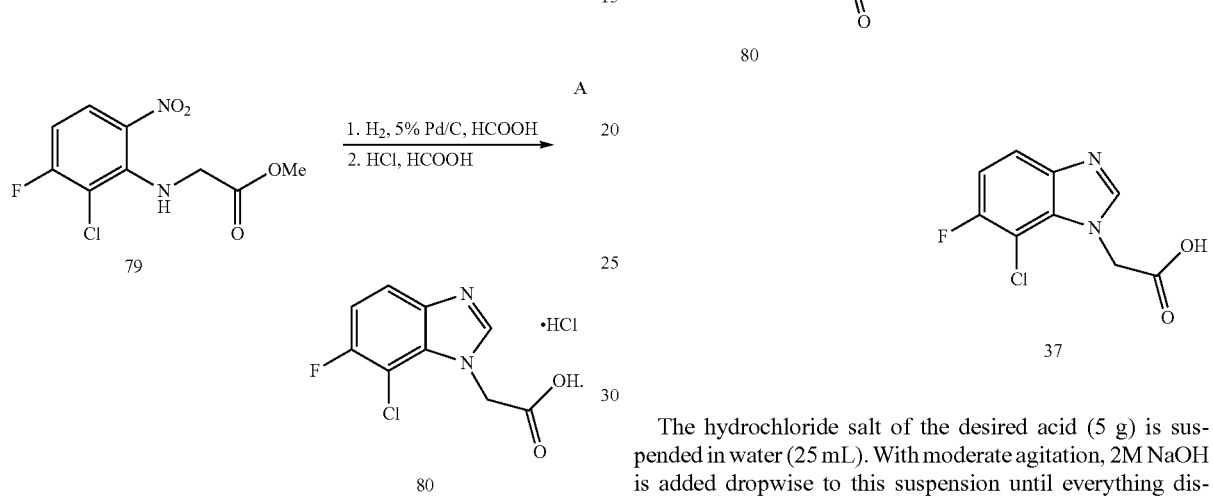

The hydrochloride salt of the desired acid (5 g) is suspended in water (25 mL). With moderate agitation, 2M NaOH is added dropwise to this suspension until everything dissolves to give a clear brown colored solution. This aqueous solution is washed with EtOAc (2×25 mL). The aqueous layer is separated and acidified by the dropwise addition of 1M HCl until the pH of the reaction mixture reaches ~4.2. A suspension is formed which is cooled to 0-5° C. by immersing in an ice-water bath and kept for one hour under moderate agitation. The solid is collected by filtration and the filter cake is air dried over the weekend to give the desired product 37 as a light brown solid (2.5 g, 60%).

Scheme 13: Synthesis of (6-chloro-7-fluoro-1H-benzimidazol-1-yl)acetic acid.

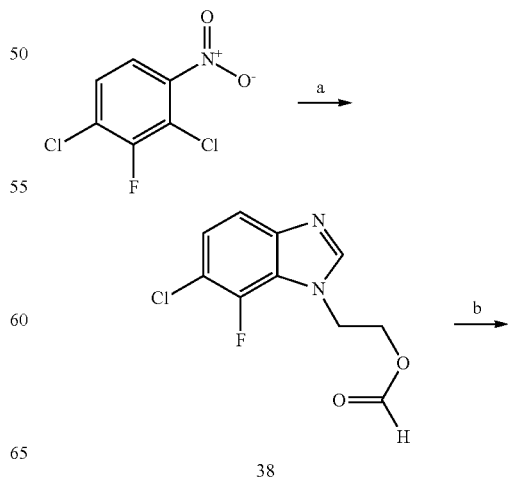

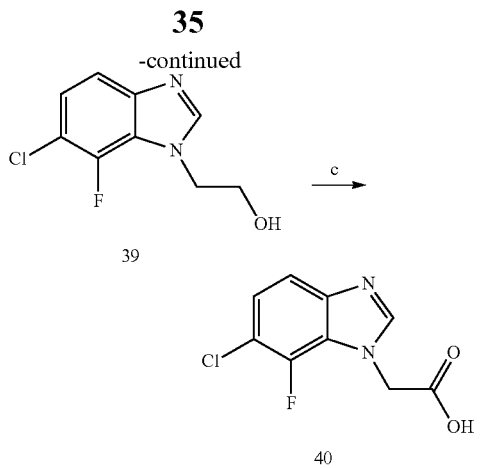

Step a Intermediate 38

2-(6-Chloro-7-fluoro-1H-benzimidazol-1-yl)ethyl Formate 1,3-Dichloro-2-fluoro-4-nitrobenzene (9.70 g, 46.2 mmol), ethanolamine (7.05 g, 231.0 mmol) are stirred in EtOH (25.0 mL) at 60° C. for 24 hours. The solvent is then evaporated, and the resulting residue is dissolved in MeOH (150.0 mL). A premixed solution of $Na_2S_2O_4$ (23.7 g, 136.4 mmol) in water (100 mL) is added to the first solution. The resulting solution is stirred for 30 minutes at 60° C. The solvents are evaporated, and the resulting residue is suspended in a saturated solution of $NaHCO_3$ (40.0 mL). The aqueous phase is extracted 4 times with EtOAc (4×100.0 mL). The combined organic phases are filtered and concentrated. The resulting crude material is heated at 100° C. in formic acid (60.0 mL) for 3 hours then stirred at room temperature for 18 h. The reaction mixture is concentrated under reduced pressure, to the resulting residue a conc. sodium bicarbonate solution (10 mL) is added and extracted with ethyl acetate (3×100 mL). The combined organic phases are dried with $MgSO_4$, filtered and concentrated. The resulting solid material is triturated with methanol to provide the expected product 2-(6-chloro-7-fluoro-1H-benzimidazol-1-yl)ethyl formate (2.2 g, 19%), 1H NMR (400 MHz, CHLOROFORM-D) δ ppm 4.49-4.62 (m, 2H) 4.64-4.77 (m, 2H) 7.31 (dd, J=8.59, 7.03 Hz, 1H) 7.46 (d, J=8.59 Hz, 1H) 8.02 (s, 1H) 8.23 (s, 1H)

Step b Intermediate 39

2-(6-Chloro-7-fluoro-1H-benzimidazol-1-yl)ethanol 2-(6-Chloro-7-fluoro-1H-benzimidazol-1-yl)ethyl formate (1.1 g, 4.53 mmol) is dissolved in MeOH (50.0 mL) with triethylamine (5.0 mL) and stirred at room temperature 18 hours. The reaction mixture is then concentrated to provide the expected product 2-(6-chloro-7-fluoro-1H-benzimidazol-1-yl)ethanol (0.95 g, 98%) as a white powder. 1H NMR (400 MHz, METHANOL-D4) δ ppm 3.90 (t, J=4.69 Hz, 2H) 4.47 (t, J=5.08 Hz, 2H) 7.30 (dd, J=8.79, 6.84 Hz, 1H) 7.45 (dd, J=8.59, 0.78 Hz, 1H) 8.16-8.19 (m, 1H)

Step c Intermediate 40

(6-Chloro-7-fluoro-1H-benzimidazol-1-yl)acetic Acid 2-(6-chloro-7-fluoro-1H-benzimidazol-1-yl)ethanol (800 mg, 3.74 mmol) is taken into 40 ml of MeCN and sodium phosphate buffer (30 ml, 0.67 M, pH 6.8) and the mixture is heated to 36° C. TEMPO (174 mg, 1.12 mol) is added followed by the simultaneous dropwise addition of a solution of $NaClO_2$ (201 mg, 80% pure, 2.23 mmol in 15 ml water) and a solution of bleach (500 μL of 6% NaOCl solution) over 2 hours. After 24 hours the reaction mixture is allowed to cool to room temperature followed by the dropwise addition a saturated solution of $Na_2SO_3$. Using conc. HCl the pH is lowered to 1 and a white powder precipitates out which is filtered and washed with a few drops of distilled water. The resulting solid is dried under vacuum to provide the expected product (7-chloro-6-fluoro-1H-benzimidazol-1-yl)acetic acid (540 mg, 63%) as a white powder. 1H NMR (400 MHz, METHANOL-D4) δ ppm 4.08 (s, 2H) 6.50 (dd, J=8.59, 7.03 Hz, 1H) 6.66 (d, J=8.59 Hz, 1H) 7.37 (s, 1H)

Scheme 14: Synthesis of 4-[4-(1-aminoethyl)-3-methylphenyl]tetrahydro-2H-thiopyran-4-carbonitrile

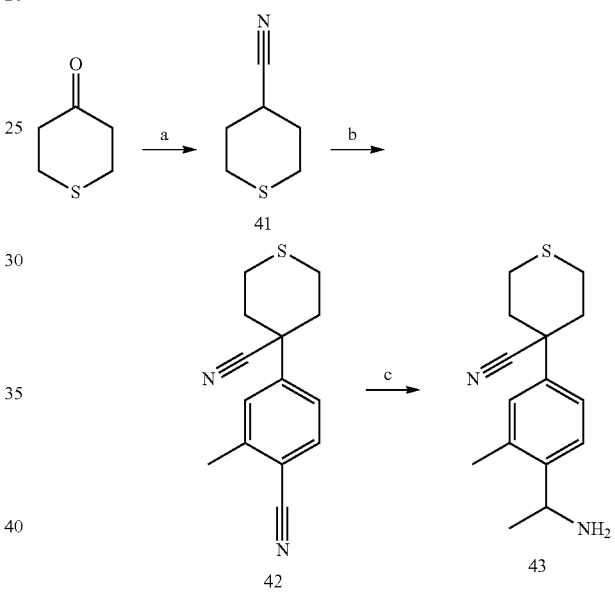

Step a Intermediate 41

Tetrahydro-2H-thiopyran-4-carbonitrile

A mixture of tetrahydro-4H-thiopyran-4-one (8.0 g, 68.9 mmol), tosylmethyl isocyanate (14.76 g, 75.6 mmol) and 1,2-dimethoxyethane (400 mL) is stirred under nitrogen at 0° C. in an ice bath while a solution of t-BuOK in THF (1.0M, 15.1 mmol) is slowly added via syringe. The mixture is allowed to warm to room temperature with stirring over a period of 5 hours. The contents are again cooled to 0° C. in an ice bath and water (10.0 mL) is added to quench the reaction. The solvent is removed by rotary evaporator and EtOAc (100 mL) and saturated aqueous $NaHCO_3$ (100 mL) are added to the vessel. The phases are separated and the organic is washed with brine, dried with $Na_2SO_4$ and concentrated to a residue that is purified by silica gel column chromatography (EtOAc/hexanes) to yield the product (3.5 g, 27.6 mmol, 41%). $^1$H NMR (400 MHz, DMSO-D6) δ ppm 1.79-1.94 (m, 2H), 1.97-2.14 (m, 2H), 2.51-2.73 (m, 4H), 2.96-3.10 (m, 1H).

Step b Intermediate 42

4-(4-Cyano-3-methylphenyl)tetrahydro-2H-thiopyran-4-carbonitrile

A solution of tetrahydro-2H-thiopyran-4-carbonitrile (197 mg, 1.55 mmol) and THF (2.0 mL) is slowly added via syringe to a mixture of KHMDS (324 mg, 1.63 mmol) in THF (3.0 mL), stirring at −78° C. under nitrogen. The temperature is maintained at −78° C. for 30 min. before a mixture of 4-fluoro-2-methylbenzonitrile (222 mg, 1.64 mmol) in THF (1.0 mL) is slowly added to the vessel. The mixture is allowed to warm to room temperature and is stirred for 3 hours before being quenched with saturated aqueous NH$_4$Cl. The solvent is removed by rotary evaporator and EtOAc (10.0 mL) and water (10.0 mL) are added. The phases are partitioned and the organic is washed with brine, dried with Na$_2$SO$_4$ and concentrated to yield the product (252 mg, 1.04 mmol, 67%). $^1$H NMR (400 MHz, DMSO-D6) δ ppm 1.84-1.95 (m, 2H), 2.03-2.14 (m, 2H), 2.51 (s, 3H), 2.57-2.72 (m, 4H), 7.23-7.31 (m, 1H), 7.41 (dd, J=9.96, 1.76 Hz, 1H), 7.89 (dd, J=8.59, 5.86 Hz, 1H).

Step c Intermediate 43

4-[4-(1-aminoethyl)-3-methylphenyl]tetrahydro-2H-thiopyran-4-carbonitrile 4-(4-Cyano-3-methylphenyl)tetrahydro-2H-thiopyran-4-carbonitrile (983 mg, 4.06 mmol) is stirred in THF (40.0 mL) at −78° C. under nitrogen as a 1.6 M solution of methyllithium in Et$_2$O is added slowly via syringe to the vessel. The contents are stirred for 3 hours at −20° C. before being quenched with MeOH (40.0 mL) and warmed to room temperature. NaBH$_4$ (460 mg, 12.2 mmol) is slowly added at 0° C. in an ice bath and the mixture is warmed to room temperature and stirred for 16 hours. 1.0 N aqueous HCl is added until a pH of 3.0 is reached and the solvent is removed by rotary evaporator. To the residue is added concentrated aqueous HCl (3.0 mL) and the mixture is stirred for 16 hours. The contents are neutralized with 1.0 M aqueous NaOH and EtOAc (40.0 mL) is added. The layers are separated and the organic is dried with Na$_2$SO$_4$ and concentrated to a residue that is purified by silica get column chromatography (10% MeOH in DCM) (253 mg, 1.05 mmol, 26%).

Scheme 15: Synthesis of 2-[4-(1-aminoethyl)-3-methylphenyl]-2-methylpropanenitrile

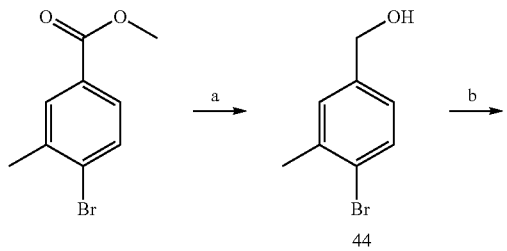

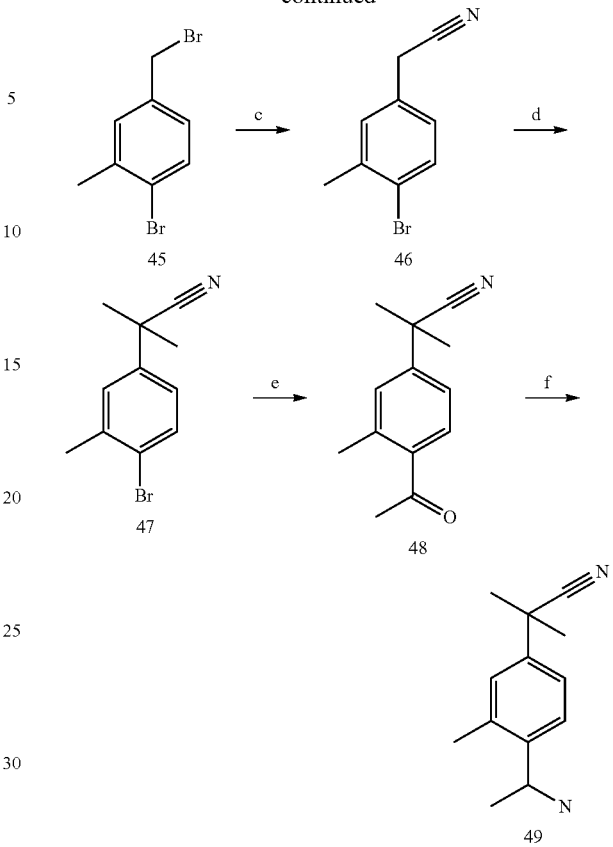

Step a Intermediate 44

(4-Bromo-3-methylphenyl)methanol

Methyl 4-bromo-3-methylbenzoate (17.0 g, 74.2 mmol) is dissolved in anhydrous THF (100 mL). The solution is cooled to 0° C. and a 2 M solution of lithium aluminum hydride in THF (40 mL) is added to the mixture. The solution is left stirring 30 min. at this temperature. A cold HCl solution is then added drop wise to the reaction mixture until dissolution of the aluminum complex. The desired product is extracted with ethyl acetate, the organic phase is washed with brine (200 mL), dried with MgSO$_4$ and concentrated in vacuo. to provide the expected product (4-Bromo-3-methylphenyl)methanol (14.4 g, 97%) as a clear yellow oil, pure by proton NMR, and is used as such in the next step. 1H NMR (400 MHz, CHLOROFORM-D) δ ppm 2.40 (s, 3 H) 4.61 (s, 2H) 6.89-7.10 (m, J=8.20, 1.56, 0.59 Hz, 1H) 7.23 (d, J=2.34 Hz, 1H) 7.50 (d, J=8.20 Hz, 1H)

Step b Intermediate 45

1-Bromo-4-(bromomethyl)-2-methylbenzene (4-Bromo-3-methylphenyl)methanol (14.4 g, 71.6 mmol) is dissolved in anhydrous CH$_2$Cl$_2$ (150 mL) and CBr$_4$ (26.1 g, 79.0 mmol) is added. The reaction mixture is cooled to 0° C. and PPh$_3$ (20.7 g, 79.0 mmol) is added in small portions. The reaction mixture is stirred 2 h and the triphenylphosphine oxide that forms is filtered off and the solvent removed in vacuo. The resulting semi solid is filtered on a silica gel pad and rinsed with hexane/EtOAc (9:1) to provide the expected product 1-Bromo-4-(bromomethyl)-2-methylbenzene as a clear oil contaminated with bromoform which is used directly in the next step. 1H NMR (400 MHz, CHLOROFORM-D) δ ppm 4.39-4.44 (m, 3H) 7.07 (dd, J=8.20, 2.34 Hz, 1H) 7.26 (t, J=1.17 Hz, 1H) 7.49 (d, J=8.20 Hz, 1H)

Step c Intermediate 46

2-(4-bromo-3-methylphenyl)acetonitrile

1-Bromo-4-(bromomethyl)-2-methylbenzene (45 of crude from step b, 68.2 mmol) dissolved in $CH_2Cl_2$ (500 mL) is mixed and stirred with potassium cyanide (24 g, 364 mmol) and N-tetra(n-butyl)ammonium bromide (1.2 g, 3.64 mmol) in distilled water (500 mL). This reaction mixture is stirred vigorously for 6 h. The organic phase is separated, dried over $MgSO_4$, filtered and concentrated. The resulting residue is purified on silica gel using a 0 to 30% gradient of ethyl acetate in heptane to provide the expected product 2-(4-bromo-3-methylphenyl)acetonitrile (12.4 g, 87% over two steps) as a clear yellow oil. 1H NMR (400 MHz, CHLOROFORM-D) δ ppm 2.41 (s, 3H) 3.68 (s, 2H) 7.01 (dd, J=8.50, 2.05 Hz, 1H) 7.21 (d, J=1.37 Hz, 1H) 7.53 (d, J=8.20 Hz, 1H)

Step d Intermediate 47

2-(4-bromo-3-methylphenyl)-2-methylpropanenitrile

To a stirred solution of 2-(4-bromo-3-methylphenyl)acetonitrile (11.2 g, 53.3 mmol) in anhydrous DMF (125 mL) is added methyl iodide (13.2 mL, 213 mmol). The solution is cooled to 0° C. and sodium hydride (60% susp. in oil, 3.84 g, 160 mmol) is added in small portions over 20 min. The reaction mixture is then left stirring and slowly warmed up to room temperature for 18 h. At 0° C., water (500 mL) is then slowly added then extracted with ethyl acetate containing 10% of hexanes. The organic layer is separated, dried with $MgSO_4$, filtered and concentrated under reduced pressure to provide the expected product 2-(4-bromo-3-methylphenyl)-2-methylpropanenitrile (12.6 g, 99%) as a clear yellow oil which is used in the next step without further purification. 1H NMR (400 MHz, CHLOROFORM-D) δ ppm 1.71 (s, 6H) 2.43 (s, 3H) 7.14 (dd, J=8.40, 2.34 Hz, 1H) 7.34 (d, J=2.54 Hz, 1H) 7.53 (d, J=8.40 Hz, 1H)

Step e Intermediate 48

2-(4-acetyl-3-methylphenyl)-2-methylpropanenitrile

To a stirred solution of 2-(4-bromo-3-methylphenyl)-2-methylpropanenitrile (5.0 g, 21.0 mmol) in anhydrous THF (75 mL) at −100° C. is added n-butyllithium (2 M in c-hexane) (21 mL, 42 mmol). This reaction mixture is stirred at that temperature 5 min., then N-methoxy-N-methyl-acetamide (4.33 g, 42 mmol) is added. The solution is then warmed up to room temperature over 1 h. Acidic brine (30 mL of brine, 15 mL of 3% HCl aq) is then slowly added and the solution is extracted with EtOAc (3×100 mL). The organic layer is dried over $MgSO_4$, filtered and concentrated under reduced pressure. The crude product is purified on silica gel using a 0 to 30% gradient of EtOAc in heptane to provide the expected product 2-(4-acetyl-2-methylphenyl)-2-methylpropanenitrile (1.0 g, 24%). 1H NMR (400 MHz, CHLOROFORM-D) δ ppm 1.71 (s, 6 H) 2.53 (s, 3H) 2.56 (s, 3H) 7.30-7.38 (m, 2H) 7.70 (d, J=8.01 Hz, 1H)

Step f Intermediate 49

2-[4-(1-aminoethyl)-3-methylphenyl]-2-methylpropanenitrile

To a stirred solution of 2-(4-acetyl-3-methylphenyl)-2-methylpropanenitrile (1.0 g, 4.97 mmol) in 7 M ammonia in MeOH (40 mL) is added titanium (IV) isopropoxide (3.0 g, 9.95 mmol). The reaction mixture is left stirring 24 h at room temperature. After cooling to 0° C., sodium borohydride (1.0 g, 19.9 mmol) is added and the reaction mixture stirred and left to warm-up to room temperature 1 h. Conc. ammonium hydroxide (15 mL) is then added and the titanium oxide is removed by filtration and is washed with ethyl acetate. The filtrate is extracted with EtOAc (2×100 mL) and the combined organic layers are dried over $MgSO_4$, filtered and concentrated under reduced to provide the expected product 2-[4-(1-aminoethyl)-3-methylphenyl]-2 methylpropanenitrile (1.0 g, 99%) as a clear yellow oil. 1H NMR (400 MHz, CHLOROFORM-D) δ ppm 1.33 (d, J=6.64 Hz, 3H) 1.44 (s, 2H) 1.70 (s, 6H) 2.36 (s, 3H) 4.34 (q, J=6.44 Hz, 1 H) 7.22 (d, J=1.95 Hz, 1H) 7.28 (dd, J=8.20, 2.15 Hz, 1H) 7.48 (d, J=8.20 Hz, 1H)

Scheme 16:
Synthesis of 2-[4-(1-aminoethyl)-2-methylphenyl]-2-methylpropanenitrile

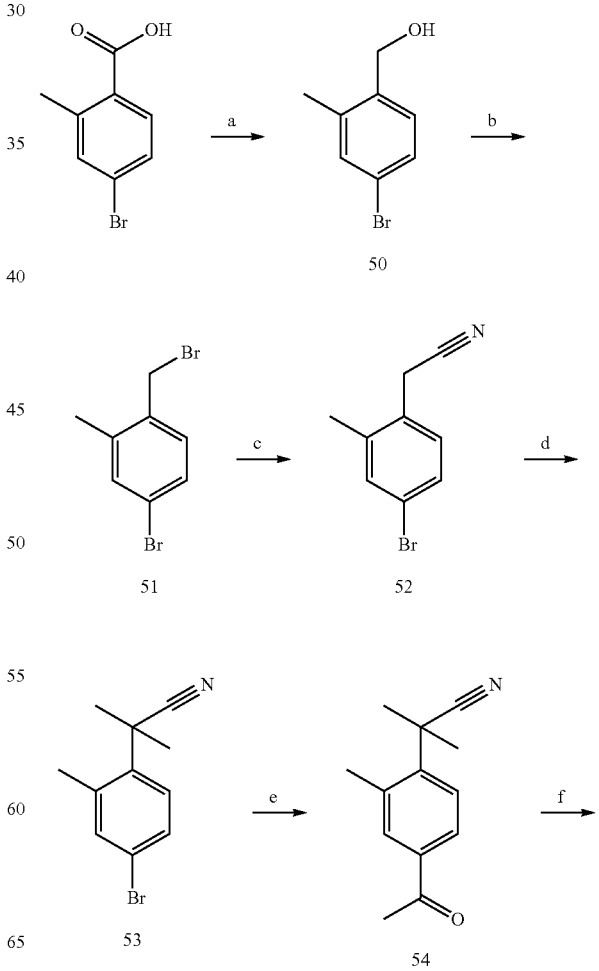

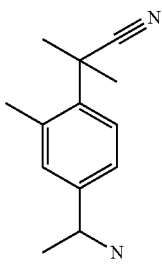

Step a, Intermediate 50

(4-Bromo-2-methylphenyl)methanol

4-Bromo-2-methylbenzoic acid (11.1 g, 51.6 mmol) is dissolved in anhydrous THF (11.2 mL). The solution is cooled to 0-5° C. and a 1 M solution of BH$_3$.THF (103 mL) is added to the mixture. The solution is left stirring 3 h at room temperature. Cold water is then added (20 mL) and the reaction mixture is washed with a saturated solution of NaHCO$_3$ (120 mL). The aqueous phase is extracted with diethyl ether (3×300 mL) and the combined organic phases washed with brine (200 mL), dried with MgSO$_4$ and concentrated in vacuo. The resulting oil is purified by flash-chromatography, eluting with hexane/EtOAc from 95:5 to 70:30, to provide the expected product (4-Bromo-2-methylphenyl)methanol (10.4 g, 100%) as a clear oil.

1H NMR (300 MHz, CHLOROFORM-D): δ 7.36-7.30 (2H, m), 7.25-7.21 (1H, m), 4.65 (2H, s) 2.32 (3H, s).

Step b Intermediate 51

1-Bromo-4-(bromomethyl)-3-methylbenzene (4-Bromo-2-methylphenyl)methanol (10.4 g, 51.6 mmol) is dissolved in anhydrous CH$_2$Cl$_2$ (150 mL) and CBr$_4$ (18.8 g, 56.8 mmol) added. The reaction mixture is cooled to 0-5° C. and PPh$_3$ (14.9 g, 56.8 mmol) is added. The reaction mixture is stirred overnight then hexane/EtOAc (9:1) (250 mL) is added with vigorous stirring. The triphenylphosphine oxide that forms during the reaction is filtered off and the filtrates are concentrated in vacuo. The resulting oil is purified on a silica gel pad with hexane/EtOAc (8:2). The solvent are removed on a rotary evaporator and the bromoform is removed by vacuum distillation (15 mm Hg, bp: 40-50° C.) to provide the expected product 1-Bromo-4-(bromomethyl)-3-methylbenzene (13.23 g, 97%) as a yellow oil. 1H NMR (300 MHz, CHLOROFORM-D): δ 7.37-7.27 (2H, m), 7.17 (1H, d, J=8.1 Hz), 4.45 (2H, s), 2.39 (3H, s).

Step c Intermediate 52

2-(4-bromo-2-methylphenyl)acetonitrile

1-Bromo-4-(bromomethyl)-3-methylbenzene (13.2 g, 50.1 mmol) is dissolved in DMF (65 mL). The reaction mixture is cooled to 0-5° C. and NaCN (3.66 g, 74.6 mmol) is added follow by water (8 mL). The reaction is stirred overnight at room temperature and water (170 mL) is added followed by NaHCO$_3$ sat. (130 mL) and hexane/Et$_2$O (2:1) (150 mL). The organic phase is separated and the aqueous phase extracted with hexane/Et$_2$O (2:1) (3×150 mL). The combined organic phases are washed with water (170 mL), dried over MgSO$_4$, filtered and concentrated under reduced pressure to provide the expected product 2-(4-bromo-2-methylphenyl)acetonitrile (9.76 g, 93%) as an orange oil. 1H NMR (300 MHz, CHLOROFORM-D): δ 7.40-7.32 (2H, m), 7.23 (2H, d, J=8.2 Hz), 3.61 (2H, s), 2.32 (3H, s).

Step d Intermediate 53

2-(4-bromo-2-methylphenyl)-2-methylpropanenitrile

To a stirred solution of 2-(4-bromo-2-methylphenyl)acetonitrile (3.93 g, 18.8 mmol) in anhydrous DMF (35 mL) is added methyl iodide (2.45 mL, 39.4 mmol). The solution is cooled to 0° C. and sodium hydride (60% susp. in oil, 1.47 g, 61.1 mmol) is added in 3 equal portions over 20 min. The reaction mixture is then left stirring and slowly warmed up to room temperature for 18 h. The solution turned to a thick brown-orange paste. At 0° C., water (50 mL) is then slowly added and the solution is extracted with a 2:1 solution of hexane/Et2O (3×50 mL). The organic layer is washed with brine, dried with MgSO$_4$, filtered and concentrated under reduced pressure. The crude is purified by flash-chromatography, eluting with hexane/EtOAc (9:1) to provide the expected product 2-(4-bromo-2-methylphenyl)-2-methylpropanenitrile (3.1 g, 66%) as a clear yellowish oil. 1H NMR (300 MHz, CHLOROFORM-D): δ 7.40-7.30 (2H, m), 7.16 (2H, d, J=8.5 Hz), 2.63 (3H, s), 1.77 (6H, s).

Step e Intermediate 54

2-(4-acetyl-2-methylphenyl)-2-methylpropanenitrile

To a stirred solution of 2-(4-bromo-2-methylphenyl)-2-methylpropanenitrile (3.1 g, 13.0 mmol) in anhydrous THF (75 mL) at −78° C. is added n-butyllithium (2 M in c-hexane) (7.16 mL, 14.3 mmol). This reaction mixture is stirred at that temperature 10 min., then N-methoxy-N-methyl-acetamide (2.77 mL, 26.0 mmol) is added and the solution is then warmed up to room temperature over 1 h. Acidic brine (30 mL of brine, 15 mL of 3% HCl aq) is then slowly added and the solution extracted with EtOAc (3×100 mL). The organic layer is dried with MgSO$_4$, filtered and concentrated under reduced pressure. The crude product is purified by flash-chromatography using a 5 to 20% EtOAc in hexane gradient to provide the expected product 2-(4-acetyl-2-methylphenyl)-2-methylpropanenitrile (1.77 g, 68%) as a yellowish oil. 1H NMR (300 MHz, CHLOROFORM-D): δ 7.84-7.74 (2H, m), 7.43-7.40 (1H, m), 2.70 (3H, s), 2.60 (3H, s), 1.81 (6H, s).

Step f Intermediate 55

2-[4-(1-aminoethyl)-2-methylphenyl]-2-methylpropanenitrile

To a stirred solution of 2-(4-acetyl-2-methylphenyl)-2-methylpropanenitrile (1.77 g, 8.80 mmol) in 7 M ammonia in MeOH (45 mL) is added freshly distilled titanium (IV) isopropoxide (5.20 mL, 17.6 mmol). The reaction mixture is left stirring 18 h at room temperature. After cooling to 0° C., sodium borohydride (500 mg, 13.2 mmol) is added and the reaction mixture stirred at 0° C. until no more gas evolved and then at room temperature 3 h. Water (25 mL) is then added and the titanium oxide removed by filtration on a Buchner funnel. The filtrate is extracted with EtOAc (3×100 mL) (brine (10 mL) is added to help separation between both layers) and the combined organic layers are concentrated under reduced pressure. The resulting crude product (which contained water) is dissolved in Et$_2$O (75 mL), washed with brine, dried over MgSO$_4$ and filtered. 5-6 N HCl in 2-propanol (2.2 mL) is slowly added to the well-stirred filtrate. The resulting white precipitate is filtered on a Buchner funnel and dried in vacuo to provide the expected product 2-[4-(1-aminoethyl)-2-methylphenyl]-2-methylpropanenitrile (1.58 g, 75%) as a white solid. 1H NMR (300 MHz, CD3OD): δ 7.55 (1H, d, J=8.0 Hz), 7.44-7.37 (2H, m), 4.97 (3H, s), 4.52 (1H, q, J=6.9 Hz), 2.75 (3H, s), 1.86 (6H, s), 1.69 (3H, d, J=6.9 Hz).

Scheme 17
Synthesis of 2-[4-(1-aminoethyl)-2-chlorophenyl]-2-methylpropanenitrile

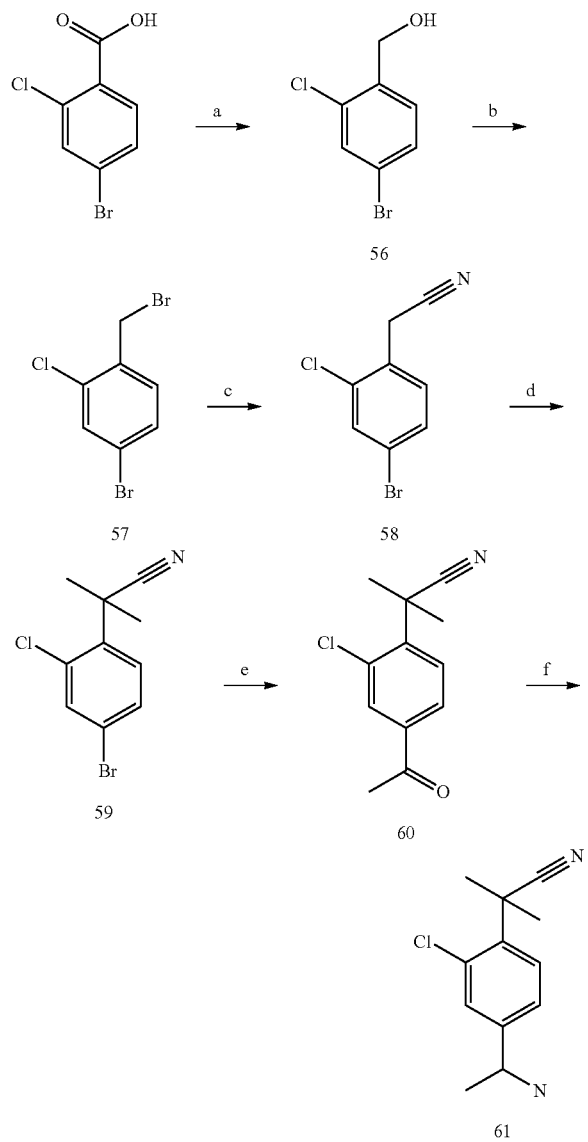

Step a Intermediate 56

(4-Bromo-2-chlorophenyl)methanol

To a stirred solution of 4-bromo-2-chlorobenzoic acid (4.27 g, 18.1 mmol) in tetrahydrofuran (39 mL) at 0° C. is added borane-tetrahydrofuran complex (1 M in THF) (36.3 mL, 36.3 mmol). The reaction mixture is stirred 16 h at room temperature. At 0° C., water is slowly added then NaHCO$_3$ aq. sat. is also slowly added The resulting solution is extracted with EtOAc (3×50 mL). The combined organic layer is washed with brine, dried over anhydrous MgSO$_4$, filtered and concentrated under reduced pressure. The crude product is purified by flashchromatography (eluent: Hexanes/EtOAc 85:15 to 70:30) to provide the expected product (4-bromo-2-chlorophenyl)methanol (4.34 g, 108%). 1H NMR (300 MHz, CHLOROFORM-D): δ 7.53 (1H, d, J=1.8 Hz), 7.43 (1H, dd, J=8.2, 1.8 Hz), 7.38 (1H, d, J=8.2 Hz), 4.74 (2H, d, J=6.2 Hz), 1.90 (1H, t, J=6.3 Hz).

Step b Intermediate 57

4-bromo-1-(bromomethyl)-2-chlorobenzene

To a stirred solution of (4-bromo-2-chlorophenyl)methanol (4.34 g, 19.6 mmol) in dichloromethane (98 mL) at 0° C. is added carbon tetrabromide (6.5 g, 19.6 mmol) and triphenylphosphine (5.14 g, 19.6 mmol). The reaction mixture is stirred 16 h at room temperature. Then, the solvent is removed and the crude solid suspended in hexanes/EtOAc 9:1 (100 mL) and filtered on a silica gel pad. The pad is rinsed with hexanes/EtOAc 9:1 (100 mL) and the filtrate is concentrated in vacuo to provide the expected product 4-bromo-1-(bromomethyl)-2-chlorobenzene (7.19 g, 129%) contaminated with bromoform. 1H NMR (300 MHz, CHLOROFORM-D): δ 7.57 (1H, d, J=2.0 Hz), 7.39 (1H, dd, J=8.2, 2.0 Hz), 7.30 (1H, d, J=8.2 Hz), 4.53 (2H, s).

Step c Intermediate 58

2-(4-Bromo-2-chlorophenyl)acetonitrile

To a stirred solution of 4-bromo-1-(bromomethyl)-2-chlorobenzene (7.19 g, 25.3 mmol) in dichloromethane (60 mL) and water (60 mL) is added tetrabutylammonium bromide (0.82 g, 2.53 mmol). Potassium cyanide (4.94 g, 75.8 mmol) in water (60 mL) is then added. The resulting solution is stirred 4 h at room temperature and quickly turned orange. A saturated solution of NaHCO$_3$ aq. is then added and the mixture extracted with CH$_2$Cl$_2$ (3×100 mL). The combined organic layer is washed with brine, dried over anhydrous MgSO$_4$ and filtered on a silica gel pad. The pad is rinsed with CH$_2$Cl$_2$ and the filtrate concentrated under reduced pressure to provide the expected product 2-(4-bromo-2-chlorophenyl)acetonitrile (5.38 g, 92%) contaminated with bromoform. 1H NMR (300 MHz, CHLOROFORM-D): δ 7.60 (1H, d, J=1.9 Hz), 7.47 (1H, dd, J=8.3, 1.9 Hz), 7.39 (1H, d, J=8.3 Hz), 3.79 (2H, s).

Step d Intermediate 59

2-(4-Bromo-2-chlorophenyl)-2-methylpropanenitrile

To a stirred solution of 2-(4-bromo-2-chlorophenyl)acetonitrile (1.11 g, 4.82 mmol) in anhydrous DMF (7.6 mL) is added methyl iodide (0.63 mL, 10.1 mmol). The solution is cooled to 0° C. and sodium hydride (60% susp. in oil, 0.63 g, 15.7 mmol) is added in 5 portions over 1 h. The reaction mixture is then left stirring to slowly warm up to room temperature for 18 h. The solution turned to a thick and brown orange paste. Water (20 mL) is then slowly added and the solution extracted with a 3:1 solution of hexane/Et$_2$O (3×25 mL). The organic layer is washed with brine, dried over MgSO$_4$, filtered and concentrated under reduced pressure. The crude product is purified by flash chromatography (eluent: Hex/EtOAc 9:1 to 8:2) to provide the expected product 2-(4-bromo-2-chlorophenyl)-2-methylpropanenitrile (0.79 g, 63%). 1H NMR (300 MHz, CHLOROFORM-D): δ 7.61 (1H, d, J=2.1 Hz), 7.43 (1H, dd, J=8.5, 2.1 Hz), 7.34 (1H, d, J=8.6 Hz), 1.85 (6H, s).

Step e Intermediate 60

2-(4-Acetyl-2-chlorophenyl)-2-methylpropanenitrile

To a stirred solution of 2-(4-bromo-2-chlorophenyl)-2-methylpropanenitrile (2.85 g, 11.0 mmol) in anhydrous THF (60 mL) at −78° C. is added n-butyllithium (2 M in c-hexane) (60.1 mL, 12.1 mmol). The reaction mixture is stirred at this temperature 10 min., then N-methoxy-N-methyl-acetamide (2.34 mL, 22.0 mmol) is added neat and the solution is stirred 10 min. at −78° C. and then warmed up to room temperature for another hour. Acidic brine (60 mL) is then slowly added and the solution is extracted with EtOAc (3×60 mL). The organic layer is dried over MgSO$_4$, filtered and concentrated under reduced pressure. The crude product is purified by flash chromatography (eluent: Hex/EtOAc 1:0 to 7:3) to provide the expected product 2-(4-acetyl-2-chlorophenyl)-2-methylpropanenitrile (1.57 g, 64%) as a yellow oil. 1H NMR (300 MHz, CHLOROFORM-D): δ 7.96 (1H, d, J=1.9 Hz), 7.81 (1H, dd, J=8.3, 1.9 Hz), 7.55 (1H, d, J=8.3 Hz), 2.56 (3H, s), 1.85 (6H, s).

Step f, Intermediate 61

2-(4-(1-Aminoethyl)-2-chlorophenyl)-2-methylpropanenitrile Hydrochloride

To a stirred solution of 2-(4-acetyl-2-chlorophenyl)-2-methylpropanenitrile (1.57 g, 7.08 mmol) in 7 M ammonia in methanol solution (35 mL) is added freshly distilled titanium (IV) isopropoxide (4.2 mL, 14.2 mmol). The reaction mixture is left stirring 18 h at room temperature. After cooling to 0° C., sodium borohydride (0.40 g, 10.6 mmol) is added and the reaction mixture is stirred at 0° C. until no more gas evolved and then at room temperature for 4 h. Water (40 mL) is then added and the titanium oxide is removed by filtration on a Buchner funnel. The filtrate is extracted with EtOAc (3×50 mL) and the combined organic layers are concentrated under reduced pressure. The resulting residue is dissolved in Et$_2$O (200 mL), washed with brine, dried over anhydrous MgSO$_4$ and filtered. To this solution is then added 5 N HCl in 2-propanol (1.8 mL, 8.85 mmol). The resulting precipitate is filtered on a Buchner funnel and dried to provide the desired 2-(4-(1-aminoethyl)-2-chlorophenyl)-2-methylpropanenitrile hydrochloride (1.17 g, 64%) as a white solid. 1H NMR (300 MHz, CD$_3$OD): δ 7.69 (1H, d, J=10.7 Hz), 7.68 (1H, s), 7.52 (1H, dd, J=8.3, 2.0 Hz), 4.53 (1H, q, J=6.8 Hz), 1.90 (6H, s), 1.66 (3H, d, J=6.9 Hz). 13C NMR (75 MHz, CD3OD): δ 142.5, 140.2, 136.0, 132.0, 130.1, 127.9, 52.0, 37.8, 28.4, 21.3.

Scheme 18 Synthesis of 2-[4-(aminomethyl)phenyl]-2-methylpropanenitrile

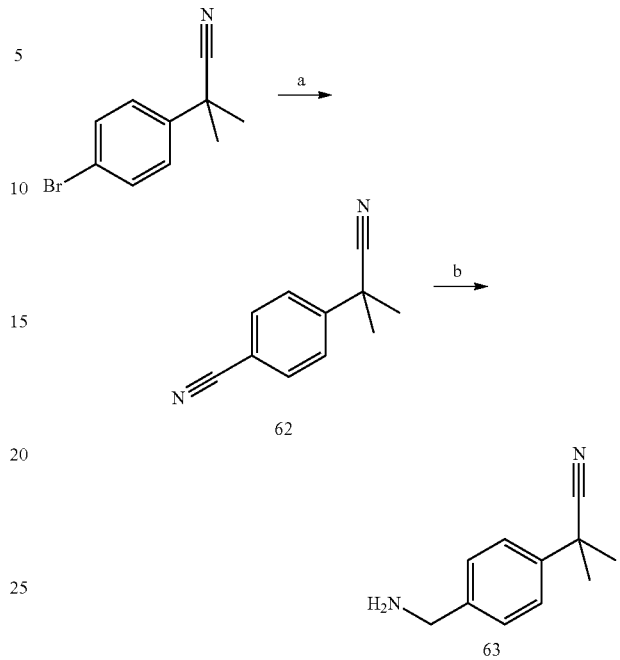

Step a, Intermediate 62

4-(1-cyano-1-methylethyl)benzonitrile 2-methyl-2-(4-methylphenyl)propanenitrile (3.51 g, 15.7 mmol) is dissolved in dry DMF (10 mL). Zn(CN)$_2$ (2.02 g, 17.2 mmol) and Pd(PPh$_3$)$_4$ (906 mg, 5 mol %) are added and the mixture heated at 100° C. for 3 hours. The reaction mixture is diluted with water and the solid recovered by filtration. The solid residue is dissolved in methanol, filtered to remove insoluble impurities, concentrated under vacuo and purified by normal phase MPLC (SiO$_2$, hexane to EtOAc), giving 4-(1-cyano-1-methylethyl)benzonitrile (2.28 g, 13.4 mmol, 85%) as a white solid. $^1$H NMR (400 MHz, DMSO-D6) δ ppm 1.70 (s, 6H) 7.73 (dt, J=8.64, 2.03 Hz, 2H) 7.92 (dt, J=8.69, 2.00 Hz, 2H).

Step b, Intermediate 63

2-[4-(aminomethyl)phenyl]-2-methylpropanenitrile 4-(1-cyano-1-methylethyl)benzonitrile (2.28 g, 13.41 mmol) is dissolved in dry THF and the solution cooled to 0° C. Red-Al (85% soln in toluene, 2.62 ml, 13.41 mmol of hydride) is added and the reaction stirred at 0° C. for 4 hours. The mixture is quenched with methanol and concentrated under vacuo. The residue is dissolved in CH$_2$Cl$_2$, washed with 2 portions of water, dried over magnesium sulfate, filtered and evaporated to dryness. The crude is purified by normal phase MPLC (SiO$_2$, DCM to DCM/MeOH 3:1), giving 2-[4-(aminomethyl)phenyl]-2-methylpropanenitrile (900 mg, 5.17 mmol, 39%) as a colorless oil. $^1$H NMR (400 MHz, DMSO-D6) δ ppm 1.68 (s, 6H) 4.00-4.05 (m, 2H) 7.55 (q, J=8.59 Hz, 4H) 8.35 (broad s, 2H).

Scheme 19 Synthesis of 2-[4-(aminomethyl)-3-methylphenyl]-2-methylpropanenitrile

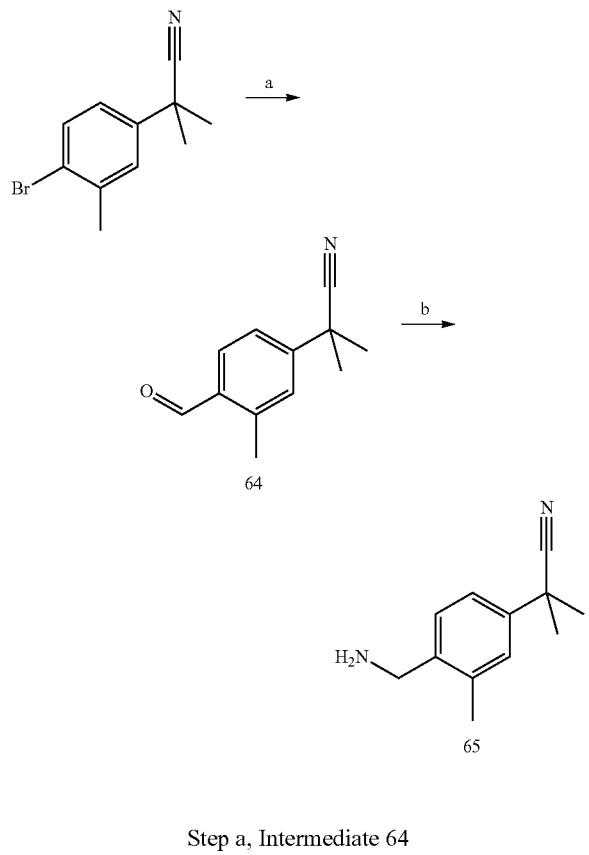

Step a, Intermediate 64

2-(4-formyl-3-methylphenyl)-2-methylpropanenitrile 2-(4-bromo-3-methylphenyl)-2-methylpropanenitrile (3.31 g, 13.9 mmol) is dissolved in dry THF (80 mL). The mixture is cooled to −78° C. and tert-BuLi (1.7 M in pentane, 18 mL, 30.6 mmol) is added. After 30 minutes, the reaction is quenched with DMF (10 mL), volatiles are evaporated and the residue purified by normal phase MPLC (SiO$_2$, heptane to heptane/EtOAc 3:1), giving 2-(4-formyl-3-methylphenyl)-2-methylpropanenitrile (1.89 g, 10.2 mmol, 73%) as a colorless liquid. $^1$H NMR (400 MHz, DMSO-D6) δ ppm 1.70 (s, 6H) 2.64 (s, 3H) 7.49 (s, 1H) 7.55 (dd, J=8.01, 2.15 Hz, 1H) 7.86 (d, J=7.81 Hz, 1H) 10.22 (s, 1H).

Step b, Intermediate 65

2-[4-(aminomethyl)-3-methylphenyl]-2-methylpropanenitrile 2-(4-formyl-3-methylphenyl)-2-methylpropanenitrile 1.89 g, 10.2 mmol) is dissolved in 50 ml of 7M NH$_3$ in MeOH. Ti(OiPr)$_4$ (6 mmol, 20 mmol) is added and the mixture stirred for 3 hours at room temperature. NaBH$_4$ (0.6 g, 15 mmol) is added and the reaction left at room temperature overnight. The mixture is quenched by the addition of 25 ml of NH$_4$OH 2 M. The resulting precipitate is filtered off and washed with EtOAc. Phases are separated, the organic phase is dried over magnesium sulfate, filtered and evaporated to dryness, giving 2-[4-(aminomethyl)-3-methylphenyl]-2-methylpropanenitrile (1.325 g, 7.09 mmol, 87%). The crude product is used without further purification. $^1$H NMR (400 MHz, DMSO-D6) δ 1.64 (s, 6H, first rotamer) 1.65 (s, 6H, second rotamer) 2.28 (s, 3H, first rotamer) 2.29 (s, 3H, second rotamer) 3.32 (broad s, 2 H) 3.67 (s, 2H, first rotamer) 3.68 (s, 2H, second rotamer) 7.24-7.27 (m, 1H) 7.28 (s, 1H) 7.36-7.40 (m, 1H).

Scheme 20
Separation of (S)-(−)-2-[4-(aminomethyl)-3-methylphenyl]-2-methylpropanenitrile from (R)-(+)-2-[4-(aminomethyl)-3-methylphenyl]-2-methylpropanenitrile

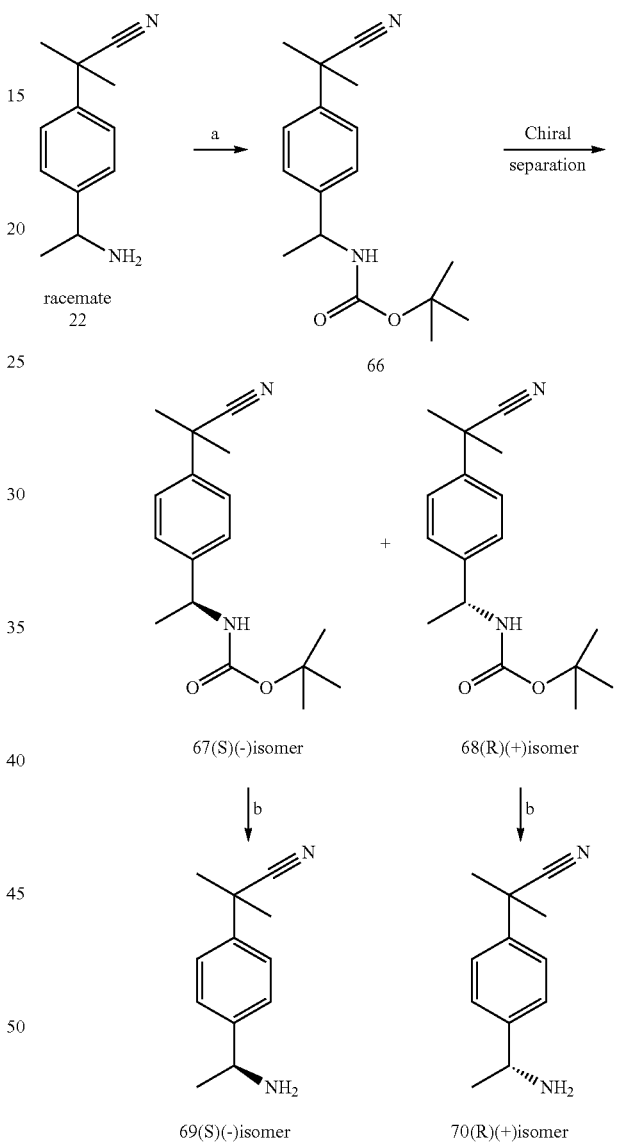

Step a, Intermediate 66, 67 and 68 tert-butyl N-[1-[4-(2-cyanopropan-2-yl)phenyl]ethyl]carbamate

To a stirred solution of racemic 2-[4-(1-aminoethyl)phenyl]-2-methylpropanenitrile hydrochloride (1 g, 3.97 mmol) in THF (12 mL) is added Et$_3$N (2.22 mL, 15.9 mmol). Di-tert-butyl dicarbonate (0.87 g, 3.97 mmol) in THF (2 mL) is added drop wise and the reaction mixture is stirred at room temperature 18 h. The resulting mixture is filtered on a silica gel pad and rinsed with a 1:1 solution of EtOAc and hexane. The filtrate is concentrated under reduced pressure and the crude product is left standing until it solidified. The latter is purified by recrystallization in 30 mL of hexane to provide the desired compound tert-butyl N-[1-[4-(2-cyanopropan-2-yl)phenyl] ethyl]carbamate (0.87 g, 68%) as a white solid. $^1$H NMR (300 MHz, CHLOROFORM-D): δ 7.44-7.41 (2H, m), 7.33-7.30 (2H, m), 4.80 (2H, s), 1.71 (6H, s), 1.44 (3H, s) 1.42 (9H, s).

The two enantiomers 67 and 68 are separated on a CHIRALPAK® AY® chiral column using a 9:1 Hexane:IPA mixture of eluent at 25° C. with UV detector set at 220 nm. The two enantiomers had optical rotation measurements values $[\alpha]_D=-76.2°$ (1.36, MeOH) for isomer 67 and of $[\alpha]_D=+78.7°$ (c=1.20, MeOH) for isomer 68.

Step b, Intermediate 69 (the Same Procedure is Carried Out to Obtain 70 from 68)

S(−)2-[4-(1-aminoethyl)phenyl]-2-methyl-propanenitrile

Hydrogen chloride (34.7 mL, 138.70 mmol) 4M in dioxane is added to a solution of (−)tert-butyl N-[1-[4-(2-cyanopropan-2-yl)phenyl]ethyl]carbamate 67 (8.00 g, 27.74 mmol) in tetrahydrofuran (45 mL) at ambient temperature. The reaction mixture is stirred for 2 hours and the solvent is concentrated to dryness. The residue is suspended in EtOAc (45 mL) and stirred for 1 hour. The solid is collected and air dried to provide the HCl salt of (S)-2-(4-(1-aminoethyl)phenyl)-2-methylpropanenitrile (6.08 g, 97%) as white solid. The material is suspended in MTBE (80 mL) and NaOH 2M (40 mL) is added. The mixture is stirred gently for 1 hour and the organic phase is separated. The aqueous phase is extracted with MTBE (40 mL). The combined organic layers are dried over anhydrous MgSO$_4$ and the solvent is concentrated to provide the expected product S(−)-2-[4-(1-aminoethyl)phenyl]-2-methyl-propanenitrile (4.88 g, 93%) as colorless oil.

1H NMR (400 MHz, CHLOROFORM-D) δ ppm 1.39 (d, J=6.64 Hz, 3H) 1.53-1.63 (m, 2H) 1.68-1.76 (m, 6H) 4.14 (q, J=6.64 Hz, 1H) 7.34-7.40 (m, 2H) 7.41-7.46 (m, 2H) MS (ESI) (M+H)$^+$ 188.9. $[\alpha]_D=-21.0°$ (1.44, EtOH)

For the other isomer 70 obtained by procedure as described above $[\alpha]_D=+19.0°$ (c=0.39, EtOH) Confirmation of the absolute configuration of intermediate 69 and 70 using Vibrational Circular Dichorism (VCD).
Short Description:

This technique involves calculation of the VCD spectra of the pure enantiomers for which the absolute configuration needs to be determined. These calculated spectra are then compared to the experimental VCD spectra obtained from the chiral substances. Matching specific spectral characteristics constitutes a confirmation of the absolute configuration of the enantiomers.
Computational Spectral Simulations:

A Monte Carlo molecular mechanics search of low energy conformers for 69 was conducted using MacroModel within the Maestro graphical interface (Schrödinger Inc.). The 12 lowest energy conformers identified are used as starting points and minimized using density functional theory (DFT) within Gaussian03.

Optimized structures, harmonic vibrational frequencies/intensities, VCD rotational strengths, and free energies at STP (including zero-point energies) were determined for each of the conformers. In these calculations, the B3LYP generalized gradient approximation (GGA) exchange-correlation density functional was used. Specifically, the GGA is the combination of Becke's exchange functional (the 3-parameter HF/DFT hybrid exchange functional [B3]) {Becke, A. D. J. Chem. Phys. 93, 98, 5648} with the dynamical correlation functional of Lee, Yang, and Parr (LYP) {Lee, C.; Yang, W.; Parr, R. G. Phys. Rev. B 1988, 37, 785}. The 6-31G* basis set {Hariharan, P. C.; Pople, J. A. Theor. Chim. Acta, 1973, 28, 213} is used Infrared and VCD spectra for each conformer is generated from the Gaussian 03 output files using one of a variety of software programs to fit Lorentzian line shapes (5 cm$^{-1}$ line width) to the computed spectra. In this manner, direct comparisons between simulated and experimental spectra can be made.
Experimental:

30 mgs of 69 and 70, respectively, were dissolved in 0.28 ml d$_6$-dmso. Solutions were individually loaded into a 0.1 mm BaF$_2$ infrared cell for analysis 4 cm$^{-1}$ resolution using a 5-hour, dual source, VCD scan protocol. All analyses were conducted using the BioTools, Inc. ChiralIR™ instrument. The instrument incorporated a single photo-elastic modulator set for polarization modulation at 37.024 kHz with λ/4 retardation (optimized for acquisition of the spectral region centered around 1400 cm$^{-1}$). Lock-in amplification with a 30 μs time constant, and a 20 kHz high pass and a 4 kHz low pass filter was used.
Results:

Comparison of the vibrational circular dichroism (VCD) infrared spectra to predicted VCD spectra (obtained through molecular mechanics and density functional theory calculations) indicated the structure to be consistent with the proposed S configuration for intermediate 69 and R configuration for intermediate 70.

Scheme 21 Enantioselective synthesis of S(-)2-[4-(aminomethyl)-3-methylphenyl]-2-methylpropanenitrile

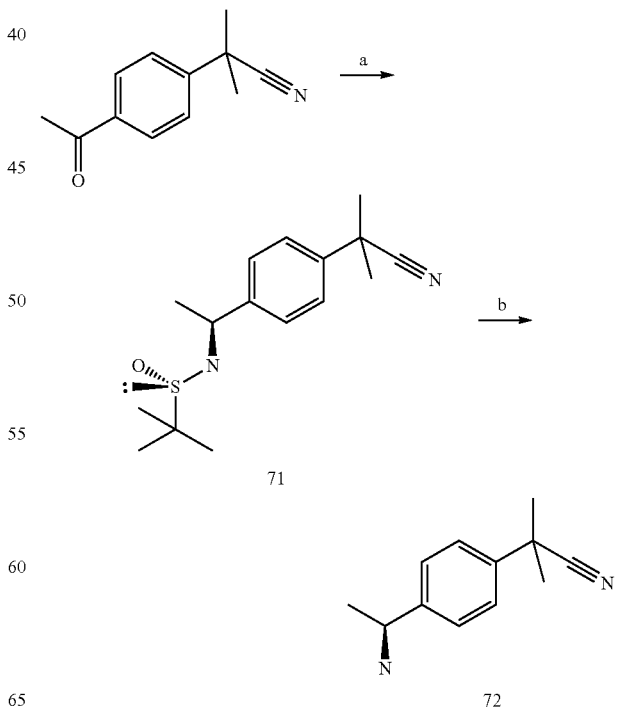

Step a, Intermediate 71

N-{(S,S)-1-[4-(1-cyano-1-methylethyl)phenyl]ethyl}-2-methylpropane-2-sulfinamide To a 500 ml, 3-necked rbf equipped with a thermometer, nitrogen inlet, a rubber septum and a magnetic stirring-bar is charged 8.13 g (36.93 mmol, assumed to contain 85% by weight of the ketone only) of the arylmethyl ketone and (S)-(−)-t-butylsulfinamide (4.47 g, 1 eq). The set-up is flushed with nitrogen. Anhydrous THF (82 mL, 10 parts wt the crude weight) is added and the resulting solution is stirred moderately under nitrogen. To this solution is added Ti(OEt)$_4$ (15.32 mL, 2 eqs) via a syringe. The resultant deep yellow solution is heated under nitrogen to a gentle reflux with moderate agitation and kept for ~24 hours (minor foaming of the reaction mixture is observed). Analysis by $^1$H NMR shows that reaction is completed.

The reaction mixture is first cooled to ambient temperature and then to 0-5° C. by immersing in an ice-water bath. To this mixture is added sodium borohydride (2.1 g, 1.5 eqs) (caution: moderate foaming and an exotherm from 3 to 10° C. are observed). The resulting reaction mixture is stirred at 0-5° C. for another 5 hours and then is allowed to warm to ambient temperature and stirred overnight (~14 hours). A sample is withdrawn for IPC by $^1$H NMR and shows all ketimine are consumed.

The mixture is cooled to 0-5° C. Acetone (16.3 mL, ~6 eqs) is added gradually over 15-20 minutes to consume the remaining hydride (caution: an exotherm from ~3 to 15° C. is observed). After the addition is completed, the reaction mixture is stirred for 15 minutes. MeOH (2 mL) is charged to test for the presence of residual hydride—no hydrogen evolution is observed. The mixture is allowed to warm to ambient temperature and transferred to a 500 mL Erlenmeyer flask. The rbf is rinsed forward with 160 mL of MTBE. The resulting mixture is stirred vigorously for 5 minutes. Brine (10 mL) is charged portionwise over a period of 2-3 minutes to induce precipitation of the titanium reagent. The suspension formed is stirred vigorously for 30 minutes and then is filtered through a thick pad of sand. The sand pad is washed with 3×30 mL of MTBE. The combined filtrate is stirred with 150 mL of brine for another 1 hour to produce a murky biphasic mixture, which is transferred to a reparatory funnel. The lower aqueous layer is removed and the upper organic layer is filtered through a pad of celite. The filtrate is evaporated to dryness to give the expected product N-{(S,S)-1-[4-(1-cyano-1-methylethyl)phenyl]ethyl}-2-methylpropane-2-sulfinamide (11.1 g) as a yellow syrup. This material is assumed to be 100% pure and is used directly for the next step without further purification As reported by Ellman (Ellman & coworkers Tetrahedron, 40 (1999) 6709-6712) the crude product consists of a mixture of 2 diastereomers predominated by one. The ratio of these two isomers represents the degree of asymmetry induced by the chiral sulfinyl group. Typically, the ratio observed for this reduction ranged from 92:8 to 95:5, as shown by HPLC and $^1$H NMR analyses of the crude product mixture.

$^1$H NMR 400 MHz (CHLOROFORM-D) δ: 1.26 (s, 9H), 1.53 (d, 3H, J=8 Hz), 1.75 (s, 6H), 4.52-4.62 (m, 1H), 7.40 (d, 2H, J=8 Hz), 7.48 (d, 2H, J=8 Hz).

Step b, Intermediate 72

To a 250 mL rbf equipped with a magnetic stirring bar containing the substituted sulfinamide (11.1 g, 1 eq, assumed to be 100% pure) prepared in the above step is added dioxane (28.3 mL). The resulting solution is cooled to 0-5° C. in an ice-water bath while being stirred vigorously. To this solution is charged, via syringe, HCl in dioxane (28.3 mL, 3 eqs) in one portion. White solid started to precipitate from the solution immediately. The resultant suspension is stirred at 0-5° C. (bath temperature) for another 10 minutes to produce thick white slurry. The cooling bath is removed at this point. A small sample of the reaction mixture is withdrawn and analysed by tlc. All starting sulfinamide are consumed.

The mixture is diluted with EtOAc (28.3 mL) and stirred for another 5 minutes at ambient temperature. The white solid is then collected by suction filtration. The flask is rinsed forward with 2×10 mL of EtOAc. The filter cake is washed with another 2×10 mL of EtOAc and then is sucked dry under a stream of nitrogen. The filter cake is dried further at 40-45° C. in a vacuum oven overnight to give 4.28 g of a crystalline white solid. Analysis of this material by $^1$H NMR spectroscopy showed only the presence of the desired amine hydrochloride.

According to our observation, the optical purity of this chiral amine, as correlated directly to the ratio of the two substituted diastereomeric sulfinamide precursors, ranged from 84 to 90% e.e. These numbers assumed that the final HCl treatment step has no impact on the optical purity of the amine.

$^1$H NMR 400 MHz (CHLOROFORM-D) δ 1.20 (d, 3H, J=8 Hz), 1.70 (s, 3H), 1.71 (s, 3H), 3.73 (AB q, 1H, J=14, 6 Hz), 4.50 (br. s, 1H), 7.17 (d, 2H, J=8 Hz), 7.21-7.31 (m, 5H), 7.41 (d, 2H, J=8 Hz).

The amine HCl salt (3.12 g, 13.89 mmol, 1 eq) is dissolved in 26 mL of water in a 100 mL rbf with gentle magnetic stirring. Aqueous 2 M sodium hydroxide (7.6 mL, 1.1 eqs) is added to this solution to adjust its resultant pH to 13-14, leading to the formation of a light emulsion. MTBE (26 mL) is charged to this emulsion and the resultant mixture is stirred vigorously. The upper organic layer is collected and the aqueous layer is diluted with brine (15 mL) followed by extraction with another 26 mL of MTBE. The organic layers are combined, washed with brine (15 mL) and then is dried over anhydrous sodium sulphate. Removal of the drying agent by filtration and evaporation of the filtrate to dryness gave the amine as pale yellow light oil.

The oil obtained above is dissolved in acetone (26 mL) and stirred under nitrogen. A solution of (+)-Mandelic acid (2 g, 0.95 eqs wrt the amine HCl salt used) in acetone (15 mL) made up in a separate vessel is charged to the amine. The vessel is rinsed forward with more acetone (5 mL). Precipitation of a crystalline solid (the salt) occurred quickly to give a heavy white suspension. This suspension is stirred for 15 minutes and then is cooled to 0-5° C. and stirred for another 30 minutes. The white solid is collected by suction filtration and washed with acetone (2×10 mL). The cake is dried in a vacuum oven at 40-45° C. overnight (~16 hours) to furnish 3.67 g (77%) of the (+)-Mandelic acid salt as a crystalline white solid.

$^1$H NMR spectroscopy analysis of the product isolated above in deuterated chloroform indicated that only one enantiomer of the amine is present.

A 2 L rbf equipped with an overhead stirred is charged with the Mandelic acid salt (50.8 g, 149.3 mmol, 1 eq) and MTBE (1 L, 6.5 parts) to produce a suspension. To this suspension under moderate stirring is added a solution of NaOH (1 M, 672 mL, 672 mmol, 4.5 eqs). The resultant biphasic mixture is agitated vigorously at room temperature for a period of 30 minutes and then is transferred to a reparatory funnel. The layers are separated. The aqueous layer is diluted with 500 mL of brine and extracted with MTBE (2×250 mL). The combined organic phases are dried over MgSO$_4$. Removal of the drying agent followed by evaporating the filtrate to dryness gave the free amine as light yellow oil. (27.7 g, 99%)

$^1$H NMR 400 MHz (CHLOROFORM-D) δ 1.20 (d, 3H, J=8 Hz), 1.70 (s, 3H), 1.71 (s, 3H), 3.73 (AB quartet, 1H, J=14, 6 Hz), 4.50 (br. s, 1H), 7.17 (d, 2H, J=8 Hz), 7.21-7.31 (m, 5H), 7.41 (d, 2H, J=8 Hz).

Scheme 22 Enantioselective synthesis of (-)1-[4-[1-aminoethyl]phenyl]cyclobutane-1-carbonitrile

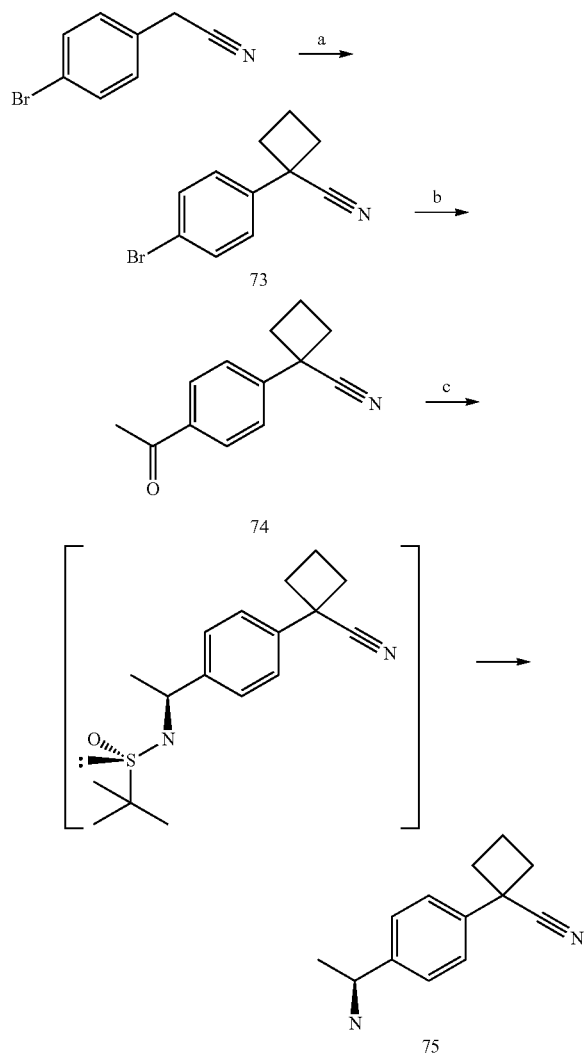

Step a, Intermediate 73

1-(4-bromophenyl)cyclobutanecarbonitrile

To a stirred suspension of sodium hydride (60% susp. in oil, 12.24 g, 255 mmol) in anhydrous DMSO (240 mL) is added dropwise 2-(4-bromophenyl)acetonitrile (20.0 g, 102 mmol) dissolved in anhydrous DMSO (40 mL). After 45 min, the reaction mixture is cooled to 0° C. and 1,3-dibromopropane (30.9 g, 15.5 mL, 153 mmol) dissolved in anhydrous DMSO (40 mL) is added slowly to maintain the temperature below 45° C. The reaction mixture is stirred overnight at room temperature and poured in cold water (1.2 L). The product is extracted with CH$_2$Cl$_2$ (6×100 mL), dried on MgSO$_4$, filtered and concentrated under reduced pressure. The product is purified by flash chromatography eluting with hexane:EtOAc (100% to 95:5) to provide the expected product 1-(4-bromophenyl)cyclobutanecarbonitrile (9.9 g, 41%) as a yellowish oil. 1H NMR (300 MHz, CHLOROFORM-D): δ 7.57-7.49 (2H, m), 7.33-7.24 (2H, m), 2.89-2.77 (2H, m), 2.66-2.34 (3H, m), 2.15-1.99 (1H, m).

Step b, Intermediate 74

1-(4-acetylphenyl)cyclobutanecarbonitrile

To a stirred solution of 1-(4-bromophenyl)cyclobutanecarbonitrile (2.8 g, 11.9 mmol) in anhydrous THF (70 mL) at −78° C. is added n-butyllithium (2 M in c-hexane) (7.44 mL, 14.9 mmol). The reaction mixture is stirred at that temperature 10 min., then N-methoxy-N-methyl-acetamide (2.50 mL, 23.8 mmol) is added and the solution is then left to warm-up to room temperature over 1 h. A mixture of brine (30 mL) and 1 N HCl (15 mL) is then slowly added and the solution is extracted with EtOAc (3×100 mL). The organic layer is dried over MgSO$_4$, filtered and concentrated under reduced pressure. The crude product is purified by flash chromatography using a 0 to 20% EtOAc in hexane gradient to yield 1-(4-acetylphenyl)cyclobutanecarbonitrile (1.35 g, 57%) as a yellowish oil. 1H NMR (300 MHz, CHLOROFORM-D) δ 8.03-(2H, m), 7.56-7.50 (2H, m), 2.94-2.81 (2H, m), 2.71-2.57 (2H, m), 2.62 (3H, s), 2.57-2.40 (1H, m), 2.18-2.05 (1H, m).

Step c, Intermediate 75

(−)-1-[4-[1-aminoethyl]phenyl]cyclobutane-1-carbonitrile

To 1-(4-acetylphenyl)cyclobutanecarbonitrile (8.6 g, 43.2 mmol) and anhydrous THF (85 mL) with (S)-(−)-tert-butylsulfinamide (5.7 g, 1.1 eqs) is added titanium tetraethoxide (18 mL, 2 eqs). The resultant mixture is heated to reflux under nitrogen and kept at reflux for 18 hours. An aliquot is withdrawn and analyzed for completion of reaction.

The mixture is cooled to room temperature and then to 0-5° C. Sodium borohydride (2.4 g, 1.5 equivalents) is added to the reaction mixture in small portions over a period of 10 minutes. The resulting mixture is allowed to warm to RT over 1 hour and stirring at room temperature is continued for another 3 hours.

The reaction is quenched with the addition of acetone (19 mL, 6 eqs) and the resultant mixture is diluted with brine (25 mL). With moderate agitation, MTBE (80 mL) is added and agitation is continued for ~15 minutes. The bi-layer mixture obtained is filtered through a sintered funnel packed with Celite. The organic layer is collected and is dried over anhydrous magnesium sulphate. Evaporated this organic solution to dryness under reduced pressure gives the desired substituted chiral sulfinamide as a viscous syrup (13.3 g). This crude material is used without further purification.

The crude chiral sufinamide (13.3 g) obtained above is dissolved in dioxane (130 mL) with moderate stirring in a rbf. To the resulting mixture is charged 4 M HCl in dioxane (32.8 mL, 3 eqs) and stirring is continued at room temperature overnight (~16 hours). The reaction mixture is evaporated to dryness on a rotary evaporator and the residue obtained is triturated with EtOAc (100 ml) for 1 hour. The white solid is filtered and washed. Drying of the filter cake in a vacuum oven overnight provides the expected chiral amine (−)-1-[4-[1-aminoethyl]phenyl]cyclobutane-1-carbonitrile (5.0 g) in its hydrochloride form as a white solid.

¹H NMR data (400 MHz, DMSO-d₆) δ 1.52 (3H, d, J=8 Hz), 1.94-2.07 (1H, m), 2.20-2.35 (1H, m), 2.55-2.67 (2H, m), 2.70-2.80 (2H, m), 4.44 (1H, q, J=6.8 Hz), 7.52 (2H, J=8.4 Hz), 7.61 (2H, d, J=8.4 Hz), 8.40-8.90 (3H, m).

Prior to coupling reaction to obtain the final chiral examples, the free base of intermediate 75 is generated using the procedure outlined in step b described in the preparation of intermediate 72.

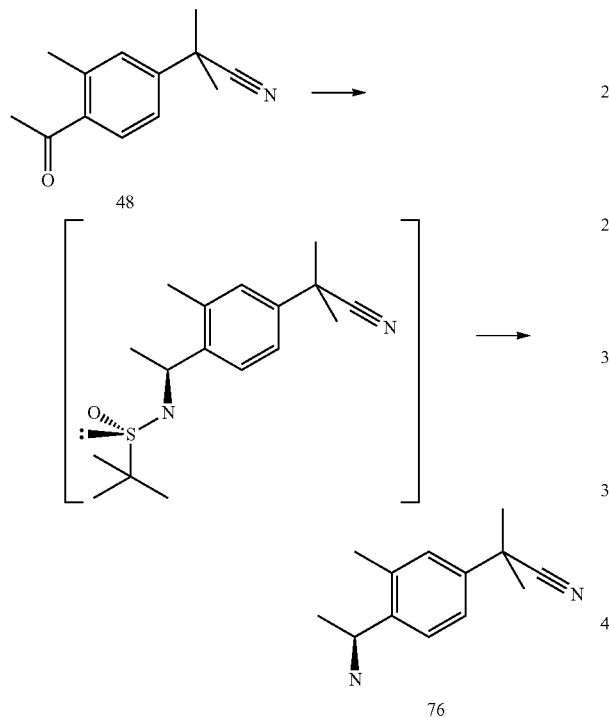

Scheme 23 Enantioselective synthesis of (-)2-[4-[1-aminoethyl]-3-methyl-phenyl]-2-methyl-propanenitrile To 2-(4-acetyl-3-methyl-phenyl)-2-methyl-propanenitrile (1.47 g, estimated 80% assay=>5.8 mmol) and anhydrous THF (12 mL, 10 parts) with (S)-(−)-tert-butylsulfinamide (0.7 g, 1 eqs) is added titanium tetraethoxide (2.4 mL, 2 eqs). The resultant mixture is heated to reflux under nitrogen and kept for 22 hours (overnight) followed by agitation at room temperature over the weekend. Analysis of the reaction mixture indicates that the reaction is completed.

With moderate agitation, the reaction mixture is cooled to 0-5° C. (ice-water bath). Sodium borohydride (0.35 g, 1.5 equivalents) is added to the reaction mixture in small portions over a period of 10 minutes. The resulting mixture is stirred for 3 hours at 0-5° C. and then is allowed to warm to room temperature slowly. Stirring at room temperature is continued for another 1 hour.

After cooling the mixture to 0-5° C., the reaction is quenched by the addition of acetone (2 mL, 6 eqs) and the resultant mixture is diluted with brine (4 mL). With moderate agitation, MTBE (20 mL) is added and agitation is continued for 10 minutes. This aqueous-organic mixture is filtered through a pad of Celite. The organic phase is collected and dried over anhydrous magnesium sulfate. Evaporation of this organic solution to dryness under reduced pressure gave the desired substituted chiral sulfinamide as a yellow viscous syrup (1.88 g). The ¹H NMR spectrum of this material shows the presence of the desired substituted sulfinamide as the major product together with other impurities. This crude material obtained is assumed to be 100% pure and is used without further purification.

The crude chiral sufinamide (0.28 g, 0.4 mmol) obtained above is dissolved in dioxane (3 mL) with moderate stirring in a rbf. To the solution formed is charged 4 M HCl in dioxane (0.7 mL, 3 eqs) and the resultant mixture is stirred at room temperature for 30 minutes to generate a heavy white suspension. This suspension is evaporated to dryness on a rotary evaporator and the residue obtained is triturated with EtOAc (10 mL) for 10 minutes. The white solid is collected by filtration and washed with more EtOAc. Air drying of the filter cake at room temperature gives the desired chiral amine hydrochloride (−)2-[4-[1-aminoethyl]-3-methyl-phenyl]-2-methyl-propanenitrile as a white power (95 mg).

¹H NMR (400 MHz, DMSO-d₆) δ 1.48 (3H, d, J=8 Hz), 1.68 (6H, s), 2.39 (3H, s), 4.53 (1H, ABq, J=16, 8 Hz), 7.39 (1H, d, J=2 Hz), 7.44 (1H, d of d, J=8, 2 Hz), 7.64 (1H, d, J=8 Hz), 6.8-9 (unresolved m, exchanged with D₂O).

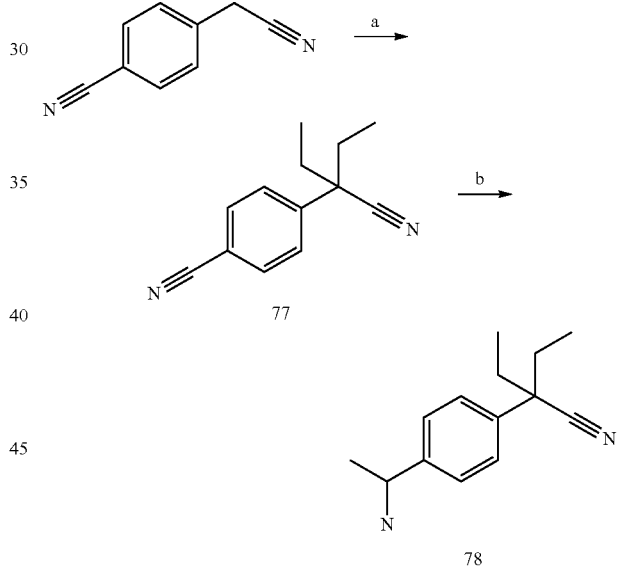

Scheme 24 synthesis of 2-[4-(1-Aminoethyl)phenyl]-2-ethylbutanenitrile

Step a Intermediate 77

4-(1-Cyano-1-ethylpropyl)benzonitrile

4-Cyanomethylbenzonitrile (1.02 g, 7.18 mmol) and ethyl iodide (2.25 g, 14.4 mmol) are added to DMF (20.0 mL), and the resulting solution is cooled to 0° C. NaH (576 mg, 14.4 mmol) is added in portions. The mixture is warmed to room temperature and then stirred for 3 hours. Water (100 mL) is added, and the aqueous phase is extracted with EtOAc (4 times with 50.0 mL). The combined organic phases are dried with MgSO₄, filtered and concentrated on the rotovaporator. The product is purified by Combi-Flash silica gel chromatography, eluting with mixtures of heptane and EtOAc (100/0 to 70/30), (936 mg, 5.51 mmol, 77%). ¹H NMR (400 MHz, DMSO-D6) δ ppm 0.77 (t, J=7.42 Hz, 6H) 1.89-2.14 (m, 4H) 7.64 (d, J=8.40 Hz, 2H) 7.92 (d, J=8.59 Hz, 2H).

Step b Intermediate 78

2-[4-(1-Aminoethyl)phenyl]-2-ethylbutanenitrile 4-(1-Cyano-1-ethylpropyl)benzonitrile (936 mg, 5.51 mmol) is added to THF (20.0 mL), and the resulting solution is cooled to −78° C. MeLi (3.44 mL, 5.51 mmol) is added, and the solution is stirred for 20 minutes. NaBH$_4$ (208 mg, 5.51 mmol) is mixed in MeOH (20.0 mL) and added to the first solution. The resulting solution is warmed to room temperature and stirred for 1 hour. 1N HCl (50.0 mL) is added followed by 1N NaOH (60.0 mL). The aqueous phase is extracted with EtOAc (4 times 50.0 mL) and the combined organic phases are dried with MgSO$_4$, filtered and concentrated on the rotovaporator. The product is purified by HPLC: Gilson prep pumps, Flow rate: 30 ml/min, Column: Gemini (5u) 21.2×50 mm, Mobile phase: A=water (10 mM NH$_4$CO$_3$) B=MeCN, (528 mg, 2.44 mmol, 44%). $^1$H NMR (400 MHz, DMSO-D6) δ ppm 0.77 (t, J=7.32 Hz, 6H) 1.22 (d, J=6.45 Hz, 3H) 1.82-2.07 (m, 4H) 3.97 (q, J=6.64 Hz, 1H) 7.32 (d, J=8.40 Hz, 2H) 7.40 (d, J=8.20 Hz, 2H).

Example 1

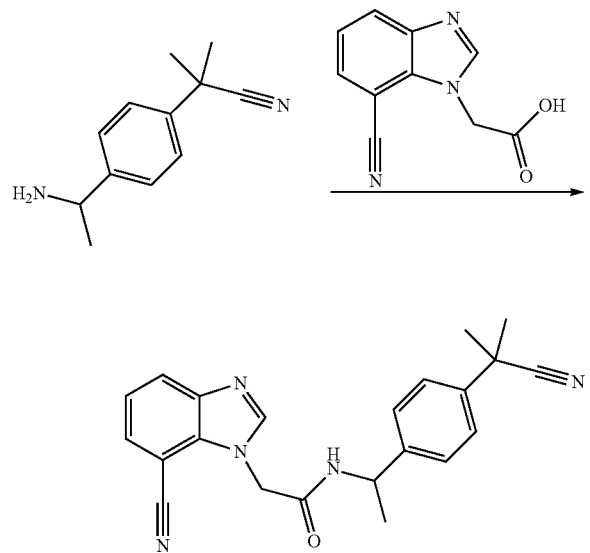

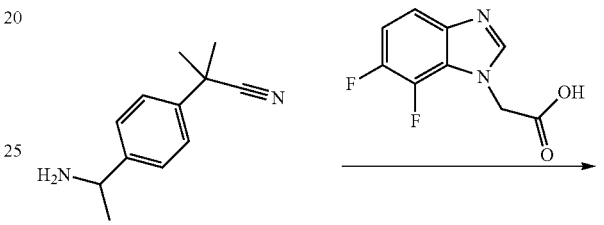

(R)(+) and (S)(−)-2-(7-Cyano-1H-benzimidazol-1-yl)-N-{1-[4-(1-cyano-1-methylethyl)phenyl]ethyl}acetamide 2-[4-(1-Aminoethyl)phenyl]-2-methylpropanenitrile hydrochloride prepared according to scheme (557 mg, 2.49 mmol), (7-cyano-1H-benzimidazol-1-yl)acetic acid (500 mg, 2.49 mmol) prepared according to scheme 3 and DMAP (601 mg, 4.97 mmol) are mixed in DMF (10.0 mL). HATU (945 mg, 2.49 mmol) is added, and the mixture is stirred for 18 hours. The reaction mixture is filtered and then purified on HPLCMS: Waters prep LCMS, Flow rate: 27 ml/min, Column: SynerSi (4μ) Polar RP, 21.2×50 mm, Mobile phase: A=water (0.05% TFA) B=MeCN, Gradient used 40% to 70% B in A, in 10 min. The fractions are combined, NaOH 1N is added and the desired compound is extracted with ethyl acetate. The combined organic fractions are concentrated under reduced pressure to yield the product (610 mg, 1.64 mmol, 66%). $^1$H NMR (400 MHz, METHANOL-D4) δ ppm 1.50 (d, J=7.03 Hz, 3H) 1.68 (s, 6H) 4.98-5.09 (m, 1H) 5.33 (s, 2H) 7.37-7.43 (m, 3H) 7.46 (d, J=8.20 Hz, 2H) 7.68 (d, J=7.62 Hz, 1H) 7.97 (dd, J=8.20, 0.98 Hz, 1H) 8.28 (s, 1H) 8.89 (d, J=7.62 Hz, 1H), MS [M+H], calcd: 372.2. found: 372.3.

The enantiomers are separated by chiral HPLC: Gilson, Inc. prep pumps, Flow rate: 18 ml/min, Column®: Chiralcel OD 21×250 mm (5μ), Mobile phase: A=Hexane (0.1% DEA) B=EtOH (0.1% DEA), 80% A:20% B isocratic [α]$_D$=−156 (c=8.2, MeOH) and [α]$_D$=+136 (c=13.4, MeOH).

Example 2

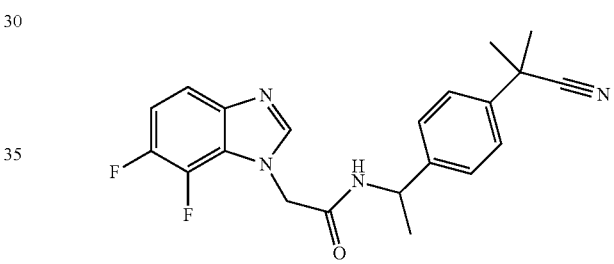

(R)(+) and (S)(−)-N-{1-[4-(1-Cyano-1-methylethyl)phenyl]ethyl}-2-(6,7-difluoro-1H-benzimidazol-1-yl)acetamide N-{1-[4-(1-Cyano-1-methylethyl)phenyl]ethyl}-2-(6,7-difluoro-1H-benzimidazol-1-yl)acetamide is synthesized according to example 1 by mixing (6,7-difluoro-1H-benzimidazol-1-yl)acetic acid (500 mg, 2.36 mmol) prepared according to scheme 2, 2-[4-(1-aminoethyl)phenyl]-2-methylpropanenitrile hydrochloride (525 mg, 2.36 mmol) prepared according to scheme 6, DMAP (570 mg, 4.71 mmol) and HATU (896 mg, 2.36 mmol) in DMF (10.0 mL). The product is purified on HPLCMS: Waters prep LCMS, 27 ml/min, Column: SynerSi (4μ) Polar RP, 21.2×50 mm, Mobile phase: A=water (0.05% TFA) B=MeCN, Gradient used 40% to 60% B in A, in 10 min. The fractions are combined, NaOH 1 N is added and the desired compound is extracted with ethyl acetate. The combined organic fractions are concentrated under reduced pressure to yield the product (450 mg, 2.36 mmol, 50%). $^1$H NMR (400 MHz, METHANOL-D4) δ ppm 1.49 (d, J=7.03 Hz, 3H) 1.68 (s, 6H) 5.03 (m, 1H) 5.20 (m, 2H) 7.30 (dt, J=11.23, 8.98, 7.32 Hz, 1H) 7.35-7.42 (m, 2H) 7.44-7.54 (m, 3H) 8.56 (s, 1H) MS [M+H], calcd: 383.2. found: 383.3.

HRMS (ESI+) calcd for C21H21F2N4O 383.16779 [M+H]+ found 383.16782.

The enantiomers are separated by chiral HPLC: Gilson, Inc. prep pumps, Flow rate: 18 ml/min, Column: Chiralcel OD 21×250 mm (5μ), Mobile phase: A=Hexane (0.1% DEA) B=i-PrOH (0.1% DEA), isocratic 80% A, 30% B. $[\alpha]_D$=−160 (c=5.4, MeOH) and $[\alpha]_D$=+164 (c=6.0, MeOH).

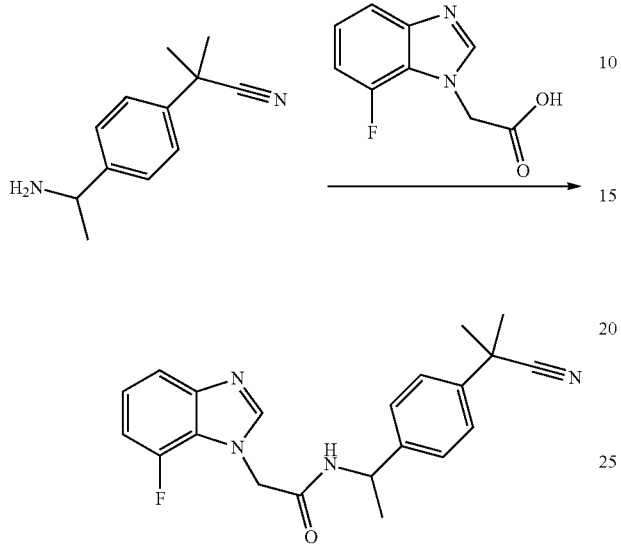

Example 3

(R)(+) and (S)(−)-N-{1-[4-(1-Cyano-1-methylethyl)phenyl]ethyl}-2-(7-fluoro-1H-benzimidazol-1-yl)acetamide N-{1-[4-(1-Cyano-1-methylethyl)phenyl]ethyl}-2-(7-fluoro-1H-benzimidazol-1-yl)acetamide is synthesized according to example 1 by mixing (7-fluoro-1H-benzimidazol-1-yl)acetic acid (200 mg, 1.03 mmol) prepared according to scheme 5, 2-[4-(1-aminoethyl)phenyl]-2-methylpropanenitrile hydrochloride (231 mg, 1.03 mmol) prepared according to scheme 6, DMAP (249 mg, 2.06 mmol) and HATU (391 mg, 1.03 mmol) in DMF (4.0 mL). The product is purified on HPLCMS: Waters prep LCMS, 27 ml/min, Column: SynerSi (4μ) Polar RP, 21.2×50 mm, Mobile phase: A=water (0.05% TFA) B=MeCN, Gradient used 30% to 50% B in A, in 10 min. The fractions are combined, NaOH 1 N is added and the desired compound is extracted with ethyl acetate. The combined organic fractions are concentrated under reduced pressure to yield the product (226 mg, 0.621 mmol, 60%). $^1$H NMR (400 MHz, METHANOL-D4) δ ppm 1.48 (d, J=7.03 Hz, 3H) 1.69 (s, 6H) 5.03 (q, J=6.90 Hz, 4H) 5.09 (d, J=16.99 Hz, 1H) 5.14 (d, J=16.99 Hz, 1H) 7.00 (dd, J=11.43, 8.11 Hz, 1H) 7.20 (td, J=8.11, 4.88 Hz, 1H) 7.37 (d, J=8.20 Hz, 2H) 7.43-7.50 (m, 3H) 8.10 (s, 1H); MS [M+H], calcd: 365.2. found: 365.3.

It is believed that the enantiomers could be separated by chiral HPLC: Gilson, Inc. prep pumps, Flow rate: 18 ml/min, Column: Chiralcel OD 21×250 mm (5μ), Mobile phase: A=Hexane (0.1% DEA) B=EtOH (0.1% DEA), 80% A:20% B isocratic

Example 4

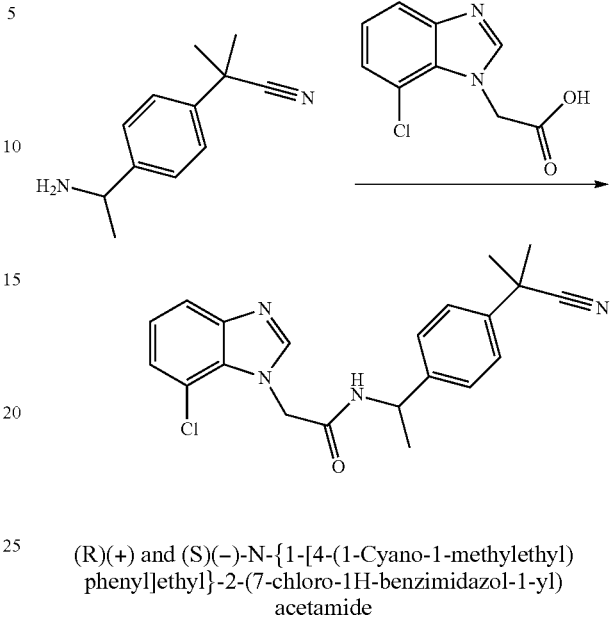

(R)(+) and (S)(−)-N-{1-[4-(1-Cyano-1-methylethyl)phenyl]ethyl}-2-(7-chloro-1H-benzimidazol-1-yl)acetamide N-{1-[4-(1-Cyano-1-methylethyl)phenyl]ethyl}-2-(7-chloro-1H-benzimidazol-1-yl)acetamide is synthesized according to example 1 by mixing (7-chloro-1H-benzimidazol-1-yl)acetic acid (100 mg, 0.48 mmol) prepared according to scheme 1, 2-[4-(1-aminoethyl)phenyl]-2-methylpropanenitrile hydrochloride (107 mg, 0.48 mmol) prepared according to scheme 6, DMAP (115 mg, 0.95 mmol) and HATU (181 mg, 0.48 mmol) in DMF (2.0 mL). The product is purified on HPLCMS: Waters prep LCMS, 27 ml/min, Column: SynerSi (4μ) Polar RP, 21.2×50 mm, Mobile phase: A=water (0.05% TFA) B=MeCN, Gradient used 40% to 70% B in A, in 10 min. The fractions are combined and freeze dried to give the desired product as the TFA salt (50 mg, 0.100 mmol, 21%). $^1$H NMR (400 MHz, METHANOL-D4) δ ppm 1.48 (d, J=7.03 Hz, 3H) 1.69 (s, 6H) 5.03 (q, J=6.71 Hz, 1H) 5.21-5.34 (m, 2H) 7.16-7.28 (m, 2H) 7.38 (d, 2H) 7.46 (d, 2H) 7.59 (dd, J=7.52, 1.27 Hz, 1H) 8.13 (s, 1H); MS [M+H], calcd: 381.1. found: 381.3.

It is believed that the enantiomers could be separated by chiral HPLC: Gilson, Inc. prep pumps, Flow rate: 18 ml/min, Column: Chiralcel OD 21×250 mm (5μ), Mobile phase: A=Hexane (0.1% DEA) B=EtOH (0.1% DEA), 80% A:20% B isocratic.

Example 5

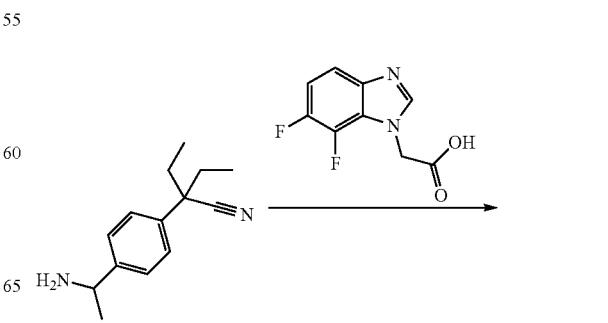

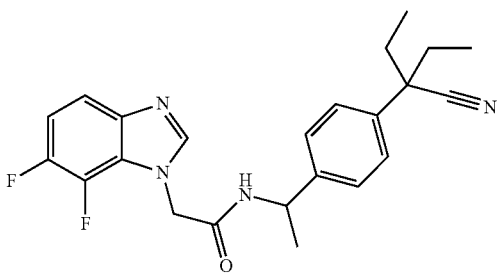

(+) and (−)-N-{1-[4-(1-Cyano-1-ethylpropyl)phenyl]ethyl}-2-(6,7-difluoro-1H-benzimidazol-1-yl)acetamide 2-[4-(1-Aminoethyl)phenyl]-2-ethylbutanenitrile (520 mg, 2.41 mmol) prepared according to scheme 24, (6,7-difluoro-1H-benzimidazol-1-yl)acetic acid (510 mg, 2.41 mmol) prepared according to scheme 2 and Et₃N (731 mg, 7.22 mmol, 1.00 mL) are mixed in MeCN (15.0 mL). HATU (915 mg, 2.41 mmol) is added and the mixture is stirred for 2 hours. 1N NaOH (40.0 mL) is added, and the aqueous phase is extracted with EtOAc (4 times 40.0 mL). The combined organic phases are dried with MgSO₄, filtered and concentrated on the rotovaporator. The product is purified by HPLC: Gilson prep pumps, Flow rate: 30 ml/min, Column: Gemini (50 21.2×50 mm, Mobile phase: A=water (10 mM NH₄CO₃) B=MeCN, (804 mg, 1.96 mmol, 81%). ¹H NMR (400 MHz, DMSO-D6) δ ppm 0.77 (t, J=7.32 Hz, 6H) 1.40 (d, J=7.03 Hz, 3H) 1.83-2.13 (m, 4H) 4.96 (ddd, J=14.65, 7.23, 7.03 Hz, 1H) 5.08 (s, 2H) 7.21 (ddd, J=11.57, 8.93, 7.62 Hz, 1H) 7.35-7.41 (m, 4H) 7.45 (ddd, J=8.84, 3.86, 0.78 Hz, 1H) 8.19-8.22 (m, 1 H) 8.83 (d, J=8.01 Hz, 1H); MS [M+H], calcd: 411.0. found: 411.3.

The enantiomers are separated by chiral HPLC: Gilson prep pumps, Flow rate: 18 ml/min, Column: Chiralcel AD 21×250 mm (20μ), Mobile phase: A=Hexane (0.1% DEA) B=i-PrOH (0.1% DEA), α_D=−149 (c=3.2, MeOH) and α_D=+178 (c=3.4, MeOH).

Example 6

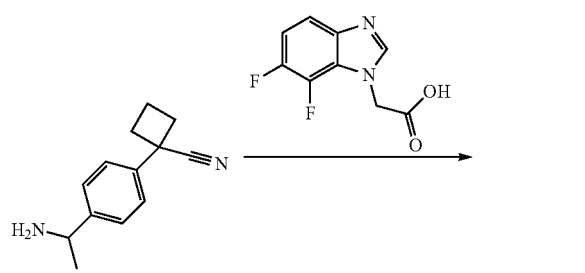

(+) and (−)-N-{1-[4-(1-Cyanocyclobutyl)phenyl]ethyl}-2-(6,7-difluoro-1H-benzimidazol-1-yl)acetamide N-{1-[4-(1-Cyanocyclobutyl)phenyl]ethyl}-2-(6,7-difluoro-1H-benzimidazol-1-yl)acetamide is synthesized according to example 5 by mixing (6,7-difluoro-1H-benzimidazol-1-yl)acetic acid (212 mg, 1.00 mmol) prepared according to scheme 2, 1-[4-(1-aminoethyl)phenyl]cyclobutanecarbonitrile (200 mg, 1.00 mmol) prepared according to scheme 9, Et₃N (304 mg, 3.00 mmol, 0.418 mL) and HATU (280 mg, 1.00 mmol) in MeCN (10.0 mL). The product is purified by HPLC: Gilson prep pumps, Flow rate: 30 ml/min, Column: Gemini (5μ) 21.2×50 mm, Mobile phase: A=water (10 mM NH₄CO₃) B=MeCN, (220 mg, 0.558 mmol, 56%). ¹H NMR (400 MHz, DMSO-D6) δ ppm 1.39 (d, J=7.03 Hz, 3H) 1.91-2.05 (m, 1 H) 2.16-2.34 (m, 1H) 2.53-2.64 (m, 2H) 2.66-2.78 (m, 2H) 4.87-5.01 (m, 1H) 5.07 (s, 2 H) 7.11-7.31 (m, 1H) 7.33-7.49 (m, 5H) 8.19 (s, 1H) 8.84 (d, J=7.81 Hz, 1H); MS [M+H], calcd: 395.0. found: 395.2.

The enantiomers are separated by chiral HPLC: Gilson prep pumps, Flow rate: 18 ml/min, Column: Chiralcel OD 21×250 mm (5μ), Mobile phase: A=Hexane (0.1% DEA) B=EtOH (0.1% DEA), α_D=−135 (c=0.57, MeOH) and α_D=+199 (c=4.1, MeOH).

Example 7

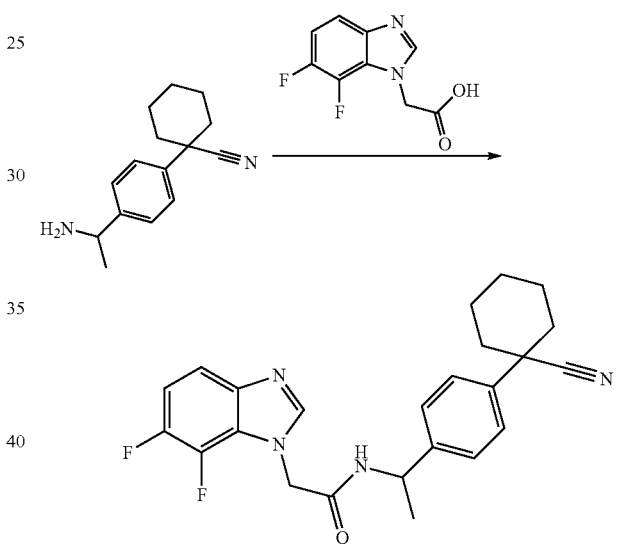

(+) and (−)-N-{1-[4-(1-Cyanocyclohexyl)phenyl]ethyl}-2-(6,7-difluoro-1H-benzimidazol-1-yl)acetamide N-{1-[4-(1-Cyanocyclohexyl)phenyl]ethyl}-2-(6,7-difluoro-1H-benzimidazol-1-yl)acetamide is synthesized according to example 5 by mixing (6,7-difluoro-1H-benzimidazol-1-yl)acetic acid (233 mg, 1.10 mmol) prepared according to scheme 2, 1-[4-(1-aminoethyl)phenyl]cyclohexanecarbonitrile (250 mg, 1.10 mmol) prepared according to scheme 11, Et₃N (111 mg, 1.10 mmol, 0.153 mL) and HATU (418 mg, 1.10 mmol) in MeCN (10.0 mL). The product is purified by HPLC: Gilson prep pumps, Flow rate: 30 ml/min, Column: Gemini (5μ) 21.2×50 mm, Mobile phase: A=water (10 mM NH₄CO₃) B=MeCN, (336 mg, 0.796 mmol, 72%). ¹H NMR (400 MHz, DMSO-D6) δ ppm 1.38 (d, J=7.03 Hz, 3H) 1.23-1.35 (m, 1H) 1.51-1.69 (m, 2H) 1.69-1.78 (m, 1H) 1.77-1.89 (m, 4H) 1.99-2.09 (m, 2H) 4.87-5.00 (m, 1H) 5.07 (s, 2H) 7.14-7.28 (m, 1H) 7.37 (d, J=8.40 Hz, 2H) 7.42-7.53 (m, 3H) 8.19 (s, 1H) 8.83 (d, J=7.81 Hz, 1H); MS [M+H], calcd: 424.0. found: 423.3.

Example 8

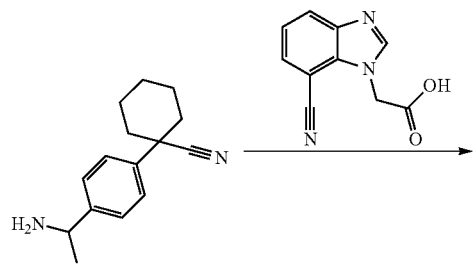
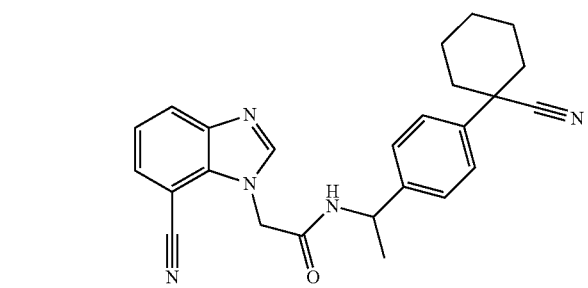

(+) and (−)-2-(7-Cyano-1H-benzimidazol-1-yl)-N-{1-[4-(1-cyanocyclohexyl)phenyl]ethyl}acetamide 2-(7-Cyano-1H-benzimidazol-1-yl)-N-{1-[4-(1-cyanocyclohexyl)phenyl]ethyl}acetamide is synthesized according to example 5 by mixing (7-cyano-1H-benzimidazol-1-yl)acetic acid (216 mg, 1.08 mmol) prepared according to scheme 3, 1-[4-(1-aminoethyl)phenyl]cyclohexanecarbonitrile (246 mg, 1.08 mmol) prepared according to scheme 11, Et$_3$N (328 mg, 3.24 mmol, 0.452 mL) and HATU (411 mg, 1.08 mmol) in MeCN (10.0 mL). The product is purified by HPLC: Gilson prep pumps, Flow rate: 30 ml/min, Column: Gemini (5μ) 21.2×50 mm, Mobile phase: A=water (10 mM NH$_4$CO$_3$) B=MeCN, (443 mg, 1.08 mmol, quantitative). $^1$H NMR (400 MHz, DMSO-D6) δ ppm 1.22-1.36 (m, 1H) 1.39 (d, J=6.84 Hz, 3H) 1.53-1.68 (m, 2H) 1.68-1.77 (m, 1H) 1.77-1.89 (m, 4H) 1.98-2.08 (m, 2H) 4.88-5.02 (m, 1H) 5.24 (dd, J=24.61, 17.77 Hz, 2H) 7.35 (t, J=7.91 Hz, 1H) 7.40 (d, J=8.40 Hz, 2 H) 7.46 (d, J=8.40 Hz, 2H) 7.72 (d, J=7.62 Hz, 1H) 8.01 (dd, J=8.20, 0.78 Hz, 1H) 8.35 (s, 1 H) 8.85 (d, J=7.81 Hz, 1H); MS [M+H], calcd: 412.0. found: 412.3.

The enantiomers are separated by chiral HPLC: Gilson prep pumps, Flow rate: 18 ml/min, Column: Chiralcel OD 21×250 mm (5μ), Mobile phase: A=Hexane (0.1% DEA) B=EtOH (0.1% DEA), α$_D$=−208 (c=2.2, MeOH) and α$_D$=+ 190 (c=2.4, MeOH).

Example 9

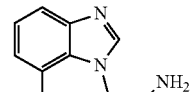
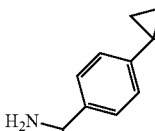
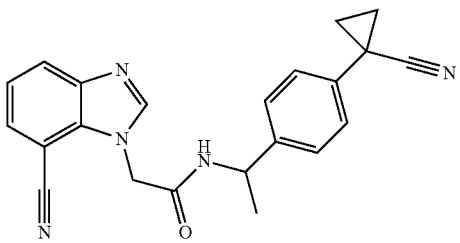

(+) and (−)-2-(7-Cyano-1H-benzimidazol-1-yl)-N-{1-[4-(1-cyanocyclopropyl)phenyl]ethyl}acetamide 2-(7-Cyano-1H-benzimidazol-1-yl)-N-{1-[4-(1-cyanocyclopropyl)phenyl]ethyl}acetamide is synthesized according to example 5 by mixing (7-cyano-1H-benzimidazol-1-yl)acetic acid (86.5 mg, 0.430 mmol) prepared according to scheme 3, 1-[4-(1-aminoethyl)phenyl]cyclopropanecarbonitrile (80.0 mg, 0.430 mmol) prepared according to scheme 10, Et$_3$N (131 mg, 1.29 mmol, 0.180 mL) and HATU (163 mg, 0.430 mmol) in MeCN (10.0 mL). The product is purified by HPLC: Gilson prep pumps, Flow rate: 30 ml/min, Column: Synergi Polar (5μ) 21.2×50 mm, Mobile phase: A=water (0.05% TFA) B=MeCN, (23.0 mg, 0.0623 mmol, 14%). $^1$H NMR (400 MHz, CHLOROFORM-D) δ ppm 1.35 (dd, J=7.81, 5.47 Hz, 2H) 1.49 (d, J=7.03 Hz, 3H) 1.68 (dd, J=7.42, 5.08 Hz, 2H) 5.00-5.13 (m, 3H) 6.65 (d, J=7.42 Hz, 1H) 7.22 (d, J=8.59 Hz, 2H) 7.29 (d, J=8.20 Hz, 2H) 7.33 (d, J=7.81 Hz, 1H) 7.59 (d, J=7.62 Hz, 1H) 7.96-8.06 (m, 2H); MS [M+H], calcd: 370.0. found: 370.0.

It is believed that the enantiomers could be separated by chiral HPLC: Gilson prep pumps, Flow rate: 18 ml/min, Column: Chiralcel OD 21×250 mm (5μ), Mobile phase: A=Hexane (0.1% DEA) B=EtOH (0.1% DEA), 80% A:20% B isocratic.

Example 10

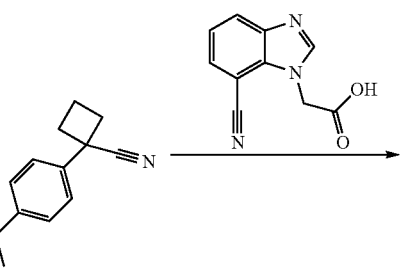
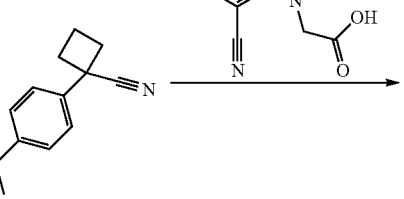

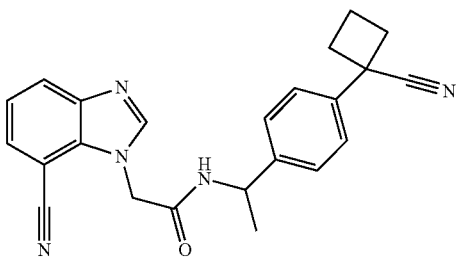

(+) and (−)-2-(7-Cyano-1H-benzimidazol-1-yl)-N-{1-[4-(1-cyanocyclobutyl)phenyl]ethyl}acetamide 2-(7-Cyano-1H-benzimidazol-1-yl)-N-{1-[4-(1-cyanocyclobutyl)phenyl]ethyl}acetamide is synthesized according to example 5 by mixing (7-cyano-1H-benzimidazol-1-yl)acetic acid (95.0 mg, 0.475 mmol) prepared according to scheme 3, 1-[4-(1-aminoethyl)phenyl]cyclobutanecarbonitrile (95 mg, 0.475 mmol) prepared according to scheme 9, Et$_3$N (144 mg, 1.43 mmol, 0.199 mL) and HATU (181 mg, 0.475 mmol) in MeCN (10.0 mL). The product is purified by HPLC: Gilson prep pumps, Flow rate: 30 ml/min, Column: Gemini (5μ) 21.2×50 mm, Mobile phase: A=water (10 mM NH$_4$CO$_3$) B=MeCN, (34.0 mg, 0.0888 mmol, 19%). $^1$H NMR (400 MHz, DMSO-D6) δ ppm 1.40 (d, J=7.03 Hz, 3H) 1.89-2.05 (m, 1 H) 2.15-2.34 (m, 1H) 2.52-2.66 (m, 2H) 2.66-2.80 (m, 2H) 4.88-5.01 (m, 1H) 5.25 (dd, J=22.66, 17.58 Hz, 2H) 7.31-7.46 (m, 5H) 7.71 (dd, J=7.62, 0.78 Hz, 1H) 8.01 (dd, J=8.01, 0.78 Hz, 1H) 8.36 (s, 1H) 8.87 (d, J=7.62 Hz, 1H); MS [M+H], calcd: 384.0. found: 384.2.

It is believed that the enantiomers could be separated by chiral HPLC: Gilson prep pumps, Flow rate: 18 ml/min, Column: Chiralcel OD 21×250 mm (5μ), Mobile phase: A=Hexane (0.1% DEA) B=EtOH (0.1% DEA), 80% A:20% B isocratic.

Example 11

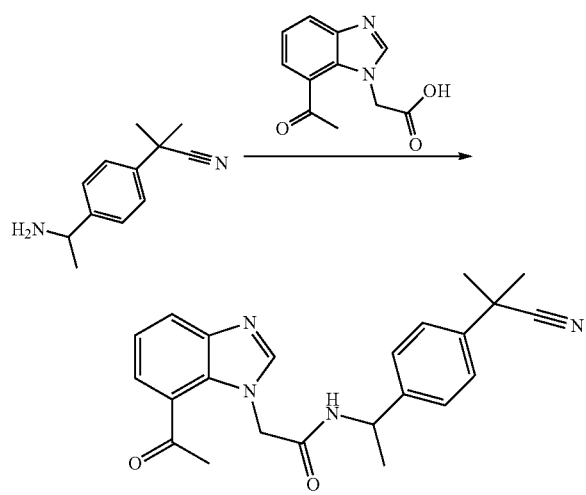

(R)(+) and (S)(−)-2-(7-Acetyl-1H-benzimidazol-1-yl)-N-{1-[4-(1-cyano-1-methylethyl)phenyl]ethyl}acetamide 2-(7-acetyl-1H-benzimidazol-1-yl)-N-{1-[4-(1-cyano-1-methylethyl)phenyl]ethyl}acetamide is synthesized according to example 5 by mixing 7-acetyl-1H-benzimidazol-1-ylacetic acid (90.0 mg, 0.413 mmol) prepared according to scheme 4, 2-[4-(1-aminoethyl)phenyl]-2-methylpropanenitrile (77.6 mg, 0.413 mmol) prepared according to scheme 6 and Et$_3$N (125 mg, 1.24 mmol, 0.173 mL) and HATU (157 mg, 0.413 mmol) in dry MeCN (10.0 mL). The product is purified by reverse phase HPLC: Gilson prep pumps; Flow rate: 30 ml/min; Column: Synergi Polar (4μ) 21.2×50 mm; Mobile phase: A=water (0.05% TFA) B=MeCN (49.5 mg, 0.128 mmol, 31.0%). $^1$H NMR (400 MHz, DMSO-D6) δ ppm 1.35 (d, J=7.03 Hz, 3H) 1.66 (s, 6H) 2.38 (s, 3H) 4.74-4.87 (m, J=7.23, 7.23 Hz, 1H) 5.14 (s, 2H) 7.26 (t, J=7.81 Hz, 1H) 7.35 (d, J=8.40 Hz, 2H) 7.45 (d, J=8.40 Hz, 2H) 7.71 (d, J=7.62 Hz, 1H) 7.85 (d, J=8.01 Hz, 1H) 8.21 (s, 1H) 8.65 (d, J=7.81 Hz, 1H); MS [M+H] calcd.: 389.19. found: 389.09.

The enantiomers are separated by chiral HPLC: Gilson prep pumps; Flow rate: 18 ml/min; Column: Chiralcel AD 21×250 mm (20μ); Mobile phase: A=Hexane (0.1% DEA) B=EtOH (0.1% DEA); α$_D$=+171 (c=2, MeOH) and α$_D$=−162 (c=2, MeOH).

Example 12

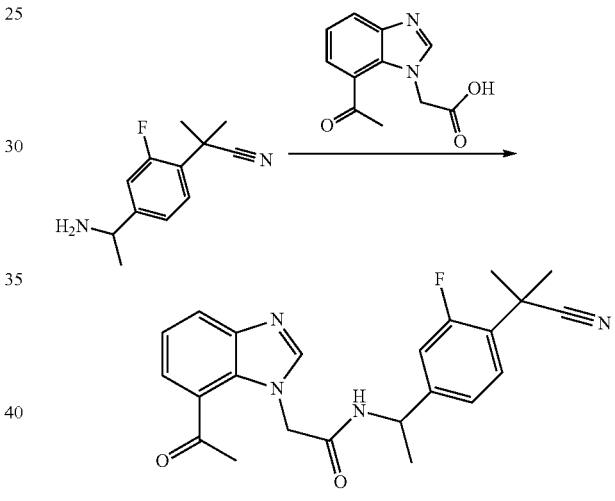

(+) and (−)-2-(7-Acetyl-1H-benzimidazol-1-yl)-N-{1-[4-(1-cyano-1-methylethyl)-3-fluorophenyl]ethyl}acetamide 2-(7-Acetyl-1H-benzimidazol-1-yl)-N-{1-[4-(1-cyano-1-methylethyl)-3-fluorophenyl]ethyl}acetamide is synthesized according to example 5 by mixing HATU (179 mg, 0.472 mmol), 7-acetyl-1H-benzimidazol-1-ylacetic acid (103 mg, 0.472 mmol) prepared according to scheme 4, 2-[4-(1-aminoethyl)-2-fluorophenyl]-2-methylpropanenitrile (97.0 mg, 0.472 mmol) prepared according to scheme 7 and Et$_3$N (143 mg, 1.42 mmol, 0.200 mL) in dry MeCN (10.0 mL). The product is purified by reverse phase HPLC: Gilson prep pumps; Flow rate: 30 ml/min; Column: Gemini (50 21.2×50 mm; Mobile phase: A=10.0 mM NH$_4$HCO$_3$ in H$_2$O B=MeCN (52.4 mg, 0.129 mmol, 27.0%). $^1$H NMR (400 MHz, DMSO-D6) δ ppm 1.36 (d, J=7.03 Hz, 3H) 1.70 (s, 6H) 2.40 (s, 3H) 4.72-4.90 (m, 1H) 5.17 (dd, J=21.48, 17.19 Hz, 2H) 7.18 (d, J=7.81 Hz, 1H) 7.21-7.32 (m, 2H) 7.40 (t, J=8.30 Hz, 1H) 7.72 (d, J=7.62 Hz, 1H) 7.86 (d, J=7.81 Hz, 1H) 8.22 (s, 1H) 8.72 (d, J=7.42 Hz, 1H); MS [M+H] calcd.: 407.18. found: 407.17.

The enantiomers are separated by chiral HPLC: Gilson prep pumps; Flow rate: 18 ml/min; Column: Chiralcel AD 21×250 mm (20μ); Mobile phase: A=Hexane (0.1% DEA) B=EtOH (0.1% DEA); α$_D$=+166 (c=2, MeOH) and α$_D$=−159 (c=1.60, MeOH).

Example 13

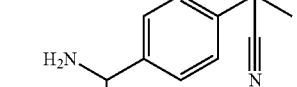

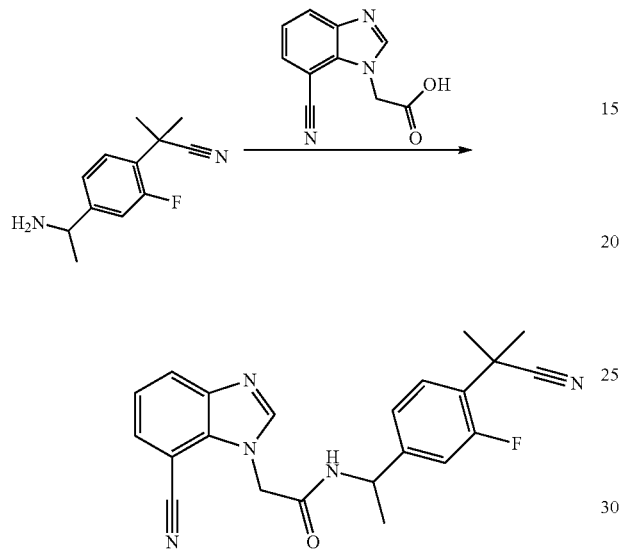

(+) and (−)-2-(7-Cyano-1H-benzimidazol-1-yl)-N-{1-[4-(1-cyano-1-methylethyl)-3-fluorophenyl]ethyl}acetamide 2-(7-Cyano-1H-benzimidazol-1-yl)-N-{1-[4-(1-cyano-1-methylethyl)-3-fluorophenyl]ethyl}acetamide is synthesized according to example 1 by mixing 2-[4-(1-Aminoethyl)-2-fluorophenyl]-2-methylpropanenitrile hydrochloride (260 mg, 0.94 mmol) prepared according to scheme 7, (7-cyano-1H-benzimidazol-1-yl)acetic acid (200 mg, 0.94 mmol) prepared according to scheme 3 and DMAP (228 mg, 1.89 mmol, 1.00 mL) and HATU (358 mg, 2.49 mmol) in DMF (5.0 mL). The product is purified by HPLC: Waters prep LCMS, Flow rate: 27 ml/min, Column: SynerSi (4μ) Polar RP, 21.2×50 mm, Mobile phase: A=water (0.05% TFA) B=MeCN, Gradient used 40% to 60% B in A, in 10 min. The fractions are combined, NaOH 1N is added and the desired compound is extracted with ethyl acetate. The combined organic fractions are concentrated under reduced pressure to yield the product (69 mg, 1.77 mmol, 19%). $^1$H NMR (400 MHz, METHANOL-D4) δ ppm 1.50 (d, J=7.03 Hz, 3H) 1.72-1.78 (m, 6H) 5.02 (q, J=6.97 Hz, 1H) 5.31 (d, J=17.58 Hz, 1H) 5.36 (d, J=17.58 Hz, 1H) 7.17-7.25 (m, 2H) 7.39 (dd, J=8.20, 7.62 Hz, 1H) 7.43 (t, J=8.40 Hz, 1H) 7.67 (dd, J=7.62, 0.78 Hz, 1H) 7.97 (dd, J=8.20, 0.98 Hz, 1H) 8.26 (s, 1H); MS [M+H], calcd: 390.2. found: 390.3.

The enantiomers are separated by chiral HPLC: Gilson prep pumps, Flow rate: 18 ml/min, Column: Chiralcel® AD 21×250 mm (200, Mobile phase: A=Hexane (0.1% DEA) B=EtOH (0.1% DEA), 70% A:30% B isocratic α$_D$=−173 (c=5.5, MeOH) and α$_D$=+180 (c=5.7, MeOH)

Example 14

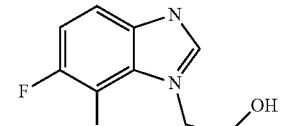

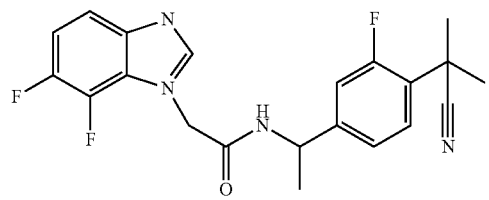

N-{1-[4-(1-cyano-1-methylethyl)-3-fluorophenyl]ethyl}-2-(6,7-difluoro-1H-benzimidazol-1-yl)acetamide The amide is synthesized according to modified example 1 by mixing (6,7-difluoro-1H-benzimidazol-1-yl)acetic acid (781 mg, 3.68 mmol) prepared according to scheme 2, 2-[4-(1-Aminoethyl)-2-fluorophenyl]-2-methylpropanenitrile hydrochloride (1.07 mg, 4.41 mmol) prepared according to scheme 7, Et$_3$N (1.23 mL, 8.82 mmol) and HATU (1.68 g, 4.41 mmol) in DMF (15.0 mL). The product is purified by HPLC: Gilson prep pumps, Flow rate: 30 ml/min, Column: Gemini (5u) 21.2×50 mm, Mobile phase: A=water (0.075% TFA) B=MeCN (0.075% TFA), (565 mg as TFA salt, 1.10 mmol, 30%); $^1$H NMR (400 MHz, DMSO-D6) δ ppm 1.38 (d, J=6.84 Hz, 3H), 1.71 (s, 6H), 4.87-5.00 (m, J=7.23, 7.23 Hz, 1H), 5.09 (s, 2H), 7.16-7.29 (m, 3H), 7.36-7.51 (m, 2H), 8.19 (s, 1H), 8.86 (d, J=7.62 Hz, 1H). MS [M+H], calcd: 401.4. found: 401.3.

The enantiomers are separated by chiral HPLC: Gilson prep pumps, flow rate: 18 ml/min, column: Chiralpak OD 21×250 mm (5 μA mobile phase: A=Hexane (0.1% DEA) B=iPrOH (0.1% DEA).

Example 15

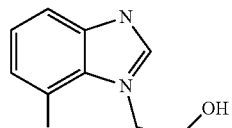

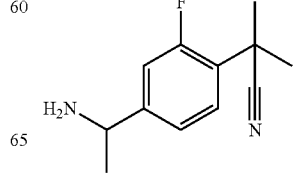

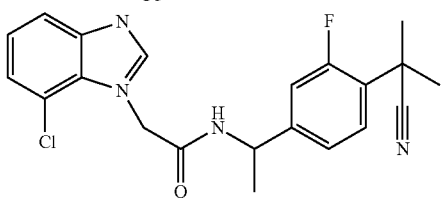

2-(7-chloro-1H-benzimidazol-1-yl)-N-{1-[4-(1-cy-ano-1-methylethyl)-3-fluorophenyl]ethyl}acetamide The amide is synthesized according to example 1 by mixing (7-chloro-1H-benzimidazol-1-yl)acetic acid (521 mg, 2.48 mmol) prepared according to scheme 1, 2-[4-(1-Aminoethyl)-2-fluorophenyl]-2-methylpropanenitrile hydrochloride 721 mg, 2.97 mmol) prepared according to scheme 7, Et$_3$N (824 μL, 5.95 mmol) and HATU (1.13 g, 2.97 mmol) in DMF (10.0 mL). The product is purified by HPLC: Gilson prep pumps, Flow rate: 30 ml/min, Column: Gemini (5u) 21.2×50 mm, Mobile phase: A=water (0.075% TFA) B=MeCN (0.075% TFA), (421 mg as TFA salt, 0.82 mmol, 33%); $^1$H NMR (400 MHz, DMSO-D6) δ ppm 1.38 (d, J=7.03 Hz, 3H), 1.64-1.76 (m, 6H), 4.88-4.98 (m, 1H), 5.27 (s, 2H), 7.18-7.28 (m, 3H), 7.28-7.33 (m, 1 H), 7.41 (t, J=8.30 Hz, 1H), 7.65 (d, J=7.81 Hz, 1H), 8.47 (s, 1H), 8.85 (d, J=7.62 Hz, 1H). MS [M+H], calcd: 399.9. found: 399.3.

The enantiomers are separated by chiral HPLC: Gilson prep pumps, flow rate: 18 ml/min, column: Chiralpak OD 21×250 mm (5μ), mobile phase: A=Hexane (0.1% DEA) B=iPrOH (0.1% DEA).

Example 16

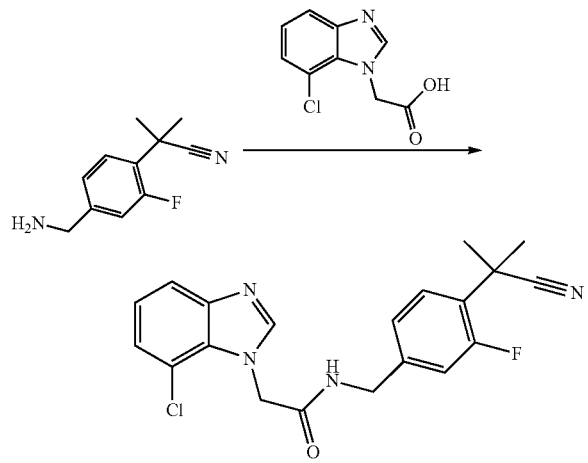

2-(7-Chloro-1H-benzimidazol-1-yl)-N-[4-(1-cyano-1-methylethyl)-3-fluorobenzyl]acetamide 2-(7-Chloro-1H-benzimidazol-1-yl)-N-[4-(1-cyano-1-methylethyl)-3-fluorobenzyl]acetamide is synthesized according to example 14 with (7-chloro-1H-benzimidazol-1-yl)acetic acid (150 mg, 0.712 mmol) prepared according to scheme 1, and 2-[4-(aminomethyl)-2-fluorophenyl]-2-methylpropanenitrile hydrochloride (196 mg, 0.855 mmol) prepared according to scheme 8, Et$_3$N (238 μL, 1.71 mmol) and HATU (325 mg, 0.855 mmol) in DMF (3.0 mL). The product is purified by HPLC: Gilson prep pumps, Flow rate: 30 ml/min, Column: Gemini (50 21.2×50 mm, Mobile phase: A=water (0.075% TFA) B=MeCN (0.075% TFA). Yield=14 mg as TFA salt, 0.035 mmol, 5%); $^1$H NMR (400 MHz, DMSO-D6) δ ppm 1.67 (s, 6H), 4.30 (d, J=5.86 Hz, 2H), 5.24 (s, 2H), 7.10-7.22 (m, 3H), 7.23-7.28 (m, 1H), 7.38 (t, J=8.40 Hz, 1 H), 7.62 (d, J=7.81 Hz, 1H), 8.31 (s, 1H), 8.81 (s, 1H). MS [M+H], calcd: 385.1. found: 385.0.

Example 17

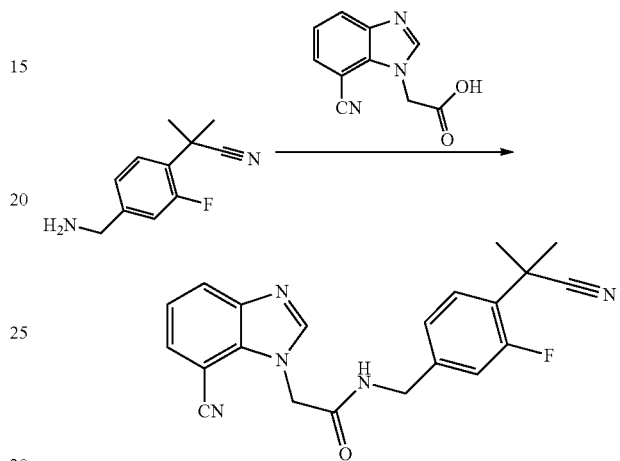

2-(7-Cyano-1H-benzimidazol-1-yl)-N-[4-(1-cyano-1-methylethyl)-3-fluorobenzyl]acetamide 2-(7-cyano-1H-benzimidazol-1-yl)-N-[4-(1-cyano-1-methylethyl)-3-fluorobenzyl]acetamide is synthesized according to example 14 with (7-cyano-1H-benzimidazol-1-yl)acetic acid (150 mg, 0.746 mmol) prepared according to scheme 3, 2-[4-(aminomethyl)-2-fluorophenyl]-2-methylpropanenitrile hydrochloride (205 mg, 0.896 mmol) prepared according to scheme 8, Et$_3$N (250 μL, 1.79 mmol) and HATU (341 mg, 0.896 mmol) in DMF (3.0 mL). The product is purified by HPLC: Gilson prep pumps, Flow rate: 30 ml/min, Column: Gemini (50 21.2×50 mm, Mobile phase: A=water (0.075% TFA) B=MeCN (0.075% TFA). Yield=21 mg as TFA salt, 0.043 mmol, 6%); $^1$H NMR (400 MHz, DMSO-D6) δ ppm 1.62-1.71 (m, 6H), 4.32 (d, J=5.86 Hz, 2H), 5.26 (s, 2H), 7.13-7.25 (m, 2H), 7.29-7.41 (m, 2H), 7.71 (d, J=7.42 Hz, 1H), 8.00 (d, J=8.01 Hz, 1H), 8.36 (s, 1H), 8.84-8.93 (m, 1H). MS [M+H], calcd: 376.2. found: 376.0.

Example 18

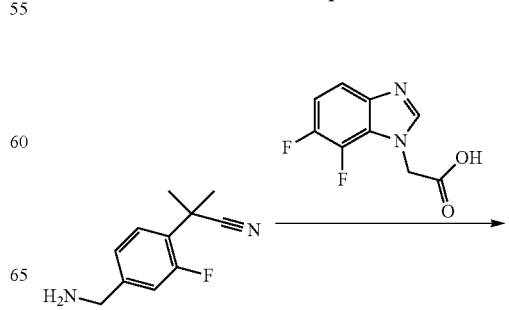

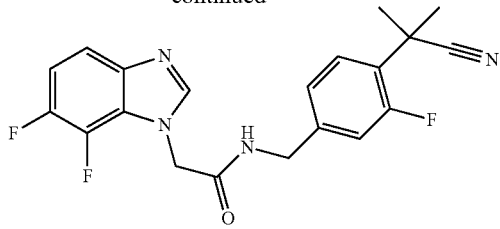

N-[4-(1-cyano-1-methylethyl)-3-fluorobenzyl]-2-(6,
7-difluoro-1H-benzimidazol-1-yl)acetamide N-[4-(1-Cyano-1-methylethyl)-3-fluorobenzyl]-2-(6,7-difluoro-1H-benzimidazol-1-yl)acetamide is synthesized according to example 14 with (6,7-difluoro-1H-benzimidazol-1-yl)acetic acid (150 mg, 0.707 mmol) prepared according to scheme 2, 2-[4-(aminomethyl)-2-fluorophenyl]-2-methylpropanenitrile hydrochloride (194 mg, 0.848 mmol) prepared according to scheme 8, Et$_3$N (237 μL, 1.70 mmol) and HATU (323 mg, 0.848 mmol) in DMF (3.0 mL). The product is purified by HPLC: Gilson prep pumps, Flow rate: 30 ml/min, Column: Gemini (50 21.2×50 mm, Mobile phase: A=water (0.075% TFA) B=MeCN (0.075% TFA). Yield=25 mg as TFA salt, 0.05 mmol, 7%). $^1$H NMR (400 MHz, DMSO-D6) δ ppm 1.74-1.87 (m, 6H), 4.43 (d, J=5.66 Hz, 2H), 5.22 (s, 2H), 7.19-7.40 (m, 2H), 7.45-7.61 (m, 2H), 8.34 (s, 1H), 8.91-9.04 (m, 1H). MS [M+H], calcd: 387.1. found: 387.0.

Example 19

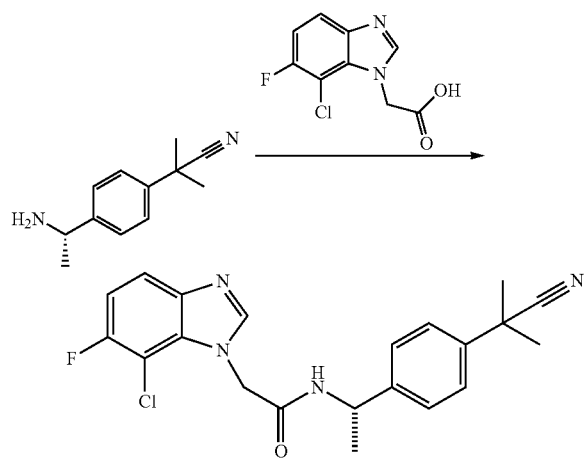

(S)(−)-2-(7-chloro-6-fluoro-1H-benzimidazol-1-yl)-
N-{1-[4-(1-cyano-1-methylethyl)phenyl]
ethyl}acetamide A mixture of (7-chloro-6-fluoro-1H-benzimidazol-1-yl) acetic acid (1.00 g, 4.39 mmol) prepared according to scheme 12, (S)(−)-2-{4-[1-aminoethyl]phenyl}-2-methylpropanenitrile (825 mg 4.39 mmol) prepared according to scheme 20 or 21 and Et$_3$N (1.33 g, 13.2 mmol, 1.84 mL) is stirred in MeCN (50.0 mL). HATU (1.67 g, 4.39 mmol) is added, and, after 2 hours of stirring, the mixture is diluted with 1N NaOH (100 mL) and then extracted 4 times with EtOAc (4×75.0 mL). The organic phases are combined and dried over Na$_2$SO$_4$. The mixture is filtered and concentrated. The product is purified by a Gilson prep pump, flow rate: 30 ml/min, column: Gemini™ (5u) 21.2×50 mm, mobile phase: A=10 mM ammonium bicarbonate, B=MeCN (1.01 g, 58%). $^1$H NMR (400 MHz, DMSO-D6) δ ppm 1.39 (d, J=7.03 Hz, 3H) 1.66 (s, 6H) 4.92 (quint, J=7.23 Hz, 1H) 5.19 (s, 2H) 7.23 (dd, J=10.16, 8.98 Hz, 1H) 7.37 (d, J=8.20 Hz, 2 H) 7.47 (d, J=8.59 Hz, 2H) 7.63 (dd, J=8.79, 4.49 Hz, 1H) 8.21 (s, 1H) 8.81 (d, J=7.81 Hz, 1 H) MS [M+H], calcd: 399.1. found: 399.2, [α]$_D$=−165 (c=1.02 METHANOL) HRMS (ESI+) calcd for C21H21ClFN4O 399.13824 [M+H]+ found 399.13832.

Example 20

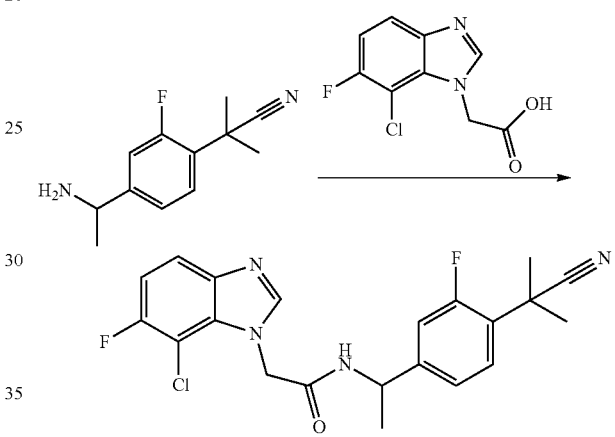

(+) and (−) 2-(7-chloro-6-fluoro-1H-benzimidazol-1-
yl)-N-{1-[4-(1-cyano-1-methylethyl)-3-fluorophe-
nyl]ethyl}acetamide A mixture of (7-chloro-6-fluoro-1H-benzimidazol-1-yl) acetic acid (210 mg, 0.921 mmol) prepared according to scheme 12, 2-{4-[1-aminoethyl]-2-fluorophenyl}-2-methylpropanenitrile (190 mg 0.921 mmol)) prepared according to scheme 7 and Et$_3$N (280 mg, 2.76 mmol, 0.39 mL) is stirred in MeCN (10.0 mL). HATU (350 mg, 0.921 mmol) is added, and after 2 hours of stirring, the mixture is diluted with 1N NaOH (40.0 mL) and then extracted 4 times with EtOAc (4×40.0 mL). The organic phases are combined and dried over MgSO$_4$. The mixture is filtered and concentrated. The product is purified by a Gilson prep pump, flow rate: 30 ml/min, column: Synergi Polar (4u) 21.2×50 mm, mobile phase: A=water (0.1% TFA), B=MeCN (206 mg, 54%). $^1$H NMR (400 MHz, DMSO-D6) δ ppm 1.38 (d, J=6.84 Hz, 3H) 1.71 (s, 6H) 4.85-5.00 (m, J=7.13, 7.13 Hz, 1H) 5.21 (s, 2H) 7.15-7.31 (m, 3H) 7.42 (t, J=8.30 Hz, 1H) 7.63 (dd, J=8.89, 4.39 Hz, 1H) 8.21 (s, 1H) 8.84 (d, J=7.81 Hz, 1H). The enantiomers are separated on a chiral AD column, eluting with 30% EtOH (0.1% DIEA) and hexanes 70% (0.1% DIEA), MS [M+H], calcd: 417.1. found: 417.3 [α]$_D$=+154 (c=13, MeOH) and [α]$_D$=−155 (c=15, MeOH).

It is believed that the enantiomers could be separated by chiral HPLC: Gilson prep pumps, Flow rate: 18 ml/min, Column: Chiralcel OD 21×250 mm (5µ), Mobile phase: A=Hexane (0.1% DEA) B=EtOH (0.1% DEA), 80% A:20% B isocratic.

Example 21

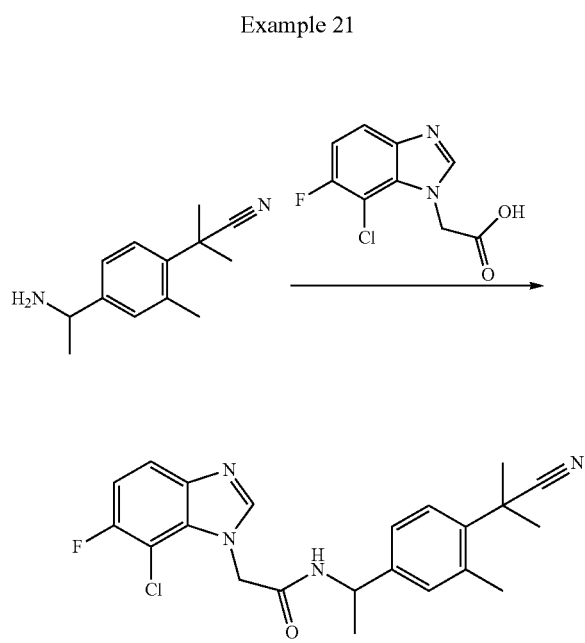

(+) and (−)-2-(7-Chloro-6-fluoro-1H-benzimidazol-1-yl)-N-{1-[4-(1-cyano-1-methylethyl)-3-methylphenyl]ethyl}acetamide To a solution of (7-chloro-6-fluoro-1H-benzimidazol-1-yl)acetic acid (100 mg, 0.44 mmol) prepared according to scheme 12, 2-{4-[1-aminoethyl]-2-methylphenyl}-2-methylpropanenitrile (88.5 mg 0.44 mmol) prepared according to scheme 16 and DMAP (106 mg, 0.88 mmol) stirred in anhydrous DMF (2.0 mL) is added HATU (166 mg, 0.44 mmol) after 18 hours of stirring, the mixture is diluted with methanol (200 µL) the solution is purified directly on a preparative LCMS system equipped with a Synergi Polar (4u) 21.2×50 mm column, mobile phase: A=water (0.1% TFA), B=MeCN using a short 40 to 60% B 10 min. gradient method. The pure fractions are combined the TFA neutralized with a 4N NaOH solution and then extracted with ethyl acetate which is separated dried over anhydrous $Na_2SO_4$, filtered and concentrated under reduced pressure to provide the expected product (+) and (−)-2-(7-chloro-6-fluoro-1H-benzimidazol-1-yl)-N-{1-[4-(1-cyano-1-methylethyl)-3-methylphenyl]ethyl}acetamide (290 mg, 53%) as a white solid. 1H NMR (400 MHz, METHANOL-D4) δ ppm 1.48 (d, J=7.03 Hz, 3H) 1.76 (s, 6H) 2.61 (s, 3H) 4.99 (q, J=7.03 Hz, 1H) 5.19-5.36 (m, 2H) 7.13-7.25 (m, 3H) 7.33 (d, J=8.20 Hz, 1H) 7.59 (dd, J=8.98, 4.30 Hz, 1H) 8.14 (s, 1H), MS [M+H], calcd: 413.2, found: 413.3.

It is believed that the enantiomers could be separated by chiral HPLC: Gilson prep pumps, Flow rate: 18 ml/min, Column: Chiralcel OD 21×250 mm (5µ), Mobile phase: A=Hexane (0.1% DEA) B=EtOH (0.1% DEA), 80% A:20% B isocratic.

Example 22

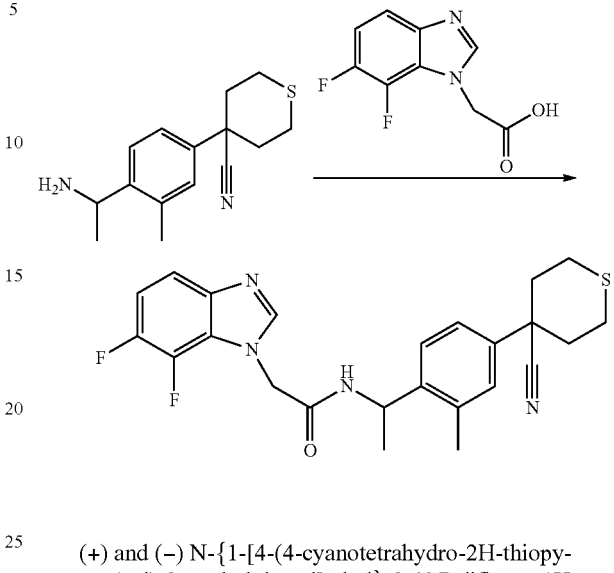

(+) and (−) N-{1-[4-(4-cyanotetrahydro-2H-thiopyran-4-yl)-2-methylphenyl]ethyl}-2-(6,7-difluoro-1H-benzimidazol-1-yl)acetamide The amide is synthesized according to example 1 by mixing (6,7-difluoro-1H-benzimidazol-1-yl)acetic acid (96 mg, 0.45 mmol) prepared according to scheme 2, 4-[4-(1-aminoethyl)-3-methylphenyl]tetrahydro-2H-thiopyran-4-carbonitrile (129 mg, 0.50 mmol) prepared according to scheme 14, $Et_3N$ (0.69 µL, 0.50 mmol) and HATU (189 mg, 0.50 mmol) in MECN (3.0 mL). The compound is purified by silica gel column chromatography (10% MeOH in DCM) (121 mg, 59%). $^1$H NMR (400 MHz, DMSO-D6) δ ppm 1.35 (d, J=7.03 Hz, 3H), 2.05-2.16 (m, 2H), 2.26-2.35 (m, 5H), 2.72-2.81 (m, J=14.06 Hz, 2H), 2.88-2.99 (m, J=12.50, 12.50 Hz, 2H), 5.01-5.11 (m, 3H), 7.16-7.26 (m, 1H), 7.30 (s, 1H), 7.33-7.38 (m, 1H), 7.39-7.48 (m, 2 H), 8.18 (s, 1H), 8.84 (d, J=7.42 Hz, 1H). MS [M+H], calcd: 455.5. found: 455.3.

It is believed that the enantiomers could be separated by chiral HPLC: Gilson prep pumps, Flow rate: 18 ml/min, Column: Chiralcel OD 21×250 mm (5µ), Mobile phase: A=Hexane (0.1% DEA) B=EtOH (0.1% DEA), 80% A:20% B isocratic.

Example 23

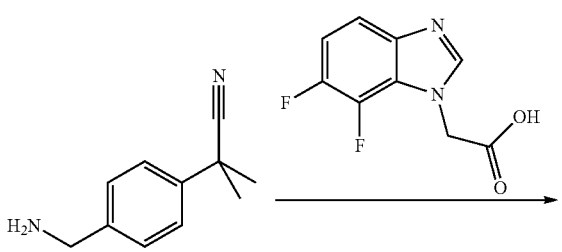

-continued

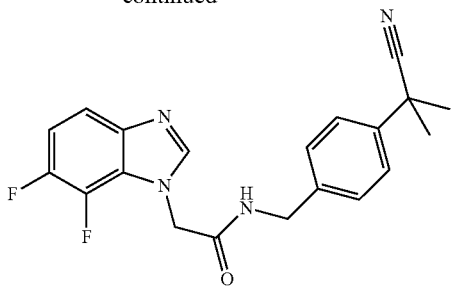

N-[4-(1-cyano-1-methylethyl)benzyl]-2-(6,7-difluoro-1H-benzimidazol-1-yl)acetamide (6,7-difluoro-1H-benzimidazol-1-yl)acetic acid (42 mg, 0.2 mmol) prepared according to scheme 2 is dissolved in CH$_2$Cl$_2$ (2 mL). Triethylamine (83 μL, 0.6 mmol) is added, followed by pivaloyl chloride (25 μL, 0.2 mmol). After 30 minutes, 2-[4-(aminomethyl)phenyl]-2-methylpropanenitrile (35 mg, 0.2 mmol) prepared according to scheme 18 is added dissolved in 1 mL of CH$_2$Cl$_2$. The mixture is stirred overnight at room temperature, concentrated under vacuo and purified on HPLCMS: Waters prep LCMS, 27 ml/min, Column: X-Bridge Prep C18 OBD, 30×50 mm, 5 μm particle size, Mobile phase: A=water (10 mM NH$_4$CO$_3$) B=MeCN, Gradient used 40% to 60% B in A, in 10 min. The fractions are combined and freeze dried to give the desired product (17 mg, 0.05 mmol, 25%). MS (ESI) (M+1) 383.3. $^1$H NMR (400 MHz, DMSO-D6) δ ppm 1.65 (s, 6H) 2.30 (s, 3H) 4.29 (d, J=5.47 Hz, 2H) 5.09 (s, 2H) 7.19-7.31 (m, 3H) 7.32-7.35 (m, 1H) 7.47 (dd, J=8.98, 3.91 Hz, 1H) 8.22 (s, 1H) 8.66-8.74 (m, 1H).

Example 24

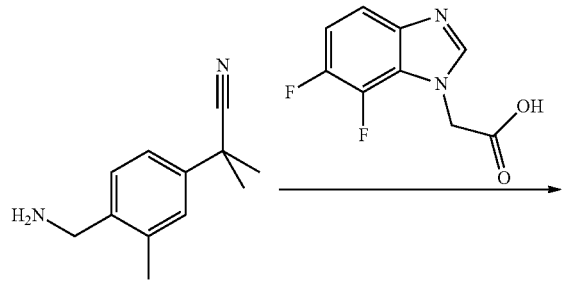

N-[4-(1-cyano-1-methylethyl)-2-methylbenzyl]-2-(6,7-difluoro-1H-benzimidazol-1-yl)acetamide (6,7-difluoro-1H-benzimidazol-1-yl)acetic acid (91 mg, 0.43 mmol) prepared according to scheme 2 is dissolved in DCM (3 mL). DIPEA (0.1 mL) is added, followed by pivaloyl chloride (53 μL, 0.43 mmol). After 1 hour, 2-[4-(aminomethyl)-3-methylphenyl]-2-methylpropanenitrile (80 mg, 0.43 mmol) prepared according to scheme 19 is added. The mixture is stirred overnight at room temperature, concentrated under vacuo and purified on HPLCMS: Waters prep LCMS, 27 ml/min, Column: X-Bridge Prep C18 OBD, 30×50 mm, 5 μm particle size, Mobile phase: A=water (10 mM NH$_4$CO$_3$) B=MeCN, Gradient used 30% to 50% B in A, in 10 min. The fractions are combined and freeze dried to give the desired product (59 mg, 0.15 mmol, 35%). MS (ESI) (M+1) 369.2. $^1$H NMR (400 MHz, DMSO-D6) δ ppm 1.67 (s, 6H) 4.33 (d, J=5.86 Hz, 2H) 5.10 (s, 2H) 7.23 (ddd, J=11.62, 8.89, 7.62 Hz, 1H) 7.32 (d, J=8.59 Hz, 2H) 7.44-7.51 (m, 3H) 8.21 (s, 1H) 8.80 (t, J=5.86 Hz, 1H).

Example 25

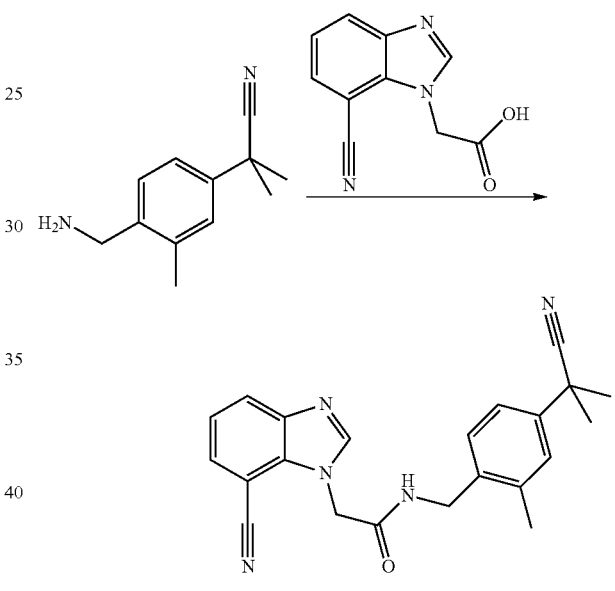

2-(7-cyano-1H-benzimidazol-1-yl)-N-[4-(1-cyano-1-methylethyl)-2-methylbenzyl]acetamide (7-cyano-1H-benzimidazol-1-yl)acetic acid (86 mg, 0.43 mmol) prepared according to scheme 3 is dissolved in DCM (3 mL). DIPEA (0.1 mL) is added, followed by pivaloyl chloride (53 μL, 0.43 mmol). After 1 hour, 2-[4-(aminomethyl)-3-methylphenyl]-2-methylpropanenitrile (80 mg, 0.43 mmol) prepared according to scheme 19 is added. The mixture is stirred overnight at room temperature, concentrated under vacuo and purified on HPLCMS: Waters prep LCMS, 27 ml/min, X-Bridge Prep C18 OBD, 30×50 mm, 5 μm particle size, Mobile phase: A=water (10 mM NH$_4$CO$_3$) B=MeCN, Gradient used 30% to 50% B in A, in 10 min. The fractions are combined and freeze dried to give the desired product (47 mg, 0.13 mmol, 30%). MS (ESI) (M+1) 372.3. $^1$H NMR (400 MHz, DMSO-D6) δ ppm 1.65 (s, 6H) 2.31 (s, 3H) 4.29 (d, J=5.08 Hz, 2H) 5.26 (s, 2H) 7.25-7.29 (m, 1H) 7.30-7.40 (m, 3H) 7.73 (dd, J=7.62, 0.98 Hz, 1H) 8.03 (dd, J=8.20, 0.78 Hz, 1H) 8.38 (s, 1H) 8.74 (t, J=5.27 Hz, 1H).

Example 26

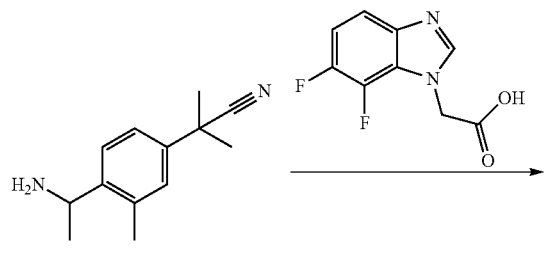

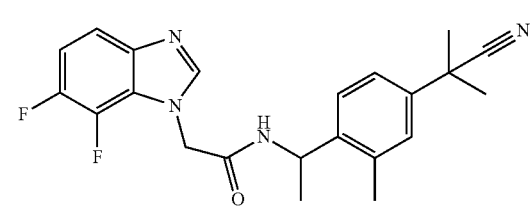

(+) and (−)-N-{1-[4-(1-cyano-1-methylethyl)-2-methylphenyl]ethyl}-2-(6,7-difluoro-1H-benzimidazol-1-yl)acetamide To a solution of (6,7-difluoro-1H-benzimidazol-1-yl)acetic acid (250 mg, 1.18 mmol) prepared according to scheme 2, 2-[4-(1-aminoethyl)-3-methylphenyl]-2-methylpropanenitrile (202 mg 1.18 mmol) prepared according to scheme 15 and DMAP (285 mg, 2.35 mmol) stirred in anhydrous DMF (4.0 mL) is added HATU (448 mg, 1.18 mmol) after 18 hours of stirring, the mixture is diluted with 1N NaOH (40.0 mL) and then extracted 4 times with EtOAc (4×40.0 mL). The organic phases are combined and dried over MgSO$_4$. The mixture is filtered and concentrated. The product is purified on a preparative LCMS system equipped with a Synergi Polar (4u) 21.2×50 mm column, mobile phase: A=water (ammonium carbonate buffer 0.01 M), B=MeCN using a short 40 to 60% B 10 min. gradient high pH method. The pure fractions are combined then extracted with ethyl acetate which is separated dried over anhydrous Na$_2$SO$_4$, filtered and concentrated under reduced pressure to provide the expected product N-{1-[4-(1-cyano-1-methylethyl)-2-methylphenyl]ethyl}-2-(6,7-difluoro-1H-benzimidazol-1-yl)acetamide (350 mg, 75%) as a white solid. 1H NMR (400 MHz, METHANOL-D4) d ppm 1.44 (d, J=6.84 Hz, 3H) 1.66 (s, 6H) 2.36 (s, 3H) 5.06 (d, J=16.99 Hz, 1H) 5.11 (d, J=16.99 Hz, 1H) 5.20 (q, J=7.03 Hz, 1H) 7.14 (ddd, J=11.38, 8.84, 7.52 Hz, 1H) 7.26 (d, J=2.15 Hz, 1H) 7.32 (dd, J=6.05, 2.15 Hz, 1H) 7.37-7.43 (m, 2H) 8.09 (s, 1H). MS [M+H], calcd: 397.2. found: 397.3. The enantiomers are separated on a chiral OD column, using methanol and CO$_2$ as the mobile phase.

Alternatively the chiral (−) N-{1-[4-(1-cyano-1-methylethyl)-2-methylphenyl]ethyl}-2-(6,7-difluoro-1H-benzimidazol-1-yl)acetamide can be prepared directly using the chiral intermediate (−)2-[4-[1-aminoethyl]-3-methyl-phenyl]-2-methyl-propanenitrile prepared as described in scheme 23 and the corresponding acid above.

Example 27

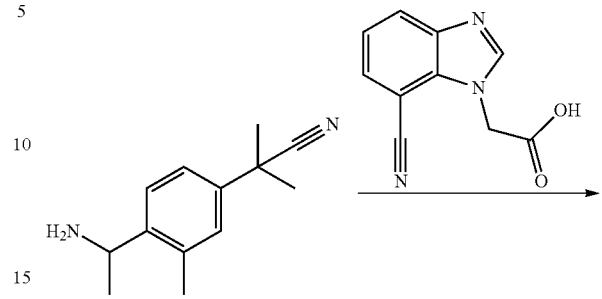

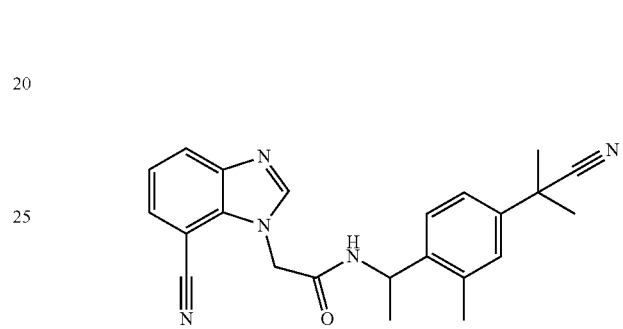

(+) and (−)-2-(7-cyano-1H-benzimidazol-1-yl)-N-{1-[4-(1-cyano-1-methylethyl)-2-methylphenyl]ethyl}acetamide To a solution of (7-cyano-1H-benzimidazol-1-yl)acetic acid (250 mg, 1.24 mmol) prepared according to scheme 3, 2-[4-(1-aminoethyl)-3-methylphenyl]-2-methylpropanenitrile (251 mg 1.24 mmol) prepared according to scheme 15 and DMAP (150 mg, 1.24 mmol) stirred in anhydrous DMF (4.0 mL) is added HATU (473 mg, 1.24 mmol) after 18 hours of stirring, the mixture is diluted with Methanol (200 µL) the solution is purified directly on a preparative LCMS system equipped with a Synergi Polar (4u) 21.2×50 mm column, mobile phase: A=water (0.1% TFA), B=MeCN using a short 40 to 60% B 10 min. gradient method. The pure fractions are combined the TFA neutralized with a 4 N NaOH solution and then extracted with ethyl acetate which is separated dried over anhydrous Na$_2$SO$_4$, filtered and concentrated under reduced pressure to provide the expected product 2-(7-cyano-1H-benzimidazol-1-yl)-N-{1-[4-(1-cyano-1-methylethyl)-2-methylphenyl]ethyl}acetamide (206 mg, 43%) as a white solid. 1H NMR (400 MHz, METHANOL-D4) δ ppm 1.45 (d, J=6.84 Hz, 3H) 1.66 (s, 6H) 2.37 (s, 3H) 5.20 (q, J=6.84 Hz, 1H) 5.30 (s, 2H) 7.25 (d, J=1.95 Hz, 1H) 7.32 (dd, J=8.20, 2.15 Hz, 1H) 7.38 (dd, J=8.11, 7.71 Hz, 1H) 7.44 (d, J=8.20 Hz, 1H) 7.67 (dd, J=7.42, 0.78 Hz, 1H) 7.96 (dd, J=8.20, 0.98 Hz, 1H) 8.24 (s, 1H), MS [M+H], calcd: 386.2. found: 386.2.

Alternatively the chiral (−)-2-(7-cyano-1H-benzimidazol-1-yl)-N-{1-[4-(1-cyano-1-methylethyl)-2-methylphenyl]ethyl}acetamide could be prepared directly using the chiral intermediate (−)2-[4-[1-aminoethyl]-3-methyl-phenyl]-2-methyl-propanenitrile prepared as described in scheme 23 and the corresponding acid above.

Example 28

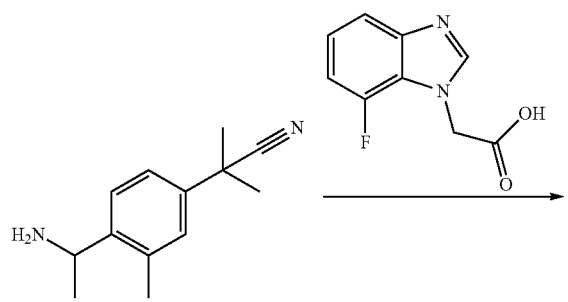

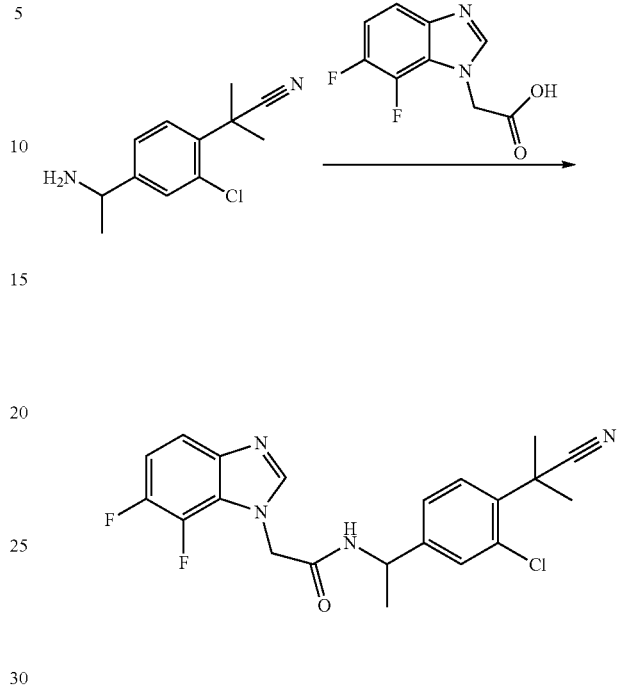

(+) and (−)-N-{1-[4-(1-cyano-1-methylethyl)-2-methylphenyl]ethyl}-2-(7-fluoro-1H-benzimidazol-1-yl)acetamide To a solution of (7-fluoro-1H-benzimidazol-1-yl)acetic acid (250 mg, 1.29 mmol) prepared according to scheme 5, 2-[4-(1-aminoethyl)-3-methylphenyl]-2-methylpropanenitrile (260 mg 1.29 mmol) prepared according to scheme 15 and DMAP (156 mg, 1.29 mmol) stirred in anhydrous DMF (4.0 mL) is added HATU (490 mg, 1.29 mmol) after 18 hours of stirring, the mixture is diluted with Methanol (200 µL) the solution is purified directly on a preparative LCMS system equipped with a Synergi Polar (4u) 21.2×50 mm column, mobile phase: A=water (0.1% TFA), B=MeCN using a short 40 to 60% B 10 min. gradient method. The pure fractions are combined the TFA neutralized with a 4N NaOH solution and then extracted with ethyl acetate which is separated dried over anhydrous $Na_2SO_4$, filtered and concentrated under reduced pressure to provide the expected product (+) and (−)-N-{1-[4-(1-cyano-1-methylethyl)-2-methylphenyl]ethyl}-2-(7-fluoro-1H-benzimidazol-1-yl)acetamide (306 mg, 63%) as a white solid. 1H NMR (400 MHz, METHANOL-D4) δ ppm 1.44 (d, J=6.84 Hz, 3H) 1.66 (s, 6H) 2.35 (s, 3H) 5.02-5.14 (m, 2H) 5.19 (q, J=7.03 Hz, 1H) 6.99 (dd, J=11.52, 7.42 Hz, 1H) 7.19 (dt, J=8.15, 4.98 Hz, 1H) 7.26 (d, J=2.15 Hz, 1H) 7.32 (dd, J=8.01, 2.34 Hz, 3H) 7.39 (d, J=8.20 Hz, 1H) 7.45 (d, J=7.62 Hz, 1H) 8.09 (s, 1H), MS [M+H], calcd: 379.2. found: 379.2.

Alternatively the chiral (−)-N-{1-[4-(1-cyano-1-methylethyl)-2-methylphenyl]ethyl}-2-(7-fluoro-1H-benzimidazol-1-yl)acetamide could be prepared directly using the chiral intermediate (−)2-[4-[1-aminoethyl]-3-methyl-phenyl]-2-methyl-propanenitrile prepared as described in scheme 23 and the corresponding acid above.

Example 29

(+) and (−)-N-{1-[3-Chloro-4-(1-cyano-1-methylethyl)phenyl]ethyl}-2-(6,7-difluoro-1H-benzimidazol-1-yl)acetamide To a solution of (6,7-difluoro-1H-benzimidazol-1-yl)acetic acid (285 mg, 1.35 mmol) prepared according to scheme 2, 2-[4-(1-aminoethyl)-2-chlorophenyl]-2-methylpropanenitrile (300 mg 1.35 mmol) prepared according to scheme 17 and DMAP (325 mg, 2.69 mmol) stirred in anhydrous DMF (3.0 mL) is added HATU (511 mg, 1.35 mmol) after 18 hours of stirring, the mixture is diluted with Methanol (200 µL) the solution is purified directly on a preparative LCMS system equipped with a Synergi Polar (4u) 21.2×50 mm column, mobile phase: A=water (0.1% TFA), B=MeCN using a short 40 to 60% B 10 min. gradient method. The pure fractions are combined the TFA neutralized with a 4N NaOH solution and then extracted with ethyl acetate which is separated dried over anhydrous $Na_2SO_4$, filtered and concentrated under reduced pressure to provide the expected product (+) and (−)-N-{1-[3-chloro-4-(1-cyano-1-methylethyl)phenyl]ethyl}-2-(6,7-difluoro-1H-benzimidazol-1-yl)acetamide (300 mg, 55%) as a white solid. 1H NMR (400 MHz, METHANOL-D4) δ ppm 1.50 (d, J=7.03 Hz, 3H) 1.83 (s, 6 H) 5.02 (q, J=7.03 Hz, 1H) 5.14 (s, 2H) 7.17 (ddd, J=11.33, 8.98, 7.42 Hz, 1H) 7.33 (dd, J=8.20, 1.95 Hz, 1H) 7.43 (ddd, J=8.89, 3.81, 1.37 Hz, 1H) 7.47 (d, J=2.34 Hz, 1H) 7.51 (d, J=8.20 Hz, 1H) 8.13 (s, 1H), MS [M+H], calcd: 379.1. found: 379.3.

It is believed that the enantiomers could be separated by chiral HPLC: Gilson prep pumps, Flow rate: 18 ml/min, Column: Chiralcel OD 21×250 mm (5µ), Mobile phase: A=Hexane (0.1% DEA) B=EtOH (0.1% DEA), 80% A:20% B isocratic.

Example 30

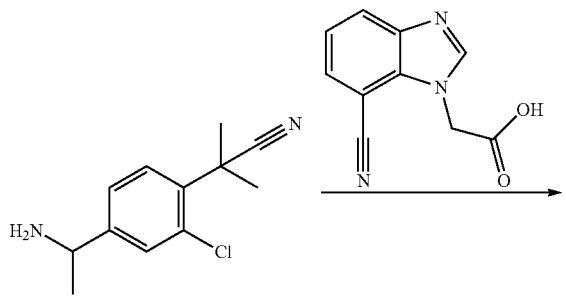

(+) and (−)-N-{1-[3-Chloro-4-(1-cyano-1-methyl-ethyl)phenyl]ethyl}-2-(7-cyano-1H-benzimidazol-1-yl)acetamide To a solution of (7-cyano-1H-benzimidazol-1-yl)acetic acid (271 mg, 1.35 mmol) prepared according to scheme 3, 2-[4-(1-aminoethyl)-2-chlorophenyl]-2-methylpropanenitrile (300 mg 1.35 mmol) prepared according to scheme 17 and DMAP (325 mg, 2.69 mmol) stirred in anhydrous DMF (3.0 mL) is added HATU (511 mg, 1.35 mmol) after 18 hours of stirring, the mixture is diluted with Methanol (200 μL) the solution is purified directly on a preparative LCMS system equipped with a Synergi Polar (4u) 21.2×50 mm column, mobile phase: A=water (0.1% TFA), B=MeCN using a short 40 to 60% B 10 min. gradient method. The pure fractions are combined the TFA neutralized with a 4N NaOH solution and then extracted with ethyl acetate which is separated dried over anhydrous $Na_2SO_4$, filtered and concentrated under reduced pressure to provide the expected product (+) and (−)-N-{1-[3-chloro-4-(1-cyano-1-methylethyl)phenyl]ethyl}-2-(7-cyano-1H-benzimidazol-1-yl)acetamide (290 mg, 53%) as a white solid. 1H NMR (400 MHz, METHANOL-D4) δ ppm 1.50 (d, J=7.03 Hz, 3H) 1.83 (s, 6 H) 5.02 (q, J=7.03 Hz, 1H) 5.14 (s, 2H) 7.17 (ddd, J=11.33, 8.98, 7.42 Hz, 1H) 7.33 (dd, J=8.20, 1.95 Hz, 1H) 7.43 (ddd, J=8.89, 3.81, 1.37 Hz, 1H) 7.47 (d, J=2.34 Hz, 1H) 7.51 (d, J=8.20 Hz, 1H) 8.13 (s, 1H), MS [M+H], calcd: 417.1. found: 417.3.

It is believed that the enantiomers could be separated by chiral HPLC: Gilson prep pumps, Flow rate: 18 ml/min, Column: Chiralcel OD 21×250 mm (5μ), Mobile phase: A=Hexane (0.1% DEA) B=EtOH (0.1% DEA), 80% A:20% B isocratic.

Example 31

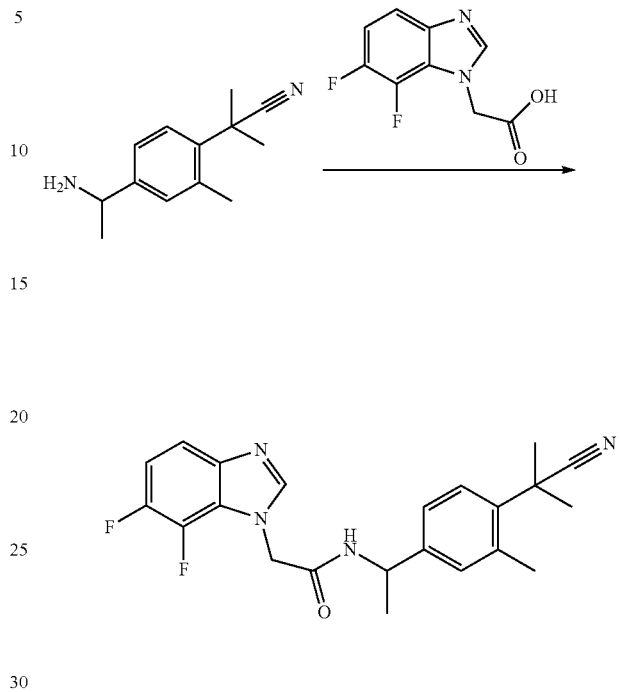

(+) and (−)-2-(6,7-Difluoro-1H-benzimidazol-1-yl)-N-{1-[4-(1-cyano-1-methylethyl)-3-methylphenyl]ethyl}acetamide To a solution of (6,7-difluoro-1H-benzimidazol-1-yl)acetic acid (500 mg, 2.36 mmol) prepared according to scheme 2, 2-{4-[1-aminoethyl]-2-methylphenyl}-2-methylpropanenitrile (477 mg, 2.36 mmol) prepared according to scheme 16 and DMAP (570 mg, 4.71 mmol) stirred in anhydrous DMF (4.0 mL) is added HATU (896 mg, 2.36 mmol) after 18 hours of stirring, the mixture is diluted with EtOAc (100 mL). The organic phase is washed with distilled water, dried over anhydrous $MgSO_4$. The mixture is filtered and concentrated. The product is purified on a preparative LCMS system equipped with a Synergi Polar (4u) 21.2×50 mm column, mobile phase: A=water (0.1% TFA), B=MeCN using a short 40 to 60% B 10 min. gradient method. The pure fractions are combined the TFA neutralized with a 4N NaOH solution and then extracted with ethyl acetate which is separated dried over anhydrous $Na_2SO_4$, filtered and concentrated under reduced pressure to provide the expected product (+) and (−)-2-(6,7-difluoro-1H-benzimidazol-1-yl)-N-{1-[4-(1-cyano-1-methylethyl)-3-methylphenyl]ethyl}acetamide (627 mg, 67%) as a white solid. 1H NMR (400 MHz, METHANOL-D4) δ ppm 1.48 (d, J=7.03 Hz, 3 H) 1.75 (s, 6H) 2.61 (s, 3H) 4.99 (q, J=7.03 Hz, 1H) 5.12 (s, 2H) 7.12-7.25 (m, 3H) 7.33 (d, J=8.20 Hz, 1H) 7.42 (ddd, J=8.89, 3.61, 1.17 Hz, 1H) 8.13 (s, 1H), MS [M+H], calcd: 397.2. found: 397.2.

It is believed that the enantiomers could be separated by chiral HPLC: Gilson prep pumps, Flow rate: 18 ml/min, Column: Chiralcel OD 21×250 mm (5μ), Mobile phase: A=Hexane (0.1% DEA) B=EtOH (0.1% DEA), 80% A:20% B isocratic.

Example 32

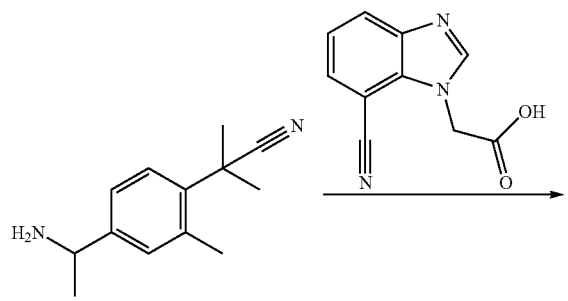

(+) and (−)-2-(7-Cyano-1H-benzimidazol-1-yl)-N-{1-[4-(1-cyano-1-methylethyl)-3-methylphenyl]ethyl}acetamide To a solution of (7-cyano-1H-benzimidazol-1-yl)acetic acid (100 mg, 0.50 mmol) prepared according to scheme 3, 2-{4-[1-aminoethyl]-2-methylphenyl}-2-methylpropanenitrile (101 mg, 0.50 mmol) prepared according to scheme 16 and DMAP (120 mg, 1.00 mmol) stirred in anhydrous DMF (2.0 mL) is added HATU (189 mg, 0.50 mmol) after 18 hours of stirring, the mixture is diluted with Methanol (200 μL) the solution is purified directly on a preparative on a preparative LCMS system equipped with a Synergi Polar (4u) 21.2×50 mm column, mobile phase: A=water (0.1% TFA), B=MeCN using a short 40 to 60% B 10 min. gradient method. The pure fractions are combined the TFA neutralized with a 4N NaOH solution and then extracted with ethyl acetate which is separated dried over anhydrous $Na_2SO_4$, filtered and concentrated under reduced pressure to provide the expected product (+) and (−)-2-(7-Cyano-1H-benzimidazol-1-yl)-N-{1-[4-(1-cyano-1-methylethyl)-3-methylphenyl]ethyl}acetamide (143 mg, 75%) as a white solid. 1H NMR (400 MHz, METHANOL-D4) δ ppm 1.49 (d, J=7.03 Hz, 3H) 1.75 (s, 6H) 2.61 (s, 3H) 4.99 (q, J=7.03 Hz, 1H) 5.28-5.40 (m, 2H) 7.21-7.29 (m, 2H) 7.33 (d, J=8.20 Hz, 1H) 7.37-7.44 (m, 1H) 7.69 (dd, J=7.42, 0.78 Hz, 1H) 7.98 (dd, J=8.20, 1.17 Hz, 1H) 8.27 (s, 1H) MS [M+H], calcd: 386.2. found: 386.2.

It is believed that the enantiomers could be separated by chiral HPLC: Gilson prep pumps, Flow rate: 18 ml/min, Column: Chiralcel OD 21×250 mm (5μ), Mobile phase: A=Hexane (0.1% DEA) B=EtOH (0.1% DEA), 80% A:20% B isocratic.

Example 33

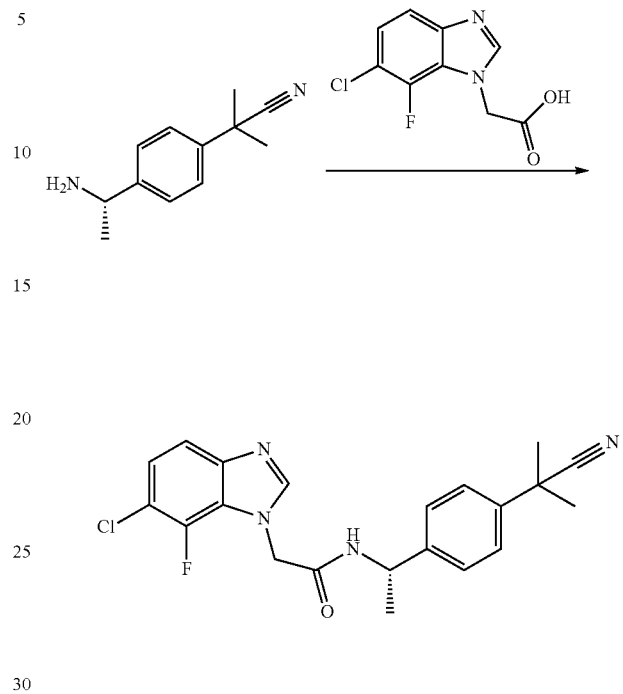

(S)-(−)2-(6-chloro-7-fluoro-1H-benzimidazol-1-yl)-N-{[4-(1-cyano-1-methylethyl)phenyl]ethyl}acetamide To a solution of (6-chloro-7-fluoro-1H-benzimidazol-1-yl)acetic acid (100 mg, 0.44 mmol) prepared according to scheme 13, (S) (−)-2-{4-[1-aminoethyl]phenyl}-2-methyl-propanenitrile (88.5 mg 0.44 mmol) prepared according to scheme 20 or 21 and DMAP (106 mg, 0.88 mmol) stirred in anhydrous DMF (2.0 mL) is added HATU (166 mg, 0.44 mmol) after 18 hours of stirring, the mixture is diluted with methanol (200 μL) the solution is purified directly on a preparative LCMS system equipped with a Synergi Polar (4u) 21.2×50 mm column, mobile phase: A=water (0.1% TFA), B=MeCN using a short 40 to 60% B 10 min. gradient method. The pure fractions are combined the TFA neutralized with a 4N NaOH solution and then extracted with ethyl acetate which is separated dried over anhydrous $Na_2SO_4$, filtered and concentrated under reduced pressure to provide the expected product (S)-(−)-2-(6-chloro-7-fluoro-1H-benzimidazol-1-yl)-N-{1-[4-(1-cyano-1-methylethyl)-3-methylphenyl]ethyl}acetamide (290 mg, 53%) as a clear solid. 1H NMR (400 MHz, METHANOL-D4) δ ppm 1.50 (d, J=7.03 Hz, 3H) 1.69 (s, 6H) 5.03 (q, J=7.01 Hz, 1H) 5.07-5.18 (m, 2H) 7.29 (dd, J=9.37, 6.64 Hz, 3H) 7.39 (d, J=8.59 Hz, 2H) 7.44 (d, J=9.37 Hz, 1H) 7.48 (d, J=8.59 Hz, 2H) 8.14 (s, 1H) MS [M+H], calcd: 399.1. found: 399.2, $[\alpha]_D$=−138° (C=0.5 METHANOL)

Example 34

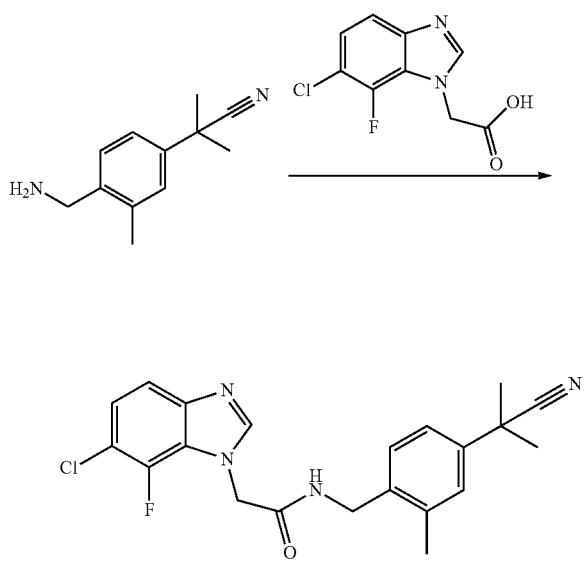

2-(6-chloro-7-fluoro-1H-benzimidazol-1-yl)-N-{[4-(1-cyano-1-methylethyl)-2-methylbenzyl]acetamide To a solution of (6-chloro-7-fluoro-1H-benzimidazol-1-yl)acetic acid (85 mg, 0.37 mmol) prepared according to scheme 13, 2-[4-(aminomethyl)-3-methylphenyl]-2-methylpropanenitrile (70 mg 0.37 mmol) prepared according to scheme 19 and DMAP (90 mg, 0.74 mmol) stirred in anhydrous DMF (2.0 mL) is added HATU (142 mg, 0.37 mmol) after 18 hours of stirring, the mixture is diluted with methanol (200 μL) the solution is purified directly on a preparative LCMS system equipped with a Synergi Polar (4u) 21.2×50 mm column, mobile phase: A=water (0.1% TFA), B=MeCN using a short 30 to 60% B 10 min. gradient method. The pure fractions are combined the TFA neutralized with a 4N NaOH solution and then extracted with ethyl acetate which is separated dried over anhydrous $Na_2SO_4$, filtered and concentrated under reduced pressure to provide the expected product 2-(6-chloro-7-fluoro-1H-benzimidazol-1-yl)-N-{[4-(1-cyano-1-methylethyl)-2-methylbenzyl]acetamide (18 mg, 12%) as a clear solid. 1H NMR (400 MHz, METHANOL-D4) δ ppm 1.46 (d, J=7.03 Hz, 3H) 1.68 (s, 6H) 2.38 (s, 3H) 5.05-5.16 (m, 2H) 5.21 (q, J=6.90 Hz, 1H) 7.25-7.31 (m, 2H) 7.35 (dd, J=8.98, 1.95 Hz, 1H) 7.41 (d, J=8.20 Hz, 1H) 7.44 (d, J=8.98 Hz, 1H) 8.14 (s, 1H), MS [M+H], calcd: 413.2. found: 413.3.

Pharmacology:
Biological Evaluation Human TRPV1, Calcium Mobilization FLIPR™ Assay.

The compound activity in the present invention ($IC_{50}$) is measured using a 384 plate-based imaging assay that monitors drug induced intracellular $Ca^2$ level in whole cells. Activation of hTRPV1 (human Transient Potential Receptor V1, corresponds to accession number: AAM89472 with the following modification, a leucine instead of a phenylalanine is present at position 589), receptors expressed in HEK T-Rex cells (human embryonic kidney, tetracycline-regulated cells) was quantified in a Molecular Devices FLIPR II™ instrument as an increase in fluorescent signal. Inhibition of hTRPV1 by compounds is determined by the decrease in fluorescent signal in response to 20 nM capsaicin activation. HEK T-Rex hVR1 inducible cells are grown in supplemented Dulbecco's modification eagle's medium 1× (DMEM, Wisent, 319-005-CL) with 10% Foetal bovine serum (Wisent, 090850), 2 mM L-Glutamine (Wisent, 609-065-EL), 5 μg/ml Blasticidine S HCL (Invitrogen R-210-01) & 350 μg/ml Zeocin (Invitrogen R-250-05). Cells are plated in 384-black polylysine coated plate (falcon, BD) at 10000 cells/well/50 μl for 16 hours or 5500 cells/well/50 μl for 48 hours in a humidified incubator (5% $CO_2$ and 37° C.) in DMEM medium without selection agent. HEK T-Rex hVR1 cells are induced with 0.1 μg/ml Tetracycline (Invitrogen, 550205) 16 hours prior to the experiment. The day of the experiment, the media is removed from the cell plates by inversion. A loading solution of 30 μl of Hank's balanced salt solution, 1 mM $CaCl_2$ and 5 mM Glucose pH 7.4 (Wisent, 311-520-VL,) with calcium indicator dye FLUO-4 AM 4 μM (Molecular Probes F14202) and Pluronic F-127 0.004% (Invitrogen P3000MP) is added to each well using a Labsystems multidrop. The plates are incubated at 37° C. for 30-40 minutes prior to start the experiment. The incubation is terminated by washing the cells four times in assay buffer using an Skatron Embla (Moleculare Devices corp), leaving a residual 25 μL buffer/well. Cell plates are then transferred to the FLIPR, ready for compound additions. The day of experiment, capsaicin and compounds are diluted in three-fold concentration range (10 points serial dilution) for addition by FLIPR instrument. For all calcium assays, a baseline reading is taken for 10 seconds followed by the addition of 12.5 μl of compounds, resulting in a total well volume of 37.5 μl. Data is collected every second for 60 pictures and then every 10 seconds for 23 pictures prior to the addition of agonist for a total of 300 seconds. Before agonist addition, a second baseline reading is taken for 10 seconds followed by the addition of 12.5 μl of agonist or buffer, producing a final volume of 50 μl. After agonist stimulation, the FLIPR continues to collect data every second for 60 pictures and then every 10 seconds for 21 pictures for a total of 280 seconds. The fluorescence emission is read using filter 1 (emission 520-545 nm) by the FLIPR on board CCD camera.

Compounds having antagonistic properties against the hVR1 will inhibit the increase in intracellular calcium in response to the capsaicin addition, Consequently leading to a reduction in fluorescence signal. Data is exported by the FLIPR program as a sum of fluorescence calculated under the curve upon the addition of capsaicin. Data is analyzed using sigmoidal fits of a non-linear curve-fitting program (XLfit version 5.0.6 from ID Business Solutions Limited, Guildford, UK). Maximum inhibition, Hill slope and IC50 data for each compound are generated.

List of Abbreviations:
VR1 vanilloid receptor 1
IBS irritable bowel syndrome
IBD inflammatory bowel disease
FLIPR Fluorescence Imaging Plate Reader
GERD gastro-esophageal reflux disease
DRG Dorsal Root Ganglion
BSA Bovine Serum Albumin
HEPES 4-(2-Hydroxyethyl)piperazine-1-ethanesulfonic acid
EGTA Ethylene glycol-bis(2-aminoethylether)-N,N,N',N'-tetraacetic acid
DMEM Dulbeccos Modified Eagle's Medium

What is claimed is:

1. A compound of Formula I:

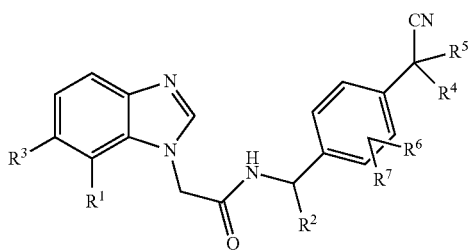

wherein:
R¹ is selected from CN, halogen, or C(=O)CH₃;
R² is selected from methyl or H;
R³ is selected from H, or halogen;
R⁴ and R⁵ are each independently selected from methyl or ethyl or R⁴ or
R⁵ together with the carbon atom to which they are attached form a 3-6 membered cycloalkyl or a 5 or 6 membered heterocycloalkyl group;
R⁶ and R⁷ are each independently selected from H, halogen, methyl, or ethyl;
or pharmaceutically acceptable salt thereof;
wherein the compound of Formula I is not
N-[4-(1-cyano-1-methylethyl)benzyl]-2-(6,7-difluoro-1H-benzimidazol-1-yl)acetamide;
2-(7-chloro-1H-benzimidazol-1-yl)-N-[4-(1-cyano-1-methylethyl)-3-fluorobenzyl]acetamide;
(+)-2-(7-cyano-1H-benzimidazol-1-yl)-N-{1-[4-(1 cyanocyclohexyl)phenyl]ethyl}acetamide;
(+)-N-{1-[4-(1-cyano-1-methylethyl)-2-methylphenyl]ethyl}-2-(6,7-difluoro-1H-benzimidazol-1-yl)acetamide;
(+,-)-2-(6-chloro-7-fluoro-1H-benzimidazol-1-yl)-N-{1-[4-(1-cyano-1-methylethyl)-2-methylphenyl]ethyl}acetamide;
(+)-2-(7-acetyl-1H-benzimidazol-1-yl)-N-{1-[4-(1-cyano-1-methylethyl)phenyl]ethyl}acetamide;
(+)-N-{1-[4-(1-cyanocyclohexyl)phenyl]ethyl}-2-(6,7-difluoro-1H-benzimidazol-1-yl)acetamide;
(+)-2-(7-chloro-6-fluoro-1H-benzimidazol-1-yl)-N-{1-[4-(1-cyano-1-methylethyl)-3-fluorophenyl]ethyl}acetamide;
(+)-N-{1-[4-(1-cyano-1-methylethyl)-3-fluorophenyl]ethyl}-2-(6,7-difluoro-1H-benzimidazol-1-yl)acetamide;
(+)-N-{1-[4-(1-cyanocyclobutyl)phenyl]ethyl}-2-(6,7-difluoro-1H-benzimidazol-1-yl)acetamide;
(R)(+)-N-{1-[4-(1-cyano-1-methylethyl)phenyl]ethyl}-2-(6,7-difluoro-1H-benzimidazol-1-yl)acetamide;
(R)(+)-2-(7-cyano-1H-benzimidazol-1-yl)-N-{1-[4-(1-cyano-1-methylethyl)phenyl]ethyl}acetamide;
(+)-2-(7-cyano-1H-benzimidazol-1-yl)-N-{1-[4-(1-cyano-1-methylethyl)-3-fluorophenyl]ethyl}acetamide;
(+)-2-(7-acetyl-1H-benzimidazol-1-yl)-N-{1-[4-(1-cyano-1-methylethyl)-3-fluorophenyl]ethyl}acetamide; or
(R)(+)-N-{1-[4-(1-cyano-1-ethylpropyl)phenyl]ethyl}-2-(6,7-difluoro-1H-benzimidazol-1-yl)acetamide.

2. A compound of Formula I according to claim 1 or a pharmaceutically acceptable salt thereof, wherein R¹ is independently selected from chlorine or fluorine.

3. A compound of Formula I according to claim 1 or a pharmaceutically acceptable salt thereof, wherein R³ is selected from chlorine or fluorine.

4. A compound of Formula I according to claim 2 or a pharmaceutically acceptable salt thereof, wherein R³ is selected from chlorine or fluorine.

5. A compound of Formula I according to claim 1 or a pharmaceutically acceptable salt thereof, wherein R⁴ and R⁵ are independently selected from methyl or ethyl.

6. A compound of Formula I according to claim 2 or a pharmaceutically acceptable salt thereof, wherein R⁴ and R⁵ are independent selected from methyl or ethyl.

7. A compound of Formula I according to claim 3 or a pharmaceutically acceptable salt thereof, wherein R⁴ and R⁵ are independent selected from methyl or ethyl.

8. A compound of Formula I according to claim 4 or a pharmaceutically acceptable salt thereof, wherein R⁴ and R⁵ are independently selected from methyl or ethyl.

9. A compound of Formula I according to claim 1 or a pharmaceutically acceptable salt thereof, wherein R⁴ and R⁵ together with the carbon atom to which they are attached form a 3,4, or 6 membered cycloalkyl or a 5 or 6 membered heterocycloalkyl group.

10. A compound of Formula I according to claim 2 or a pharmaceutically acceptable salt thereof, wherein R⁴ and R⁵ together with the carbon atom to which they are attached form a 3,4, or 6 membered cycloalkyl or a 5 or 6 membered heterocycloalkyl group.

11. A compound of Formula I according to claim 3 or a pharmaceutically acceptable salt thereof, wherein R⁴ and R⁵ together with the carbon atom to which they are attached form a 3,4, or 6 membered cycloalkyl or a 5 or 6 membered heterocycloalkyl group.

12. A compound of Formula I according to claim 4 or a pharmaceutically acceptable salt thereof, wherein R⁴ and R⁵ together with the carbon atom to which they are attached form a 3,4, or 6 membered cycloalkyl or a 5 or 6 membered heterocycloalkyl group.

13. A compound of Formula I according to claim 1 or a pharmaceutically acceptable salt thereof, wherein R⁶ and R⁷ are each independently selected from fluorine or chlorine.

14. A compound of Formula I according to claim 1 or a pharmaceutically acceptable salt thereof, wherein R⁶ and R⁷ are each H.

15. A compound of Formula I according to claim 2 or a pharmaceutically acceptable salt thereof, wherein R⁶ and R⁷ are each H.

16. A compound of Formula I according to claim 3 or a pharmaceutically acceptable salt thereof, wherein R⁶ and R⁷ are each H.

17. A compound of Formula I according to claim 4 or a pharmaceutically acceptable salt thereof, wherein R⁶ and R⁷ are each H.

18. A compound of Formula I according to claim 5 or a pharmaceutically acceptable salt thereof, wherein R⁶ and R⁷ are each H.

19. A compound of Formula I according to claim 6 or a pharmaceutically acceptable salt thereof, wherein R⁶ and R⁷ are each independently selected from H.

20. A compound of Formula I according to claim 7 or a pharmaceutically acceptable salt thereof, wherein R⁶ and R⁷ are each H.

* * * * *